(12) United States Patent
Sher et al.

(10) Patent No.: US 11,899,024 B2
(45) Date of Patent: Feb. 13, 2024

(54) TREATMENT AND DIAGNOSIS OF PARKINSON'S DISEASE USING ISOLATED AND ENRICHED POPULATIONS OF BIOFLUID-DERIVED EXTRACELLULAR VESICLES

(71) Applicant: Exosome Diagnostics, Inc., Waltham, MA (US)

(72) Inventors: Mia Sher, Maynard, MA (US); Erez Eitan, Waltham, MA (US); Christine Coticchia, Waltham, MA (US); Johan Karl Olov Skog, Lincoln, MA (US); Robert Kitchen, Somerville, MA (US); Seth Yu, Waltham, MA (US)

(73) Assignee: Exosome Diagnostics, Inc., Waltham, MA (US)

( * ) Notice: Subject to any disclaimer, the term of this patent is extended or adjusted under 35 U.S.C. 154(b) by 162 days.

(21) Appl. No.: 16/629,000

(22) PCT Filed: Jul. 12, 2018

(86) PCT No.: PCT/US2018/041884
§ 371 (c)(1),
(2) Date: Jan. 6, 2020

(87) PCT Pub. No.: WO2019/014486
PCT Pub. Date: Jul. 17, 2019

(65) Prior Publication Data
US 2020/0292561 A1 Sep. 17, 2020

Related U.S. Application Data

(60) Provisional application No. 62/678,853, filed on May 31, 2018, provisional application No. 62/531,845, filed on Jul. 12, 2017.

(51) Int. Cl.
*G01N 33/68* (2006.01)
*G01N 33/537* (2006.01)
*C12N 15/10* (2006.01)

(52) U.S. Cl.
CPC ..... *G01N 33/6896* (2013.01); *C12N 15/1013* (2013.01); *G01N 33/537* (2013.01); *G01N 2333/705* (2013.01); *G01N 2800/28* (2013.01)

(58) Field of Classification Search
CPC ............ G01N 33/6896; G01N 33/537; G01N 2333/705; G01N 2800/28; G01N 33/543; G01N 33/54326; G01N 33/57484; G01N 33/68; G01N 2333/4709
See application file for complete search history.

(56) References Cited

U.S. PATENT DOCUMENTS

| 4,767,710 A | 8/1988 | Bigbee et al. |
| 5,219,727 A | 6/1993 | Wang et al. |
| 5,538,871 A | 7/1996 | Nuovo et al. |
| 5,556,773 A | 9/1996 | Yourno |
| 5,582,981 A | 12/1996 | Toole et al. |
| 5,639,606 A | 6/1997 | Willey |
| 5,639,611 A | 6/1997 | Wallace et al. |
| 5,766,840 A | 6/1998 | Kim et al. |
| 5,840,867 A | 11/1998 | Toole et al. |
| 6,004,755 A | 12/1999 | Wang |
| 6,180,778 B1 | 1/2001 | Bastian et al. |
| 6,525,154 B1 | 2/2003 | Shea et al. |
| 6,812,023 B1 | 11/2004 | Lamparski et al. |
| 6,893,837 B2 | 5/2005 | Slamon et al. |
| 6,899,863 B1 | 5/2005 | Dhellin et al. |
| 6,913,879 B1 | 7/2005 | Schena |
| 6,994,960 B1 | 2/2006 | Foote et al. |
| 7,074,563 B2 | 7/2006 | Köster |
| 7,186,512 B2 | 3/2007 | Martienssen et al. |
| 7,198,893 B1 | 4/2007 | Köster et al. |
| 7,198,923 B1 | 4/2007 | Abrignani et al. |
| 7,332,553 B2 | 2/2008 | Sellergren et al. |
| 7,364,848 B2 | 4/2008 | Van Beuningen et al. |
| 7,378,245 B2 | 5/2008 | Liu |
| 7,384,589 B2 | 6/2008 | Hart et al. |
| 9,707,333 B2 | 7/2017 | Ichim et al. |
| 11,407,991 B2 | 8/2022 | Comper et al. |
| 2003/0199078 A1 | 10/2003 | Kleiber et al. |
| 2004/0121411 A1 | 6/2004 | Roberts et al. |
| 2004/0204661 A1 | 10/2004 | Epler |

(Continued)

FOREIGN PATENT DOCUMENTS

| CN | 106062559 A | 10/2016 |
| WO | WO 01/36601 A | 5/2001 |

(Continued)

OTHER PUBLICATIONS

Gria2, Wikipedia, 11 pages, retrieved from internet on Dec. 18, 2021. (Year: 2021).*
Faure J et al. Exosomes are released by cultured cortical neurones. Mol. Cell. Neurosci. 31, 642-648. (Year: 2006).*
Kalani A et al. Exosomes: mediators of neurodegeneration, neuroprotection and therapeutics. Mol. Neurobiol. 49(1), 590-600, 19 pages. (Year: 2014).*
Ko J et al. Smartphone-enabled optofluidic exosome diagnostic for concussion recovery. Scientific Reports, 6:31215, 12 pages. (Year: 2016).*

(Continued)

*Primary Examiner* — Kimberly Ballard
(74) *Attorney, Agent, or Firm* — COOLEY LLP; Ivor R. Elrifi; Matthew Pavao

(57) ABSTRACT

The invention relates generally to a process for isolating subpopulations of EVs to identify biomarkers useful identifying, determining the progression of, and/or prognosing a disease, including a neurological disease. More particularly, the present invention relates to detection technology of various exosomal biomarkers including proteins, protein modifications, sugars, RNA, DNA, lipids, and metabolites, and combinations thereof.

8 Claims, 35 Drawing Sheets

(56) References Cited

U.S. PATENT DOCUMENTS

| | | |
|---|---|---|
| 2005/0063961 A1 | 3/2005 | Friedlander et al. |
| 2006/0211032 A1 | 9/2006 | Huang et al. |
| 2007/0254351 A1 | 11/2007 | Abrignani et al. |
| 2008/0268429 A1 | 10/2008 | Pietrzkowski |
| 2009/0311270 A1 | 12/2009 | Allen et al. |
| 2009/0311715 A1 | 12/2009 | Owen et al. |
| 2010/0184046 A1 | 7/2010 | Klass et al. |
| 2010/0196426 A1 | 8/2010 | Skog et al. |
| 2010/0316688 A1 | 12/2010 | Bamdad |
| 2011/0003704 A1 | 1/2011 | Skog et al. |
| 2011/0053157 A1 | 3/2011 | Skog et al. |
| 2011/0089315 A1 | 4/2011 | Walt et al. |
| 2011/0195426 A1 | 8/2011 | Russo et al. |
| 2012/0142001 A1 | 6/2012 | Skog et al. |
| 2012/0238467 A1 | 9/2012 | Taylor |
| 2013/0029339 A1 | 1/2013 | Skog et al. |
| 2013/0040833 A1 | 2/2013 | Noerholm et al. |
| 2013/0131194 A1 | 5/2013 | Skog et al. |
| 2013/0202559 A1 | 8/2013 | Skog et al. |
| 2013/0295574 A1 | 11/2013 | Skog et al. |
| 2014/0045915 A1 | 2/2014 | Skog et al. |
| 2014/0147839 A1 | 5/2014 | Chen et al. |
| 2014/0162888 A1 | 6/2014 | Kuslich et al. |
| 2014/0194319 A1 | 7/2014 | Skog et al. |
| 2014/0194613 A1 | 7/2014 | Skog et al. |
| 2014/0212871 A1 | 7/2014 | Comper et al. |
| 2015/0038335 A1 | 2/2015 | Skog et al. |
| 2015/0119278 A1* | 4/2015 | Goetzl ............... G01N 33/6896 435/7.1 |
| 2015/0176073 A1 | 6/2015 | Skog |
| 2015/0252428 A1 | 9/2015 | Comper et al. |
| 2015/0322532 A1 | 11/2015 | Skog et al. |
| 2015/0353920 A1 | 12/2015 | Enderle et al. |
| 2016/0002736 A1 | 1/2016 | Noerholm et al. |
| 2016/0024491 A1 | 1/2016 | Skog et al. |
| 2016/0075788 A1 | 3/2016 | Skog et al. |
| 2016/0153053 A1 | 6/2016 | Skog et al. |
| 2016/0161502 A1 | 6/2016 | Duffin et al. |
| 2016/0177401 A1 | 6/2016 | Skog et al. |
| 2016/0201121 A1 | 7/2016 | Chen et al. |
| 2016/0216253 A1 | 7/2016 | Balaj et al. |
| 2016/0237422 A1 | 8/2016 | Comper et al. |
| 2016/0348095 A1 | 12/2016 | Russo et al. |
| 2016/0362678 A1 | 12/2016 | Skog et al. |
| 2017/0088898 A1 | 3/2017 | Skog et al. |
| 2017/0114389 A1 | 4/2017 | Russo et al. |
| 2017/0198280 A1 | 7/2017 | Skog et al. |
| 2017/0314075 A1 | 11/2017 | Skog et al. |
| 2018/0340945 A1* | 11/2018 | Mitsuhashi ............. A61P 25/28 |

FOREIGN PATENT DOCUMENTS

| | | | |
|---|---|---|---|
| WO | WO 2003/023065 A1 | 3/2003 | |
| WO | WO 2003/050290 A2 | 6/2003 | |
| WO | WO 2005/083081 A1 | 9/2005 | |
| WO | WO 2006/113590 A2 | 10/2006 | |
| WO | WO 2007/127848 A1 | 11/2007 | |
| WO | WO 2009/100029 A1 | 8/2009 | |
| WO | WO 2010/065765 A2 | 6/2010 | |
| WO | WO 2011/009104 A1 | 1/2011 | |
| WO | WO 2012/155014 A1 | 5/2012 | |
| WO | WO-2015200851 A1 * | 12/2015 | ......... G01N 33/6896 |
| WO | WO 2017/053516 A1 | 3/2017 | |
| WO | WO 2017/074658 A1 | 5/2017 | |
| WO | WO-2019014486 A1 | 1/2019 | |

OTHER PUBLICATIONS

Tofaris GK. A critical assessment of exosomes in the pathogenesis and stratification of Parkinson's disease. J. Parkinson's Dis. 7, 569-576. (Year: 2017).*

Lachenal et al. (2011) Release of exosomes from differentiated neurons and its regulation by synaptic glutamaterigic activity. Mol Cell Neurosci. 46:409-418. (Year: 2011).*

Witwer et al. (2013) Standardization of sample collection, isolation and analysis methods in extracellular vesicle research. J Extracellular Vesicles, 2:20360, 25 pages. (Year: 2013).*

Ko, J. et al., "Smartphone-enabled optofluidic exosome diagnostic for concussion recovery," Scientific Reports, 6:31215 (2016), 12 pages; doi:10.1038/srep31215.

Oksvold, M.P. et al., "Chapter 27: Magnetic Bead-Based Isolation of Exosomes," Methods in Molecular Biology, 1218:465-481 (2015).

Zarovni, N. et al., "Integrated isolation and quantitative analsysi of exosome shuttled proteins and nucleic acids using immunocapture approaches," Methods, 87:46-58 (2015).

Zorro, D. & Zarovni, N., "Chapter 22: Extraction and Analysis of Extracellular Vesicle-Associated miRNAs Following Antibody-Based Extracellular Vesicle Capture from Plasma Samples," Plant Genotyping, Extracellular Vesicles: Methods and Protocols, Methods in Molecular Biology, 1660:269-285 (2017); doi: 10.1007/978-1-4939-7253-1_22.

Abravaya, et al., "Detection of point mutations with a modified ligase chain reaction (Gap-LCR)." Nucleic Acids Research (1995); 23 (4): 675-682.

Agarwal, et al., "Immunostaining as an adjunct to cytology for diagnosis of pancreatic adenocarcinoma." Clin Gastroenterol Hepatol. (2008); 6 (12): 1425-1431.

Agis, et al., "Enumeration and immunohistochemical characterisation of bone marrow basophils in myeloproliferative disorders using the basophil specific monoclonal antibody 2D7." Journal of Clinical Pathology (2006); 59 (4): 396-402.

Agis, et al., "Identification of basogranulin (BB1) as a novel immunohistochemical of basophils in normal bone marrow and patients with myeloproliferative disorders." Am J Clin Pathol. (2006); 125 (2): 273-281.

Agre, et al., "Biochemistry of the erythrocyte Rh polypeptides: A review." Yale J Biol Med. (1990); 63: 461-4677.

Ahern, H., "Biochemical, Reagents Kits Offer Scientists Good Return on Investment." The Scientist (1995); 9 (15): 20, 7 pages.

Al-Hajj, et al., "Prospective identification of tumorigenic breast cancer cells." PNAS (2003); 100 (7): 3983-3988.

Allard, et al, "Tumor cells circulate in the peripheral blood of all major carcinomas but not in healthy subjects or patients with nonmalignant diseases." Clin Cancer Res. (2004); 10: 6897-6904.

Al-Nedawi, et al., "Intercellular transfer of the oncogenic receptor EGFRvIII by microvesicles derived from tumour cells." Nat Cell Biol. (2008); 10 (5): 619-624.

Alsayed, et al., "Mechanisms of regulation of CXCR4/SDF-1 (CXCL 12)—dependent migration and homing in multiple myeloma." Blood (2007); 109 (7): 2708-2717.

Alvero, et al., "Molecular phenotyping of human ovarian cancer stem cells unravels the mechanism for repair and chemoresistance." Cell Cycle (2009); 8 (1): 158-166.

Ammons, et al., "In vitro and in vivo pharmacology and pharmacokinetics of a human engineered monoclonal antibody to epithelial cell adhesion molecule." Neoplasia (2003); 5 (2): 146-154.

Andersson, et al., "Glycophorin A as a cell surface marker of early erythroid differentiation in acute leukemia." Int J Cancer (1979); 24 (6): 717-720.

Avent, et al., "Immunochemical analysis of the human erythrocyte Rh polypeptides." J Biol Chem. (1996); 271 (24): 14233-14239.

Baeuerle, et al., "EpCAM (CD326) finding its role in cancer." British J. Cancer (2007); 96(3) : 417-423. Epub Jan. 9, 2007.

Baig, et al., "Hepatocellular carcinoma (HCC) and diagnostic significance of A-fetoprotein (AFP)." J Ayub Med Coll Abbottabad (2009); 21 (1): 72-75.

Baj-Krzyworzeka et al., "Tumour-derived microvesicles carry several surface determinants and mRNA of tumour cells and transfer some of these determinats to monocytes." Cancer Immunology, Immunotherapy (2006); 55 (7): 808-818.

Balamurugan, et al., "Surface immobilization methods for aptamer diagnostic applications." Anal. Bioanal. Chem. (2008); 390(4): 1009-1021.

Ball, et al., "Introduction: workshop summary of the CD15 monoclonal antibody panel from the Fifth International Workshops on Leukocyte." Eur J Morphol. (1995); 33 (2): 95-100.

(56) References Cited

OTHER PUBLICATIONS

Balzar, et al., "The biology of the 17-1A antigen (Ep-CAM)." J Mol Med. (1999); 77 (10): 699-712.
Bao, et al., "Stem cell-like glioma cells promote tumor angiogenesis through vascular endothelial growth fator." Cancer Res. (2006); 66 (16): 7843-7848.
Bao, et al., "Glioma stem cells promote radioresistance by preferential activation of the DNA damge response." Nature (2006); 444 (7120): 756-760.
Bao, et al., "Targeting cancer stem cells through L1 CAM suppresses glioma growth." Cancer Res. (2008); 68 (15): 6043-6048.
Bembridge, et al., "Comparison of monoclonal antibodies with potential specificity for restricted isoforms of the leukocyte common antigen (CD45R)." Vet Immunol Immunopathol. (1993); 39(1-3): 129-136.
Berrington, et al., "Lymphocyte subsets in term and significantly preterm UK infants in the first year of life analysed by single platform flow cytometry." Clin Exp Immunol. (2005); 140 (2): 289-292.
Board, et al., "Platelet-derived growth factor receptor (PDGFR): A target for anticancer therapeutics." Drug Resistance Updates (2005); 8(1-2): 75-83. Epub Apr. 15, 2005.
Boman, et al., "Human colon cancer stem cells: a new paradigm in gastrointestinal oncolgy." J Clin Oncol. (2008); 26(17): 2828-2838.
Bonnet, et al., "Human acute myeloid leukemia is organized as a hierarchy that originates from a primitive hematopoietic cell." Nat Med. (1997); 3(7): 730-737.
Borgono, et al,. "Human kallilrein 14: a new potential biomarker for ovarian and breast cancer." Cancer Res. (2003); 63 (24): 9032-9041.
Borregaard, "Biosynthesis of granule proteins in normal human bone marrow cells. Gelatinase is a marker of terminal neutrophil differentiation." Blood (1995); 85 (3): 812-817.
Bossi, et al., "Molecularly imprinted polymers for the recognition of proteins: the state of the art." Biosens Bioelectron. (2007); 22 (6): 1131-1137.
Chan, et al., "Identification, molecular characterization, clinical prognosis, and therapeutic targeting of human bladder tumor-initiating cells." PNAS (2009); 106(33): 14016-14021.
Chang, et al., "Five Different Anti-Prostate-specific Membrane Antigen (PSMA) Antibodies Confirm PSMA Expression in Tumor-associated Neovasculature." Cancer Res. (1999); 59 (13): 3192-3198.
Chang, et al., "Molecular cloning of mesothelin, a differentiation antigen present on mesothelium, mesothelioams, and ovarian cancers." PNAS (1996); 93(1): 136-140.
Chen et al., "Real-time quantification of microRNAs by stem-loop RT-PCR." Nucleic Acid Research (2005); 33 (20): e179.
Chen, et al., Apolipoprotein E is required for cell proliferation and survival in ovarian cancer. Cancer Res. (2005); 65: 331-337.
Chen, et al., "Microfluidic isolation and transcriptome analysis of serum microvesicles." Lab Chip (2010); 10 (4): 505-511.
Cheruvanky, et al., "Rapid isolation of urinary exosomal biomarkers using a nanomembrane ultrafiltration concentrator." Am J Physiol Renal Physiol. (2007); 292: F1657-F1661.
Ciafrè et al., "Extensive modulation of a set of microRNAs in primary glioblastoma." Biochemical and Biophysical Research Communications (2005); 334: 1351-1358.
Clayton, et al., "Analysis of antigen presenting cell derived exosomes, based on immuno-magnetic isolation and flow cytometry." Journal of Immunological Methods (2001); 247 (1-2): 163-174.
Clement, et al., "Analysis of the monocyte Fc receptors and antibody-mediated cellular interactions required for the induction of T cell proliferation by anti-T3 antibodies." J Immunol. (1985); 135 (1): 165-171.
Coiffier, "Rituximab therapy in malignant lymphoma." Oncogene (2007); 26 (25): 3603-3613.
Collins, et al., "Prospective identification of tumorigenic prostate cancer stem cells." Cancer Res. (2005); 65 (23):10946-10951.

Coren, et al., "CD45 immunoaffinity depletion of vesicles from Jurkat T cells demonstrates that exosomes contain CD45: no evidence for a distinct exosome/HIV-1 budding pathway." Retrovirology (2008); 5: 64, pp. 1-5.
Cotton, et al., "Reactivity of cystosine and thymine in single-base-pair mismatches with hydroxylamine and osmium tetroxide and its application to the study of mutations." Proc Natl Acad Sci U S A (1988); 85 (12): 4397-4401.
Cowell and Lo, "Application of oligonucleotides arrays for coincident comparative genomic hybridization, ploidy status and loss of heterozygosity studies in human cancers." Methods Mol Biol. (2009); 556: 47-65.
Cox, et al., "Characterization of acute lymphoblastic leukemia progenitor cells." Blood (2004); 104 (9): 2919-2925.
Crisan, et al., "A Perivascular Origin for Mesenchymal Stem Cells in Multiple Human Organs." Cell Stem Cell (2008); 3(3): 301-313.
Dallas, et al., "Chemoresistant colorectal cancer cells, the cancer stem cell phenotype, and increased sensitivity to insulin-like growth factor-I receptor inhibition." Cancer Res. (2009); 69 (5):1951-1957.
De Clerck, et al. "Expression of neutrophil activation markers and neutrophil adhesion to chondrocytes in rheumatoid arthritis patients: relationship with disease activity." Res Immunol. (1995); 146 (2): 81-87.
De La Fuente, et al., "Molecular characterization and expression of a novel human leukocyte cell-surface marker homologous to mouse Ly-9." Blood (2001); 97 (11): 3513-3520.
Dhanasekaran, et al. "Delineation of prognostic biomarkers in prostate cancer."Nature (2001) ;412(6849): 822-826.
Ding, et al., "Expression and purification of recombinant cytoplasmic domain of human erythrocyte band 3 with hexahistidine tag or chitin-binding tag in *Escherichia coli*." Protein Expr Purif. (2004); 34 (2): 167-175.
Dirks, P.B., "Glioma migration: clues from the biology of neural progenitor cells and embryonic CNS cell migration." J Neurooncol. (2001); 53 (2): 203-212.
Ducrest, et al., "Flowcytometric anaylsis of basophil counts in human blood and inaccuracy of hematology analyzers." Allergy (2005); 60 (11): 1146-1450.
Eramo, et al., "Identification and expansion of the tumorigenic lung cancer stem cell population." Cell Death Differ. (2008); 15 (3): 504-514. Epub Nov. 30, 2007.
Falleni, et al., "Survivin gene expression in early-stage non-small cell lung cancer." J Pathol. (2003); 200 (5): 620-626.
Fayle, et al., "Isolation of plasma membrane from human blood monocytes. Subcellular fractionation and marker distribution." Eur J Biochem. (1985); 147 (2): 409-419.
Ferrandina, et al., "Expression of CD133-1 and CD133-2 in ovarian cancer." Int J Gynecol Cancer (2008); 18 (3): 506-514. Epub Sep. 13, 2007.
Figarella-Branger, et al., "Differential spectrum of expression of neural cell adhesion molecule isoforms and L1 adhesion molecules on human neuroectodermal tumors." Cancer Res. (1990); 50 (19): 6364-6370.
Fillmore and Kuperwasser, "Human Breast cancer cell lines contain stem-like cells that self-renew, give rise to phenotypically diverse progeny and survive chemotherapy." Breast Cancer Res. (2008); 10(2): R25.
Fink, et al., "Monocyte activation markers during cardiopulmonary bypass." Perfusion (2003); 18 (2): 83-86.
Fischer and Lerman, "[11] Two-dimensional electrophoretic separation of restriction enzyme fragments of DNA." Methods in Enzymology (1979); 68: 183-191.
Fischer and Lerman, "Length-independent separation of DNA restriction fragments in two-dimensional gel electrophoresis." Cell (1979); 16 (1): 191-200.
Flaherty, et al., "CD11/CD18 leukocyte integrins: new signaling receptors for bacterial endotoxin." J Surg Res. (1997); 73 (1): 85-89.
Flanagan, et al., "Localization of the Epstein-Barr virus protwin LMP 1 to exosomes." J Gen Virol. (2003); 84(Pt 7): 1871-1879.
Fong and Kakar, "The role of cancer stem cells and the side population in epithelial ovarian cancer." Histol Histopathol. (2010); 25 (1): 113-120.

(56) References Cited

OTHER PUBLICATIONS

Galli, et al., "Isolation and characterization of tumorigenic, stem-like neural precursors from human glioblastoma." Cancer Res. (2004); 64 (19): 7011-7021.
Gallin, et al., A neutrophil membrane marker reveals two groups of chronic myelogenous leukemia and its absence may be a marker of disease progression. Blood (1986); 68 (2): 343-346.
Geiss, et al., "Direct multiplexed measurement of gene expression with color-coded probe pairs. "Nat Biotechnol. (2008); 26 (3): 317-325.
Ginestier, et al., "ALDH1 is a marker of normal and malignant human mammary stem cells and a predictor of poor clinical outcome." Cell Stem Cell. (2007); (5): 555-567.
Goel, et al., "Pharmacokinetic and safety study of subcutaneously administered weekly ING-1, a human engineere monoclonal antibody targeting human EpCAM, in patients with advanced solid tumors." Ann Oncol. (2007); 18 (10): 1704-1707.
Guatelli, et al., "Isothermal, in virto amplification of nucleic acids by a multienzyme reaction modeled after retroviral replication." Proc Natl Acad Sci U S A. (1990); 87 (5): 1874-1878.
Guerini, et al., "Human leukocyte antigen distribution analysis in North Italian brain glioma patients: an association with HLA-DRB1*14." J Neurooncol. (2006); 77 (2): 213-217. Epud Nov. 29, 2005.
Gürlek, et al., What are the markers of aggressiveness in prolactinomas? Changes in cell biology, extracellular matrix components, angiogenesis and genetics. Eur J Endocrinol. (2007); 156 (2): 143-453.
Hahn, "Molecular Biology of Double-Minute Chromosomes." Bioessay (1993); 15 (7): 477-484.
Hannigan, et al., "Leukocyte-specific gene 1 protien (LSP1) is involved in chemokine KC-activated cytoskeletal reorganization in murine neutrophils in vitro." J Leukoc Biol. (2001); 69 (3): 497-504.
Hanesberg, et al., "Rapid immunomagnetic negative enrichment of neutrophil granulocytes from murine bone marrow for functional sudies in vitro and in vivo." PLoS One (2011); 6(2): e17314.
Heimberger, et al., "The natural history of EGFR and EGFRvIII in glioblastoma patients." Journal of Translational Medicine (2005); 3: 38.
Hemmati, et al., "Cancerous stem cells can arise from pediatric brain tumors." Proc Natl Acad Sci U S A. (2003); 100 (25): 15178-15183.
Hermann, et al., "Distinct populations of cancer stem cells determine tumor growth and metastatic activity in human pancreatic cancer." Cell Stem Cell. (2007); 1 (3): 313-323.
Hessels, et al., "Detection of TMPRSS2-ERG fusion transcript and prostate cancer antigen 3 in urinary sediments may improve diagnosis of prostate cancer." Clin Cancer Res. (2007); 13 (17): 5103-5108.
Hill, et al., "Genetic markers in glioblastoma: prognostic signigicance and future therapeutic implications." Adv Anat Pathol. (2003); 10 (4): 212-217.
Hoffman, et al., "Immunofluorometric quantitation and histochemical localisation of Kallikrein 6." Br J Cancer (2002); 87 (7): 763-771.
Hosen, et al., "CD96 is a leukemic stem cell-specific marker in human acute myeloid leukemia." Proc Natl Acad Sci U S A. (2007); 104 (26): 11008-11013.
Hough, et al., "Coordinately up-regulated genes ovarian cancer." Cancer Res. (2001); 61 (10): 3869-3876.
Hurt, et al., "CD44+CD24− prostate cells are early cancer progenitor/stem cells that provide a model for patients with poor prognosis." Br J Cancer (2008); 98 (4): 756-765.
Ignatova, et al., "Human cortical glial tumors contain neural stem-like cells expressing astroglial and neuronal markers in vitro."0 GLIA (2002); 39 (3):193-206.
Ishikawa, et al., "Chemotherapy-resistant human AML stem cells home to and engraft within the bone-marrow endosteal region." Nat Biotechnol. (2007); 25 (11): 1315-1321.

Jackman, et al., "Impact of epidermal growth factor receptor and KRAS mutations on clinical outcomes in previously untreated non-small cell lung cancer patients: results of an online tumor registry of clinical trials." Clin Cancer Res. (2009); 15 (16): 5267-5273.
Jiang, et al., "Aldehyde dehydrogenase 1 ia a tumor stem cell-associated marker in lung cancer." Mol Cancer Res. (2009); 7 (3): 330-338.
Jiang, et al., "High Dose Chemotherapy and Transplantation of Hematopoietic Progenitors from Murine D3 Embryonic Stem Cells." Journal of Chemotherapy (2005); 17 (3): 302-308.
Jin, et al., "Expression of neural cell adhesion molecule in normal and neoplastic human neuroendocrine tissues." Am J Pathol. (1991); 138 (4): 961-969.
Jin, et al., "Targeting of CD44 eradicates human acute myeloid leukemic stem cells." Nat Med. (2006); 12 (10): 1167-1174.
Johnson, et al., "Surface-immobilized peptide aptamers as probe molecules for protein detection."Anal Chem. (2008); 80 (4): 978-983.
Jonas, et al., "Electron microscopic study of receptor mediated endocytosis of a monoclonal antibody (RoMo-1) against the surface marker CD 14 of human monocytes." Acta Histochem Suppl. (1990); 39: 339-334.
Kalli, et al., "Folate receptor alpha as a tumor target in epithelial ovarian cancer." Gynecol Oncol. (2008); 108(3): 619-626.
Kan and Dozy, "Antenatal diagnosis of sickle-cell anaemia by DNA analysis of amniotic-fluid cells." The Lancet (1978): 312 (8096): 910-912.
Kan and Dozy, "Polymorphism of DNA sequence adjacent to human β-globin structural gene: relationship to sickle mutation." PNAS (1978); 75(11): 5631-5635.
Kansas, et al., "Molecular mapping of functional domains of the leukocyte receptor for endothelium, LAM-1." J Cell Biol. (1991); 114(2): 351-358.
Kasinrerk, et al., "Human leukoctye activation antigen M6, a member of the Ig superfamily, is the species homologue of rat OX-47, mouse basigin, and chicken HT7 molecule." J Immunol. (1992); 149 (3): 847-854.
Kawanishi, et al., "Secreted CXCL1 is a Potential Mediator and Marker of the Tumor Invasion of Bladder Cancer." Clin Cancer Res (2008); 14 (9): 2579-2587.
Keller, et al., "CD24 is a marker of exosomes secreted into urine and amniotic fluid." Kidney Int. (2007); 72 (9): 1095-1102.
Kepley, et al., "Identification and partial characterization of a unique marker for human basophils." J Immunol (1995); 154 (12): 6548-6555.
Kim, et al., "The multidrug resistance transporte ABCG2 (breast cancer resistance protein 1) effluxes Hoechst 33342 and is overexpressed in hematopoietic stem cells." Clin Cancer Res. (2002); 8(1): 22-28.
Kobayashi, et al., "Expression of organic cation transporter OCTN1 in hematopoietic cells during erythroid differentiation." Exp. Hematol. (2004); 32 (12): 1156-1162.
Koliha, et al., "A novel multiplex bead-based platform highlights the diversity of extracellular vesicles," Journal of Extracellular Vesicles (2016); 5: 29975, 15 pages; https://dx.doi.org/10.3402/jev.v5.29975.
Kojima and Kitamura, "A signal sequence trap based on a constitutively active cytokine receptor." Nat Biotechnol. (1999); 17 (5): 487-490.
Komminoth, et al., "Polysialic acid of the neural cell adhesion molecule distinguishes small cell lung carsinoma from carcinoids." Am J Pathol. (1991); 139 (2): 297-304.
Korkaya, et al., "HER2 regulates the mammary stem/progenitor cell population driving tumorigenesis and invasion." Oncogene (2008); 27 (47): 6120-6130.
Kwon, et al., "Transcription-based amplification system and detection of amplified human immunodeficiency virus type 1 with a bead-based sandwich hybridization format." Proc Natl Acad Sci U S A (1989); 86: 1173-1177.
Lai, et al., "Tissue distribution of restricted leukocyte common antigens. A comprehensive study with protein- and carbohydrate-specific CD45R antibodies." Lab Invest. (1991); 64 (6): 844-854.

(56) References Cited

OTHER PUBLICATIONS

Landegren, et al., "A ligase-mediated gene detection technique." Science (1988); 241 (4869): 1077-1080.
Lapidot, et al., "A cell initiating human acute myeloid leukaemia after transplantation into SCID mice." Nature (1994); 367 (6464): 645-648.
Laxman, et al., "A first-generation multiplex biomarker analysis of urine for the early detection of prostate cancer." Cancer Research (2008); 68: 645-649.
Lee, et al., "Tumor stem cells derived from glioblastomas cultured in bFGF and EGF more closely mirror the phenotype and genotype of primary tumors than do serum-cultured cell lines." Cancer Cell. (2006); 9 (5): 391-403.
Lee, et al., "Tight-Binding Inhibition of Angiogenin and Ribonuclease A by Placental Ribonecluase Inhibitor," Biochemistry (1989); 28(1): 255-230.
Lewis, et al., "An erythrocyte-specific protein that binds to the poly(dG) region of the chicken β-globin gene promoter." Genes & Dev. (1988); 2: 863-873.
Li, et al., "Evidence for mesenchymal-epithelial transition associated with mouse hepatic stem cell differentiation." PLoS One (2011); 6(2): e17092.
Li, et al., "Identification of pancreatic cancer stem cells." Cancer Res. (2007); 67 (3): 1030-1037.
Li, et al., "Replacing PCR with COLD-PCR enriches variant DNA sequences and redefines the sensitivity of genetic testing." Nature Medicine (2008); 14 (5): 579-584.
Lim amd Oh, "The role of CD24 in various human epithelial neoplasias." Pathol Res Pract. (2005); 201 (7): 479-486.
Liu, et al., "Analysis of gene expression and chemoresistance of CD133+ cancer stem cells in glioblastoma." Mol Cancer (2006); 5: 67.
Lu, et al., "Selection of potential markers for epithelial ovarian cancer with gene expression arrays and recursive descent partition analysis." Clin Cancer Res. (2004); 10 (10): 3291-3300.
Lunter, et al., "Activated leukocyte cell adhesion molecule (ALCAM/CD166/MEMD), a novel actor in invasive growth, controls matrix metalloproteinase activity." Cancer Res. (2005); 65 (19): 8801-8808.
Luo, et al., "Prognostic value of human kallikrein 10 expression in epithelial ovarian carcinoma." Clin Cancer Res. (2001); 7 (8): 2372-2379.
Maglara, et al., "The combination of human glandular kallikrein and free prostate-specific antigen (PSA) enhances discrimination between prostate cancer and benign prostatic hyperplasia in patients with moderately increased total PSA." Clin Chem. (1999); 45 (11): 1960-1966.
Margo, et al., "Proteomic and postproteomic characterization of keratan sulfate-glycanted isoforms of thyroglobulin and transferrin uniquely elaborated by papillary thyroid carcinomas." Am J Pathol. (2003); 163 (1): 183-196.
Marafioti, et al., "Leukocyte-specific phosphoprotein-1 and PU.1: two useful markers for distinguishing T-cell-rich B-cell lymphoma from lymphocyte-predominat Hodgkin's disease." Haematologica (2004); 89 (8): 957-964.
Masuoka, et al., "Monoclonal antibodies to feline lymphocyte membranes recognize the leukocyte-common antigen (CD45R)." J Vet Med Sci. (1992); 54: 865-870.
Matsui, et al., "CD64 on neutrophils is a sensitive and specific marker for detection of infection with rheumatoid arthritis." J Rheumatol. (2006); 33 (12): 2416-2424.
Matsui, et al., "Characterization of clonogenic multiple myeloma cells." Blood (2004); 103 (6): 2332-2336.
Matthews, et al., "Epithelial cell markers and proliferating cells in odontogenic jaw cysts." J Pathol. (1998); 156 (4): 283-190.
Mattick, J.S., "RNA regulation: a new genetics?" Nat Rev Genet. (2004); 5 (4): 316-323.
McGuckin, et al., "Prognostic significance of MUC1 epithelial mucin expression in breast cancer." Hum Pathol. (1995); 26 (4): 432-439.

Michie, et al., "Lifespan of human lymphocyte subsets defined by CD45 isoforms." Nature (1992); 360(6401): 264-265.
Miele, et al., "Autocatalytic replication of a recombinant RNA." J Mol Biol. (1983); 171: 281-295.
Min-oo, et al., "Phenotypic expression of pyruvate kinase deficiency and protection against malaria mouse model." Genes Immun. (2004); 5 (3): 168-175.
Miranda, et al., "Nucleic acids within urinary exosomes/microvesicles are potential biomarkers for renal disease." Kidney International (2010); 78 (2): 191-199.
Monzani, et al., "Melanoma contains CD133 and ABCG2 positive cells with enhanced tumourigenic potential." Eur J Cancer (2007); 43 (5): 935-946.
Myers, et al., "Detection of single base substitution by ribonuclease cleavage at mismatches in RNA:DNA duplexes." Science (1985); 230 (4731): 1242-1246.
Nakazawa, et al., "UV and skin cancer: specific p53 gene mutation in normal skin as a biologically relevant exposure measurement." Proc Natl Acad Sci U S A. (1994); 91: 360-364.
Naundorf, et al., "In vitro and in vivo activity of MT201, a fully human monoclonal antibody for pancarcinoma treatment." Int J Cancer (2002); 100 (1):101-110.
Neve, et al., "A collection of breast cancer cell lines for the study of functionally distinct cancer subtypes." Cancer Cell (2006); 10 (6): 515-527.
Nilsson, et al., "Prostate cancer-derived urine exosome: a novel approach to biomarkers for prostate cancer." British Journal of Cancer (2009); 100: 1603-1607.
Nishitani, et al., "Fibroblast-specific protein 1 is a specific prognostic marker for renal survival in patients with IgAN." Kidney Int. (2005); 68 (3): 1078-1085.
Niv, Y., "MUC1 and colorectal cancer pathophysiology considerations." World J Gastroenterol. (2008); 14 (14): 2139-2141.
Nogués, et al., "Bovine pancreatic ribonuclease A as a model of an enzyme with multiple substrates binding sites." BBA (1995); 1235(1): 16-24.
Oberneder, et al., "A phase I study with adecatumumab, a human antibody directed against epithelial cell adhesion molecule, in hormone refractory prostate cancer patients." Eur J Cancer (2006); 42 (15): 2530-2538.
O'Brien, et al., "A human colon cancer cell capable of initiating tumour growth in immunodeficient mice." Nature (2007); 445 (7123): 106-110.
Oldenborg, et al., "Role of CD47 as a marker of self on red blood cells." Science (2000); 288 (5473): 2051-2054.
Orita, et al., "Detection of polymorphisms of human DNA by gel electrophoresis as single-strand conformation polymorphisms." PNAS (1989); 86 (8): 2766-2770.
Orozco and Lewis, "Flow cytometric analysis of circulating microparticles in plasma." Cytometry A (2010); 77A(6): 502-514.
Ottaiano, et al., "Inhibitory effects of anti-CXCR4 antibodies on human colon cancer cells." Cancer Immunol Immunother. (2005); 54 (8): 781-791. Epub Dec. 11, 2004.
Partin, et al., "Use of human glandular kallikrein 2 for the detection of prostate cancer: preliminary analysis." Urology (1999); 54 (5): 839-845.
Pelloski, et al., "Epidermal Growth Factor Receptor Variant III Status Defines Clinically Subtypes of Glioblastoma." Journal of Clinical Oncology (2007); 25 (16): 2288-2294.
Prince, et al., "Identification of a subpopulation of cells with cancer stem cell properties in head and neck squamous cell carcinoma." Proc Natl Acad Sci U S A. (2007); 104 (3): 973-978.
Prinetti, et al., "GM3 synthase overexpression results in reduced cell motility and in caveolin-1 upregulation in human ovarian carcinoma cells." Glycobiology (2010); 20 (1): 62-77. doi: 10.1093/glycob/cwp143. Epub Sep. 16, 2009.
Punnoose, et al., "Molecular Biomarker Analyses Using Circulating Tumor Cells." PloS One (2010); 5 (9): e12517.
Rabinowits, et al., "Exosomal MicroRNA: A Diagnostic Marker for Lung Cancer." Clinical Lung Cancer (2009); 10 (1): 42-46.
Rangel, et al., "Tight junction proteins claudin-3 and claudin-4 are frequently overexpressed in ovarian cancer but not in ovarian cystadenomas." Clin Cancer Res. (2003); 9 (7): 2567-2575.

(56) References Cited

OTHER PUBLICATIONS

Raposo, et al., "B lymphocytes secrete antigen-presenting vesicles." Journal of Experimental Medicine (1996); 183: 1161-1172.
Ricci-Vitiani, et al., "Identification and expansion of human colon-cancer-initiating cells." Nature (2007); 445 (7123):111-115. Epub Nov. 19, 2006.
Rittenhouse, et al., "Human Kallikrein 2 (hK2) and prostate-specific antigen (PSA): two closley related, but distinct, kallikreins in the prostate." Crit Rev Clin Lab Sci. (1998); 35 (4): 275-368.
Rosen, et al., "Potential markers tha complement expression of CA125 in epithelial ovarian cancer." Gynecol Oncol. (2005); 99(2): 267-277.
Ross, et al., "Correlation of primary tumor prostate-specific membrane antigen expression with disease recurrence in prostate cancer." Clin Cancer Res. (2003); 9 (17): 6357-6362.
Rudolph, et al., "Immunophenotyping of dermal spindle cell tumors: diagnostic value of monocyte marker Ki-M1p and histogenetic considerations." Am J Surg Pathol. (1997); 21 (7): 791-800.
Ruppert, et al., "IL-4 decreases the expression of the monocyte differentiation marker CD14, paralleled by an increasing accessory potency." Immunobiology (1991); 182 (5): 449-464.
Sagiv, et al., "CD24 is a new oncogene, early at the multistep process of colorectal carcinogenesis." Gastroenterology (2006); 131 (2): 630-639.
Sainte-Laudy and Belon, "Improvement of flow cytometric analysis of basophil activation inhibition by high histamine dilutions. A novel basophil specific marker: CD 203c." Homeopathy (2006); 95 (1); 3-8.
Salmaggi, et al., "Glioblastoma-derived tumorospheres identify a population of tumor stem-like cells with angiogenic potential and enhanced multidrug resistance phenotype." GLIA (2006); 54 (8): 850-860.
Santin, et al., "Trastuzumab treatment in patients with advanced or recurrent endometrial carcinoma overexpressing HER2/neu." Int J Gynaecol Obstet. (2008); 102 (2): 128-131.
Schatton, et al., "Identification of cells initiating human melanomas." Nature (2008); 451 (7176): 345-349.
Shan, et al., "Five monoclonal antibodies against glycophorin A of a human erythrocyte recognize glycoprotein of bovine erythrocyte." Hybridoman (1998); 17 (1): 55-62.
Shangguan, et al., "Cell-specific aptamer probes for membrane protein elucidation in cancer cells." Proteome Res. (2008); 7 (5): 2133-2139.
Sheu and Shih, "Clinical and biological significance of HLA-G expression in ovarian cancer." Semin Cancer Biol. (2007); 17 (6):436-443.
Shih and Davidson, "Pathogenesis of ovarian cancer: clues from selected overexpressed genes." Future Oncol. (2009); 5 (10):1641-1657.
Shmelkov, et al., "CD133 expression is not restricted to stem cells, and both CD133+ and CD133-metastatic colon cancer cells initiate tumors." J Clin Invest. (2008); 118 (6): 2112-2120.
Siegel, et al., "Induction of mesenchymal/epithelial marker expression in human amniotic fluid stem cells." Reprod Biomed Online (2009); 19 (6): 838-846.
Singh, et al., "Identification of a cancer stem cell in human brain tumors." Cancer Res. (2003); 63 (18): 5821-5828.
Singh, et al., "Identification of human brain tumour initiating cells." Nature (2004); 432 (7015): 396-401.
Skog, et al., "Glioblastoma microvesicles transprot RNA and Proteins that promote tumour growth and provide diagnostic biomarkers." Nature Cell Biology (2008); 10 (12): 1470-1476.
Smith, et al., "CD133/prominin-1 is a potential therapeutic target for antibody-drug conjugates in hepatocellular and gastric cancers." Br J Cancer (2008); 99 (1):100-109.
Spiekermann, et al., "Identification of the antigen recognized by the monoclonal antibody 31D8." Exp Hematol. (1996); 24 (3):453-458.
Steemers, et al., "Whole-genome genotyping with the single-base extension assay." Nature Methods (2006); 3: 31-33.

Stott, et al., "Isolation of circulating tumor cells using a microvortex-generating herringbone-chip." Proc Natl Acad Sci U S A. (2010); 107 (43): 18392-18397.
Strojnik, et al., "Neural stem cell markers, nestin and musashi proteins, in the progression of human glioma: correlation of nestin with prognosis of patient survival." Surg. Neurol. (2007); 68 (2): 133-143.
Strutz, et al., "Identification and characterization of fibroblast marker: FSP1." J Cell Biol. (1995); 130 (2): 393-405.
Sun, et al., "Skeletal Localization and Neutralization of the SDF-1(CXCL12)/CXCR4 Axis Blocks Prostate Cancer Metastasis and Growth in Osseous Sites In Vivo." J Bone Miner Res. (2005); 20 (2): 318-329. Epub Nov. 16, 2004.
SUPERase-IN Thermoscientific (Year: 2018), downloaded Aug. 1, 2018, https://www.thermofisher.com/order/catalog/product/AM2696.
Tao, et al., "The application of CD71 and Hoechst33258 to staining method for sorting fetal nucleated red blood cells in the peripheral blood of pregnant women." Zhonghua Yi Xue Yi Chuan Xue Za Zhi. (2000); 17 (5): 352-354 (with English Abstract).
Taylor and Gerçel-Taylor, "MicroRNA signatures of tumor-derived exosomes as diagnostic biomarkers of ovarian cancer." Gynecol Oncol. (2008); 110: 13-21.
Taylor and Gerçel-Taylor, "Tumour-derived exosomes and their role in cancer- associated T-cell signalling defects." British Journal of Cancer (2005); 92 (2): 305-311.
Taylor, et al., "Binding of Specific Peroxidase-labeled Antibody to Placental-type Phosphatase on Tumor-derived Membrane Fragments." Cancer Rsearch (1960); 40 (11): 4064-4069.
Taylor, et al., "Radial glia cells are candidate stem cells of ependymoma." Cancer Cell (2005); 8 (4): 323-335.
Taylor-Papadimitriou, et al., "MUC1 and cancer." Biochim Biophys Acta (1999); 1455 (2-3): 301-313.
Telen and Chasis, "Relationship of the human erythrocyte Wrb antigen to an interaction between glycophorin A and band 3." Blood (1990); 76 (4): 842-848.
Théry et al., "Isolation and characterization of exosomes from cell culture supernatants and biological fluids." Curr Protoc Cell Biol. (2006); Chapter 3: Unit 3 22.1-3.22.29.
Théry, et al., "Exosomes: composition, biogenesis and function." Nature Reviews Immunology (2002); 2 (8): 569-579.
Thibert, et al., "Increased platelet CD36 constitutes a common marker in myeloproliferative disorders." Br J Haematol. (1995); 91 (3): 618-624.
Thomas, et al., "Identification, characterization and utilization of tumor cell selectin ligands in the design of colon cancer diagnostics." Biorheology (2009); 46 (3): 207-225.
Ting, et al., "Aberrant Overexpression of Satellite Repeats in Pancreatic and Other Epithelial Cancers." Science (2011); 331 (6017): 593-596.
Todaro, et al., "Colon cancer stem cells dictate tumor growth and resist cell death by production of interleukin-4." Cell Stem Cell (2007); 1 (4): 389-402.
Tu, et al., "A functional role for circulating mouse L-selectin in regulating leukocyte/endothelial cell interactions in vivo." J Immunol. (2002); 169 (4): 2034-2043.
Uchida, et al., "Direct isolation of human central nervous systems stem cells." Proc Natl Acad Sci U S A. (2000); 97 (26): 14720-1725.
Valent, et al., "Further characterization of surface membrane structures expressed on human basophils and mast cells." Int Arch Allergy Appl Immunol. (1990); 91 (2): 198-203.
Van Der Vos, et al., "Brain Tumor Microvesicles: Insights into Intercellular Communication in the Nervous System." Cellular and Molecular Neurobiology (2011); 31 (6): 949-995.
Velculescu, et al., "Serial Analysis of Gene Expression." Science (1995); 270 (5235): 484-487.
Venturi, et al., "Leukocyte migration is regulated by L-selectin endoproteolytic release." Immunity (2003); 19 (5): 713-724.
Visintin, et al., "Diagnostic markers for early detection of ovarian cancer." Clin Cancer Res. (2008); 14 (4): 1065-1072.
Vlassov, et al., "Exosomes: Current knowledge of their composition, biological functions, and diagnostic and therapeutic potentials." Biochimica et Biophysica Acta (2012); 1820 (7): 940-948.

(56) References Cited

OTHER PUBLICATIONS

Walker, et al., "Growth factor receptor expression in anal squamous lesions: modifications associated with oncogenic human papillomavirus and human immunodeficiency virus." Hum Pathol. (2009); 40(11): 1517-1527.

Went, et al., "Frequent EpCam protein expression in human carcinomas." Hum Pathol. (2004); 35: 122-128.

Yang and Chang, "Bladder Cancer Initiating Cells (BCICs) Are Among EMA-CD44v6+ Subset: Novel Methods for Isolating Undetermined Cancer Stem (Initiating) Cells." Cancer Investigation (2008); 26 (7): 725-733.

Yang, et al., "Significance of CD90+ cancer stem cells in human liver cancer." Cancer Cell (2008); 13 (2): 153-166.

Yin and Llyod, "Molecular cloning of the CA125 ovarian cancer antigen: identification as a new mucin, MUC16" J Biol Chem. (2001); 276 (29): 27371-27375.

Yin, et al., "Ovarian cancer antigen CA125 is encoded by the MUC16 mucin gene." Int J Cancer (2002); 98 (5): 737-740.

Yokohama, et al., "Acute basophilic leukemia lacking basophil-specific antigens: the importance of cytokine receptor expression in differential diagnosis." Int J Hematol. (2002); 75 (3): 309-313.

Yousef, et al., "Human kallikrein 5: a potential novel serum biomarker for breast and ovarian cancer." Cancer Res. (2003); 63 (14): 3958-3965.

Yousef, et al., "Parallel overexpression of seven kallikrein genes in ovarian cancer." Cancer Res. (2003); 63 (9): 2223-2227.

Yuan, et al., "Isolation of cancer stem cells from adult glioblastoma multiforme." Oncogene (2004); 23 (58): 9392-9400.

Zeppernick, et al., "Stem cell marker CD133 affects clinical outcome in glioma patients." Clin Cancer Res. (2008); 14 (1): 123-129.

Zhong, et al., "Expression of CD147 is associated with prostate cancer progression." International Journal of Cancer (2012); 130 (2): 300-308.

Zhou, et al., "Collection, storage, preservation, and normalization of human urinary exosomes for biomarker discovery." Kidney Int. (2006); 69 (8): 1471-1476.

Zwicker, et al., "Tumor-derived tissue factor-bearing microparticles are associated with venous thromboembolic events in malignancy." Clin Cancer Res. (2009); 15 (22): 6830-6840.

Scuderi, et al., Alternative splicing generates different parkin protein isoforms: evidences in human, rat, and mouse brain, BioMed Research International, Dec. 31, 2014, 14 pages.

* cited by examiner

FIG. 2A
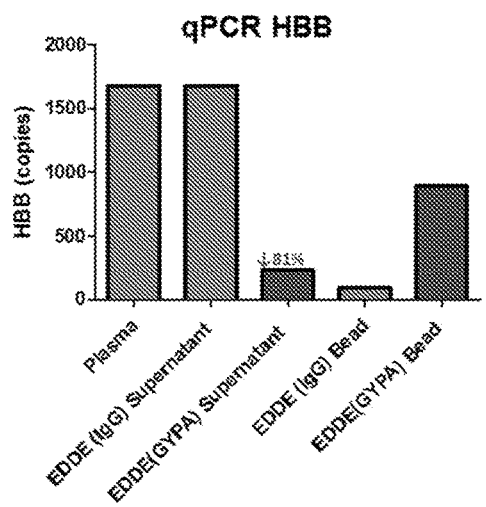
FIG. 2B
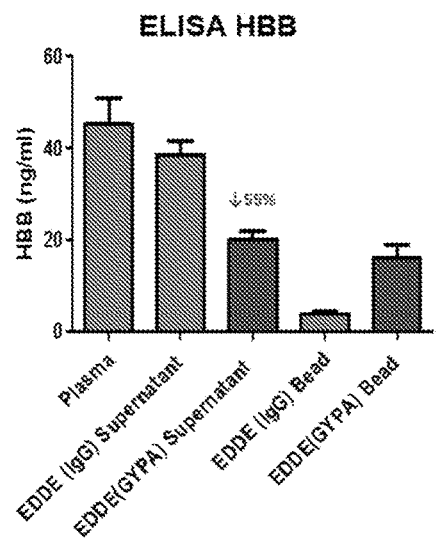
FIG. 2C
| gene symbol | EDDE (GYPA) Supernatant (TPM) | EDDE (IgG) Supernatant (TPM) | plasma (TPM) | reduction |
|---|---|---|---|---|
| HBA1 | 3998.8 | 10895.7 | 13110.4 | 63.3% |
| HBB | 3703.5 | 11382.8 | 10923.6 | 67.5% |
| HBA2 | 2858.3 | 8400.2 | 7877.3 | 66.0% |

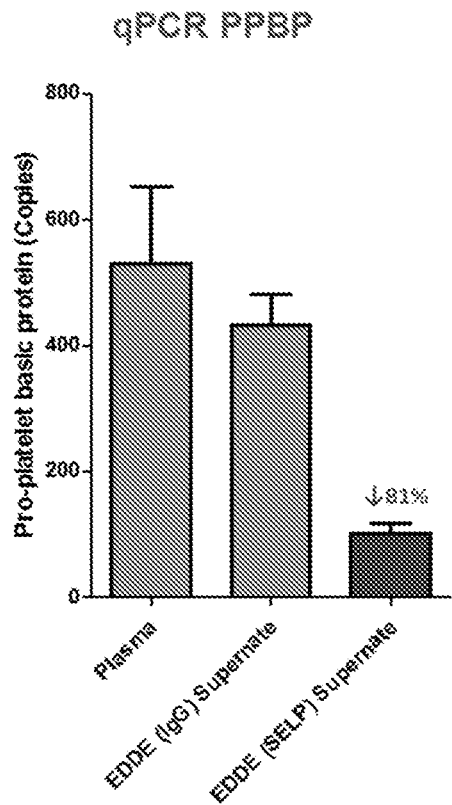
FIG. 3A
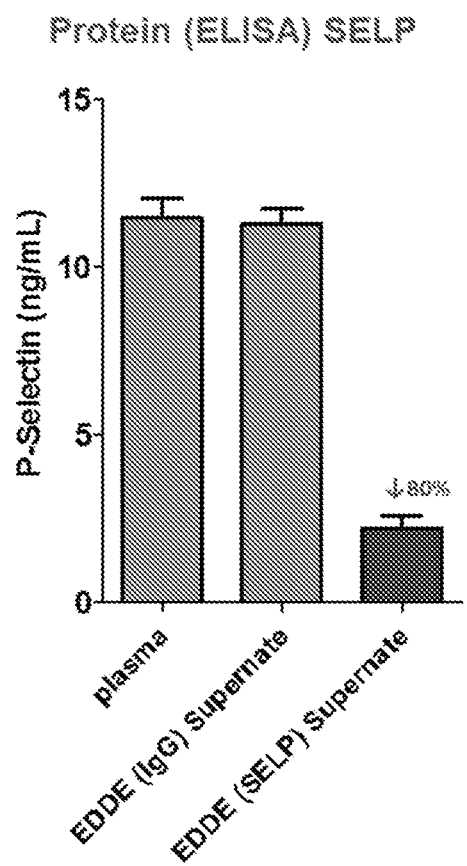
FIG. 3B
FIGURE 3C
| gene symbol | EDDE (SELP) Supernatant (TPM) | EDDE (IgG) Supernatant (TPM) | plasma (TPM) | reduction |
|---|---|---|---|---|
| PPBP | 73.2 | 203.5 | 204.8 | 64.0% |
| PF4V1 | 0.2 | 30.7 | 32.2 | 99.3% |
| PF4 | 26.5 | 66.1 | 65.3 | 59.9% |

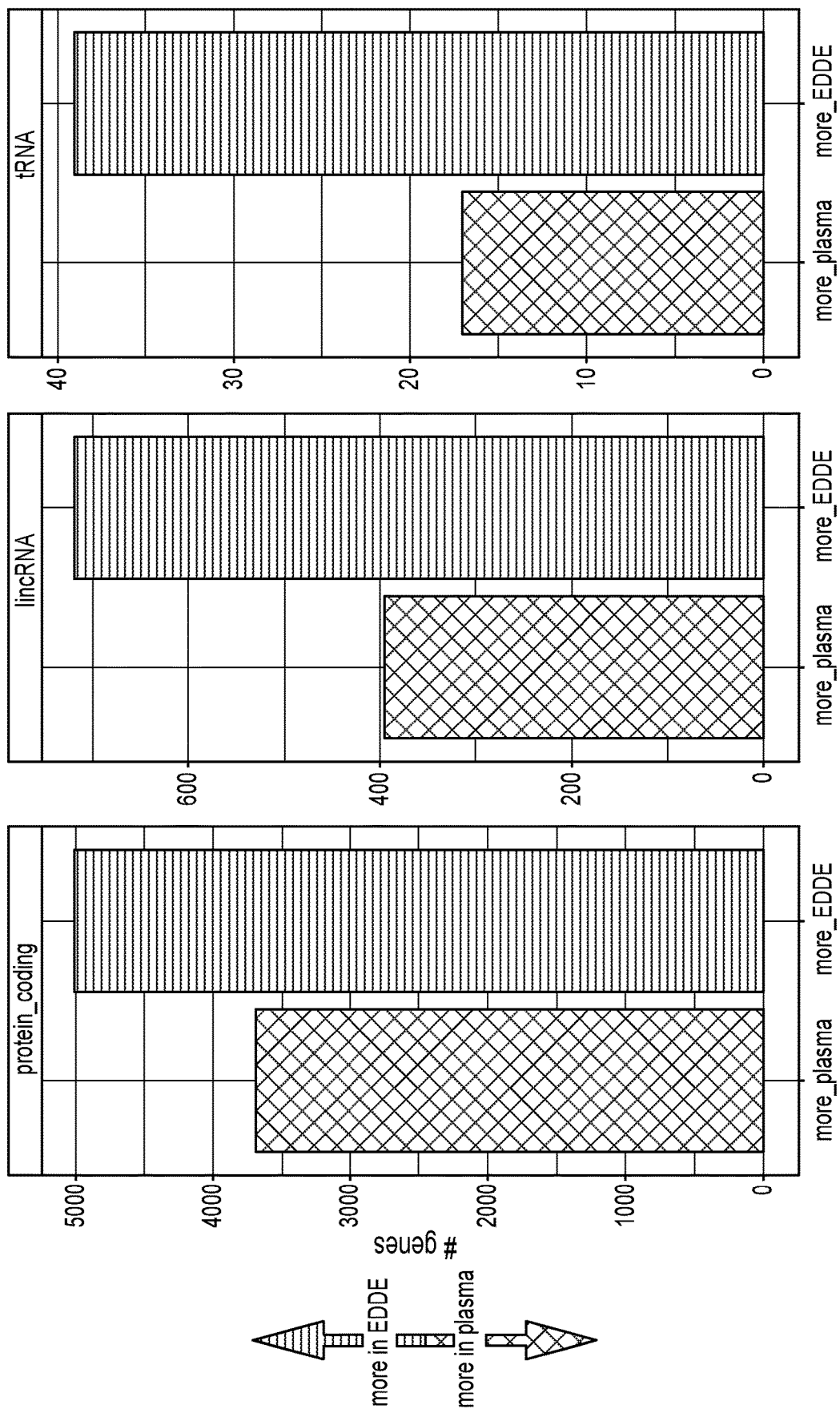

FIG. 4B

| gene symbol | gene biotype | TPM: EDDE GYPA_ supernatant | TPM:total _plasma | log2(fold change) | adj. pValue |
|---|---|---|---|---|---|
| DEFB112 | protein coding | 271.3 | 0 | 24.36 | 0.001274 |
| SLC30A7 | protein coding | 66.8 | 0 | 11.2 | 0.000288 |
| AKAP7 | protein coding | 58.7 | 0 | 10.76 | 0.008491 |
| PHOSPHO2 | protein coding | 31.7 | 0 | 9.54 | 0.079961 |
| IFI27L2 | protein coding | 31.7 | 0 | 8.95 | 0.068141 |
| PLA2G4A | protein coding | 24.1 | 0 | 11.4 | 0.000597 |
| DNAL1 | protein coding | 22.1 | 0 | 9.42 | 0.049058 |
| QDPR | protein coding | 22 | 0 | 9.48 | 0.022431 |
| CCNK | protein coding | 22 | 0 | 11.4 | 0.000597 |
| SAR1A | protein coding | 21.8 | 0 | 9.23 | 0.031319 |
| CTC-534A2.2 | protein coding | 19.5 | 0 | 10.19 | 0.0108 |
| IMMP2L | protein coding | 19.3 | 0 | 8.65 | 0.054552 |
| SELENOM | protein coding | 16.2 | 0 | 9.01 | 0.113729 |
| IFT46 | protein coding | 15.7 | 0 | 9.56 | 0.038011 |
| THTPA | protein coding | 15.4 | 0 | 23.39 | 0 |
| CCS | protein coding | 14.4 | 0 | 8.77 | 0.118884 |
| BDH2 | protein coding | 14.4 | 0 | 22.57 | 0.00398 |
| OR4C12 | protein coding | 14.1 | 0 | 9.24 | 0.173609 |
| KIFAP3 | protein coding | 13.7 | 0 | 8.89 | 0.05332 |
| ARMC1 | protein coding | 12.9 | 0 | 8.41 | 0.045909 |
| ZNF354C | protein coding | 12.8 | 0 | 9.15 | 0.044273 |
| RMND1 | protein coding | 12 | 0 | 8.97 | 0.043339 |
| RNASE9 | protein coding | 11.6 | 0 | 10.01 | 0.016656 |
| SDAD1 | protein coding | 10.7 | 0 | 8.24 | 0.044147 |
| KRBOX1 | protein coding | 10 | 0 | 8.6 | 0.033846 |

FIG. 4C

| gene symbol | gene biotype | TPM: EDDE CD235a_CD62_s upernatant | TPM: plasma | log2(fold change) | adj. pValue |
|---|---|---|---|---|---|
| DEFA1B | protein coding | 51.7 | 0 | 10.3 | 0.002324 |
| PPP1R14A | protein coding | 8.9 | 0 | 8.3 | 0.080002 |
| MTUS2 | protein coding | 6.2 | 0 | 9.57 | 0.014737 |
| SUOX | protein coding | 6.1 | 0 | 9.61 | 0.021261 |
| ZNF670 | protein coding | 5.7 | 0 | 8.13 | 0.085675 |
| ZWINT | protein coding | 4.8 | 0 | 8.87 | 0.062269 |
| IL1R2 | protein coding | 4.7 | 0 | 8.69 | 0.112943 |
| THAP3 | protein coding | 4.6 | 0 | 8.02 | 0.070735 |
| ASAH2B | protein coding | 3.8 | 0 | 7.37 | 0.08019 |
| PRUNE2 | protein coding | 3.4 | 0 | 8.09 | 0.002953 |
| IFT22 | protein coding | 3.4 | 0 | 6.98 | 0.204447 |
| ZNF674 | protein coding | 2.9 | 0 | 9.14 | 0.027943 |
| NUPR1 | protein coding | 2.5 | 0 | 6.49 | 0.148668 |
| SULF1 | protein coding | 2.4 | 0 | 6.38 | 0.014146 |
| SLC35G1 | protein coding | 2.1 | 0 | 7.3 | 0.174377 |
| MFSD9 | protein coding | 2.1 | 0 | 6.27 | 0.146481 |
| AMT | protein coding | 2.1 | 0 | 6.72 | 0.259998 |
| NR2C1 | protein coding | 2 | 0 | 8.81 | 0.024947 |

6 of 10 most abundant genes are reduced >50% by EDDE

| Rank | Gene | TPM EDDE (GYPA+SELP) | TPM EDDE (IgG) | % depleted by EDDE |
|---|---|---|---|---|
| 1 | HBB | 5704.6 | 13602 | 58.06 |
| 2 | HBA1 | 1811 | 5051.9 | 64.15 |
| 3 | HBA2 | 773.4 | 2718.1 | 71.55 |
| 4 | TMSB4X | 1794.6 | 2044.6 | 12.23 |
| 5 | EEF1A1 | 1339.4 | 1611 | 16.86 |
| 6 | FTL | 1094 | 1500.9 | 27.11 |
| 7 | MT-ND1 | 494.4 | 1467.5 | 66.31 |
| 8 | MT-ND4L | 476.7 | 1216.4 | 60.81 |
| 9 | RPS27 | 1193.5 | 1154 | 0.00 |
| 10 | MT-CO1 | 441.3 | 999 | 55.83 |

FIG. 9 cont.

| Surface Protein Target | Cell target | Differential mRNA levels | Differential protein levels | Level of confidence N |
|---|---|---|---|---|
| CD235 (Glycophorin A) | Erythrocytes | HBB | | 20 |
| CD62 (P-selectin) | Platelet | PPBP | CD62 | 20 |
| CD171 (L1cam) | Neurons | NRGN | P-tau, tau, a-syn | 3 |
| CD44 | Cancer stem cells | GATA3, KRT19 | MET | 4 |
| CD184 | Breast cancer | GATA3, KRT19 | | 4 |
| CD42, Glycoprotein Ib and CD140, PDGFR | Platelet | PPBP | CD62 | 4 |
| CD233, SLC4A1 and CD240, RH | Erythrocytes | HBB | | 4 |

FIG. 11

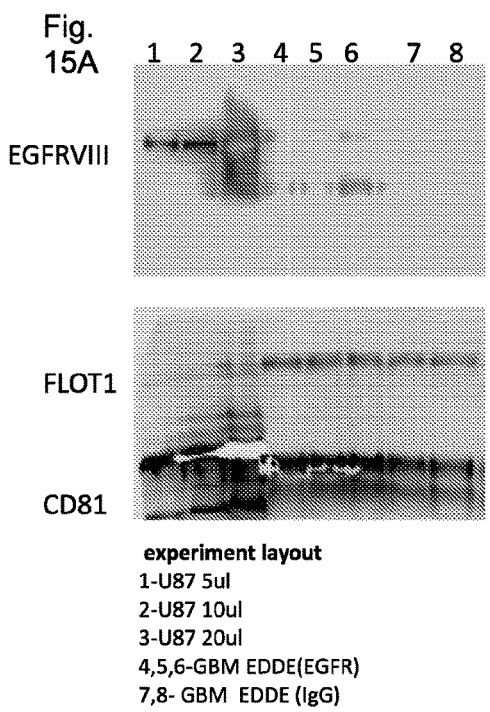
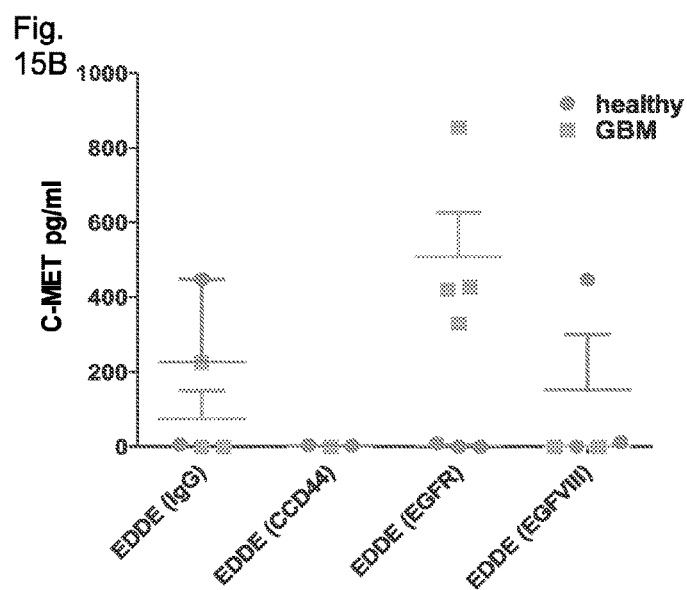
Fig. 15A
EGFRVIII
FLOT1
CD81
experiment layout
1-U87 5ul
2-U87 10ul
3-U87 20ul
4,5,6-GBM EDDE(EGFR)
7,8- GBM EDDE (IgG)
Fig. 15B

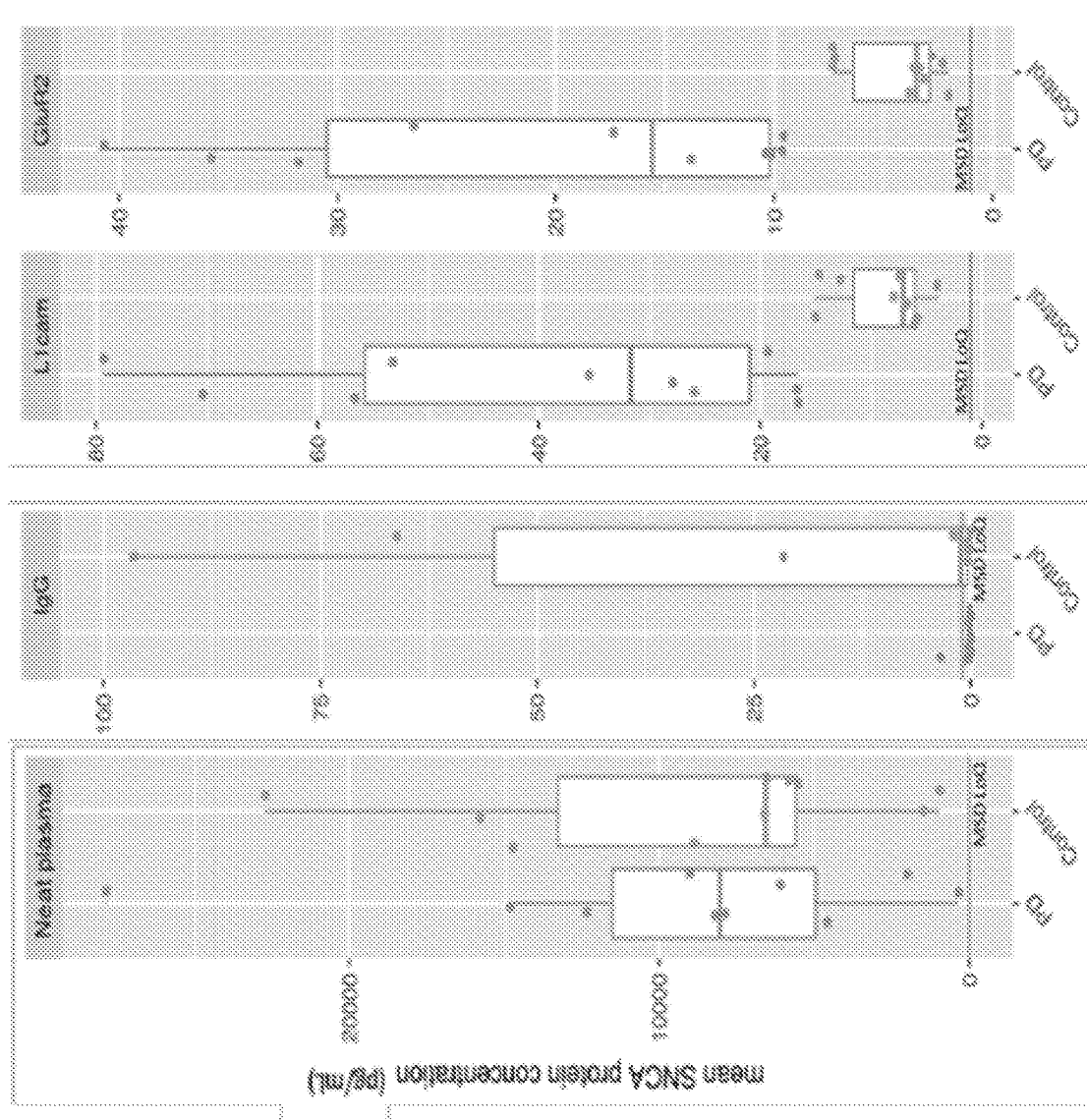

| isolation | PSD95 | NEFL |
|---|---|---|
| IgG | 1/10 | 1/10 |
| L1cam | 5/9 | 4/9 |
| GLUR2 | 7/8 | 5/8 |
| ExoLution | 3/4 | 3/4 |

Fig. 22B

TREATMENT AND DIAGNOSIS OF PARKINSON'S DISEASE USING ISOLATED AND ENRICHED POPULATIONS OF BIOFLUID-DERIVED EXTRACELLULAR VESICLES

CROSS-REFERENCE TO RELATED APPLICATIONS

This application is a U.S. National Phase application, filed under 35 U.S.C. 371, of International Application No. PCT/US2018/041884, filed on Jul. 12, 2018, which claims priority to and the benefit of U.S. Provisional Application Nos. 62/531,845, filed Jul. 12, 2017 and 62/678,853, filed May 31, 2018, which applications are herein incorporated by reference in their entireties.

BACKGROUND

Extracellular vesicles (EVs), e.g., exosomes and other microvesicles, are small, lipid bilayer-encapsulated microparticles released by cells into the extracellular environment. Extracellular vesicles are typically with diameter range in size from 30 nm to 10 microns. EVs are secreted from most if not all cell types and are found in body-fluids including plasma, serum, urine and cerebrospinal fluid. EVs serve as a natural vector for delivering macromolecules including protein, nucleic acids such as DNA and RNA, bioactive lipids and carbohydrates between cells. EVs signaling has been shown to play important roles in a wide range of physiological and pathological conditions including oncogenic disease, neurodegenerative disease, cardiovascular disease, autoimmune disease and metabolic disorders. EV surface contains markers (proteins/carbohydrates) inherited from the surface of the cell of origin allowing for the classification and targeting of cell and tissue-specific EVs. EV cargo (inclusive but not limited to proteins and RNA) depends on their cell of origin, the donor pathophysiological status, cellular conditions such as oxidative or metabolic stress as well as the donor responses to therapy interventions and therefore may serve as a source of biomarkers for specific body or disease conditions. Blood circulates throughout the body and is routinely collected in clinical practice, making it an ideal source of disease biomarkers. Serum and plasma, the liquid and cell-free phase of the blood, contains EVs as well as other particles, circulating free proteins, circulating free DNA and lipids. The abundance of certain components such as albumin and complement system in plasma sample make detecting rare metabolites and proteins particularly challenging. Protein detection is mostly based on antibody-antigen interaction, commonly referred to as immunoassay. This principle is used by traditional methods like gel electrophoresis (western blot), and enzyme-linked immunosorbent assay (ELISA) and Immuno-chemiluminescence as well as by newer digital methodology like Single Molecule Array (Simoa) and Erenna. Immunoassay performance depends on the quality (sensitivity and specificity) of the antibody, regardless of detection method. Antibody-antigen interaction properties depend on the antibody specificity and the environment of the interaction, which include: Buffer concentration of salt and proteins, pH and the availability of the antigen. Plasma and serum are rich in different components such as proteins and metabolites, and this complex milieu with abundant proteins is a poor environment for protein immunoassays, especially if the target analyte is less abundant. Using EVs overcomes this problem, since purification of EVs or a subpopulation of EVs will reduce the complexity of the sample and allow detection of low abundant targets or epitopes from the sample. Additionally, RNA in biofluids such as plasma or serum by nature is labile and subject to various types of RNase enzymes that digest it.

Currently EVs are isolated by ultracentrifugation with or without density gradient. While this process produces relatively pure EV population, it is labor intensive, inefficient and generates high sample to sample variability. Other methods include chemical precipitation, which co-isolates many non-vesicular components that can interfere in the detection assay. Isolation methods with low EV purity is therefore suboptimal for immunoassay methods as well as other detection methods. Moreover, these methods enrich many kinds of EVs that are found in the plasma, representing highly heterogeneous populations of EVs secreted from large variety of cell types. A large mixture of EV types from different cellular origins can interfere with immunoassays or over represent protein and RNA signatures from normal tissues and cells that mask profiles from disease EVs. For these reasons, a simple and reproducible method for isolating either the total EV population or the purification of a specific subpopulation of EVs can significantly enhance the detection of EV-associated protein and RNA based biomarkers.

Neurodegenerative diseases develop over decades and effective preventative therapy must begin before irreversible neuronal damage occurs. Unfortunately, neurodegenerative diseases are often not recognized until reaching late stages because diagnosis is based on clinical symptoms which do not manifest until significant neurological damage has already occurred. Verification of the diagnosis requires expensive bioimaging procedures and/or invasive studies on cerebrospinal fluid. Even so a definitive diagnosis is only possible by postmortem neuroanatomical and neurochemical analyses of brain tissue. The inability to medically intervene a neurodegenerative disease at a late stage is manifested in many remarkable drug trial failures, leading to no disease-modifying treatment yet for major neurodegenerative diseases such as Alzheimer's. EV-based biomarkers could potentially fill this gap to enable early detection, and non-invasive continuous monitoring even before the disease symptoms occur.

Therefore, there is a need in the art for accurate, safe, inexpensive and precise tests that can predict risk, identify diseases and monitor progression and responses to therapy of diseases at early stages, including for neurodegenerative diseases.

For the purpose of disclosure of the present invention, nucleic acids, proteins, lipids and carbohydrates are referred to as either in an isolated pure form (either in monomer or in oligomer) or in a complex(es) formed among these macromolecules. Additionally, EVs, exosomes, and microvesicles are used interchangeably in this disclosure.

SUMMARY OF THE INVENTION

The invention relates to a novel method of obtaining extracellular vesicles from a biological sample which can be used in providing prognosis, monitoring the effectiveness of a treatment and treatment response, and for use in patient stratification for clinical trials in a disease, including, but not limited to cancers, metabolic diseases, cardiovascular diseases, autoimmune, and neurodegenerative diseases. The invention further provides a method to identify useful biomarkers in these diseases.

In one aspect, the invention relates to a method comprising:
  a. contacting a biological sample with a functionalized capture surface under conditions sufficient to form a complex between the functionalized capture surface and at least one EV cell surface marker, wherein the capture surface is functionalized with a reagent that is specific for the at least one cell surface marker;
  b. separating the complex formed between the functionalized capture surface and the at least one cell surface marker from an unbound portion of the biological sample to obtain a captured complex, and retaining the captured complex;
  c. washing the captured complex formed between the functionalized capture surface and the at least one cell surface marker;
  d. enriching one or more subpopulations of EVs having at least one cell surface marker within the biological sample by repeating steps b.-c.; and,
  e. isolating and purifying one or more subpopulations of EVs having at least one target biomarker, performing the above a.-d. steps either sequentially or simultaneously if more than one cell surface marker is used.

In some embodiments, step e. comprises eluting the one or more subpopulations of EVs in an intact form. In some embodiments, step e. comprises lysing the one or more subpopulations of EVs and extracting at least one target biomarker. In some embodiments, the at least one biomarker comprise nucleic acid, protein, lipid, metabolite or a carbohydrate.

In a related aspect, the enrichment method further comprises the steps of:
  f. comparing the levels of at least one target biomarker from the isolated and purified subpopulation of EVs, from a subject and one or more pre-defined threshold(s); and,
  g. identifying the subject as having a disease or condition; and/or identifying a risk of disease progression in the subject; and/or identifying the subject as being suitable for a therapy if the levels of the at least one biomarker exceeds or differ from one or more pre-defined threshold(s).

In one aspect, the invention relates to a method comprising:
  a. contacting a biological sample with a functionalized capture surface under conditions sufficient to form a complex between the functionalized capture surface and at least one EV cell surface marker, wherein the functionalized capture surface comprises a reagent that is specific for the at least one cell surface marker;
  b. separating the complex formed between the functionalized capture surface and the at least one cell surface marker from an unbound portion of the biological sample and retaining the unbound portion;
  c. depleting one or more subpopulations of EVs having at least one cell surface marker from the biological sample, and performing steps a.-b. either sequentially or simultaneously if more than one cell surface marker is used, by retaining the unbound portion of the biological sample; and, optionally
  d. contacting the unbound portion with a second functionalized capture surface under conditions sufficient to form a complex between the second functionalized capture surface and at least one cell surface marker present in the unbound portion;
  e. enriching one or more subpopulations of EVs having at least one cell surface marker from the unbound portion of the biological sample, either sequentially or simultaneously with step d. if more than one cell surface marker is used; and,
  f. isolating and purifying one or more subpopulations of EVs having at least one target biomarker from the unbound portion of the biological sample.

EV surface contains markers (proteins/carbohydrates) inherited from the surface of the cell of origin allowing for the classification and targeting of cell and tissue-specific EVs. This is fundamental as when a complex is formed between capture material and an at least one cell surface marker provided herein, the complex formed contains exosomes.

With the encapsulation within EVs, RNA molecules are protected and therefore provide a unique class of biomarkers that reflect the disease/health state of the cells or tissues where EVs originate. Another characteristic that EVs carry from their cells/tissues of origin is the surface markers. Cell surface markers are typically membrane proteins expressed on the surface of cells that often conveniently serve as markers of specific cell types. For example, T cell and B cell surface markers identify their lineage and stage in the differentiation process. These lymphocytes differentiate into multiple cell subtypes and consequentially express different surface receptors or markers, which can be used to identify cellular subtypes, such as progenitor cells or terminally differentiated T helper cells. In cancer cells, oncogenic receptors especially the type of tyrosine kinases that many drugs successfully target against play key roles in the development and progression of many cancers, including but not limited to cMET, EGFR, VEGFR, NGFR. PDGFR, RET, ROS, and FGFR. These and other cell membrane markers carried on EV membranes could be taken advantage of for interrogating the state of cells/tissues of where EVs originate.

In one embodiment, EVs (especially exosomes) contain not only the RNA/protein cargo but also the surface features/proteins that are used in an enrichment/depletion process disclosed herein.

In some embodiments, the method comprises isolating total and subgroups of extracellular vesicles that express at least one cell surface marker, including, for example, exosomes and microvesicles, from biofluids in a way that is suitable for downstream specific proteins, DNA, RNA, lipids, metabolites and carbohydrate (e.g. lectins) detection. Examples of biofluids include plasma, serum, urine, saliva, seminal fluid and/or cerebrospinal fluid (CSF).

In some embodiments, the disclosure provides methods for isolating EVs from a biological sample following a depletion process, where non-relevant EVs are excluded from a biological sample based on the expression of one or more cell-surface markers.

In some embodiments, the disclosure also provides methods for enriching one or more subpopulations of EVs using a process disclosed herein based on the expression of cell-surface markers that may include proteins, lipids, or carbohydrates (sugars or oligosaccharides).

In some embodiments, the disclosure provides a method for isolating a purified population of EVs from a biological sample comprising: (a) providing a biological sample; (b) producing a functionalized capture surface (for example a plate or beads), wherein the capture surface is functionalized with a reagent that is specific for at least one cell surface marker; (c) contacting the biological sample with the functionalized capture surface under conditions sufficient to form a complex between the functionalized capture surface and the at least one cell-surface marker; (d) separating the complex formed between the functionalized capture surface and the at least one cell surface marker from the unbound portion(s) of the biological sample; and (e) isolating a purified population of EVs from the biological sample bound to the contact surface (i.e. —a captured complex) by performing an enrichment process, or isolating a purified population of EVs from the unbound portion of the biological sample by performing a depletion process.

In some embodiments, the depletion process comprises removing the complex formed between the reagent and the at least one cell-surface marker from the biological sample and retaining the unbound portion(s) of the biological sample.

In some embodiments, the depletion process is followed by contacting the unbound portion(s) of the biological sample with a capture surface under conditions sufficient to retain at least a portion of the EVs in the unbound portion(s) of the biological sample on or in the capture surface.

In one embodiment, the enrichment process comprises retaining the complex formed between the reagent and the at least one cell-surface marker from the biological sample.

In one embodiment, an enrichment process is exclusively performed, i.e. —it is not preceded by, not carried out concomitantly with, nor followed by a depletion process. In some embodiments, when a depletion process is first performed, the depletion process may be followed by an enrichment process. In other embodiments, a depletion process is performed in combination with an enrichment process.

In some embodiments, the method further comprises the step of extracting at least one biomarker from a subpopulation of EVs. In some embodiments, the biomarker is enclosed within the EVs. In other embodiments, the biomarker can include nucleic acid, proteins, lipids, metabolites and/or carbohydrates. In yet another embodiment, the biomarker is on the cell surface or the surface of EVs.

In some embodiments, the depletion process comprises removing the complex formed between the reagent and the at least one cell-surface marker from the biological sample and retaining the unbound portion(s) of the biological sample. In some embodiments, the depletion process is followed by contacting the unbound portion(s) of the biological sample with a capture surface under conditions sufficient to retain at least a portion of the EVs in the unbound portion(s) of the biological sample on or in the capture surface.

In some embodiments, the extracted nucleic acids are subject to further downstream analysis. Various nucleic acid sequencing techniques are used to detect and analyze nucleic acids such as cell free DNA and/or RNA extracted from the EV fraction from biological samples. Analysis of nucleic acids such as cell free DNA and/or nucleic acids extracted from EVs for diagnostic purposes has wide-ranging implications due to the non-invasive nature in which EVs can be easily collected.

In one aspect, the disclosure provides a method for isolating a purified total or subpopulation of EVs from a biological sample comprising:
  a. providing a biological sample;
  b. producing a functionalized capture surface, wherein the capture surface is functionalized with a reagent that is specific for at least one cell surface marker;
  c. contacting the biological sample with the functionalized capture surface under conditions sufficient to form a complex between the functionalized capture surface and the at least one cell-surface marker;
  d. separating the complex formed between the functionalized capture surface and the at least one cell surface marker from the unbound portion(s) of the biological sample to obtain a captured complex and either retaining the captured complex for an enrichment process or retaining the uncaptured portion(s) for a depletion process;
  e. performing an enrichment process or a depletion process; and,
  f. isolating and purifying a subpopulation of EVs from the biological sample.

In some embodiments, the depletion process comprises removing the complex formed between the reagent and the at least one cell-surface marker from the biological sample and retaining the unbound portion(s) of the biological sample including EVs.

In some embodiments, the depletion process is followed by contacting the unbound portion(s) of the biological sample with a capture surface under conditions sufficient to retain at least a portion of the EVs in the unbound portion(s) of the biological sample on or in the capture surface. In some embodiments, the method further comprises extracting one or more nucleic acids, proteins or lipids from the EVs. In some embodiments, the depletion process is followed by an enrichment process. In another embodiment, the depletion process is carried out in combination with an enrichment process. In some embodiments, the enrichment process comprises retaining the captured complex formed between the reagent and the at least one cell-surface marker from the biological sample.

In some embodiments, the enrichment process comprises retaining the captured complex formed between the reagent and the at least one cell-surface marker from the biological sample. In some embodiments, the method further comprises step extracting one or more nucleic acids, proteins, carbohydrates, or lipids from the EVs.

In some embodiments, the depletion process comprises removing the complex formed between the reagent and the at least one cell-surface marker from the biological sample and retaining the unbound portion(s) of the biological sample. In some embodiments, the depletion process is followed by contacting the unbound portion(s) of the biological sample with a capture surface under conditions sufficient to retain at least a portion of the EVs in the unbound portion(s) of the biological sample on or in the capture surface.

In some embodiments, the enrichment process comprises washing the functionalized capture surface that has been contacted with the biological sample.

In some embodiments, the isolating and purifying step disclosed herein comprises eluting the EVs in an intact form. In some embodiments, the isolating and purifying step disclosed herein comprises lysing the EVs and extracting one or more nucleic acids, proteins, carbohydrates or lipids from the lysed EVs.

In some embodiments, the reagent that is specific for at least one cell surface marker comprises one or more vitamin, protein, ligand, lectin, peptide, oligonucleotide, aptamer, and any combination thereof.

In some embodiments, the reagent that is specific for at least one cell surface marker selected from the group consisting of the markers shown in Tables 1A-1B and FIG. 11.

In another aspect, the invention relates to a method of identifying and isolating extracellular vesicles of neuronal origin in plasma samples based on their surface antigen decoration and then assaying the protein(s) and RNA cargo of the neuronal derived vesicles for the identification or prognosis of neurodegenerative disorders. The method can include early detection of subject risk for a neurodegenerative disorder, patient stratification for clinical enrollment or prediction or monitoring of treatment response.

In some embodiments, the assay comprises enriching neuronal derived exosomes (NDE) based on the presence of the neuronal marker GluR2 on the exosome surface and measuring different groups of biomarkers consisting of specific proteins, including α-synuclein, Tau, phosphorylated Tau, ubiquitinated proteins and synaptic proteins as well as mRNA of different disease-related genes to assess the level of one or more biomarkers associated with the GluR2 decorated exosomes. In some embodiments, the level of all RNA can be determined by RNAseq or any other transcriptome profiling methodology. The discovered RNA signature may either serve as a platform for further biomarker discovery, or guide medical intervention directly. In other embodiments, the GluR2 decorated exosomes' protein or lipid cargo can be characterized by different -omic methods including, but not limited to, mass-spectrometry and antibody array.

Various aspects and embodiments of the invention will now be described in detail. It will be appreciated that modification of the details may be made without departing from the scope of the invention. Further, unless otherwise required by context, singular terms shall include pluralities and plural terms shall include the singular.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representations as to the contents of these documents are based on the information available to the applicants and do not constitute any admission as to the correctness of the dates or contents of these documents.

BRIEF DESCRIPTION OF THE FIGURES

Any of the above aspects and embodiments can be combined with any other aspect or embodiment as disclosed here in the Summary and/or Detailed Description sections.

The patent or application file contains at least one drawing executed in color. Copies of this patent or patent application publication with color drawings will be provided by the Office upon request and payment of the necessary fee.

Figure 1:
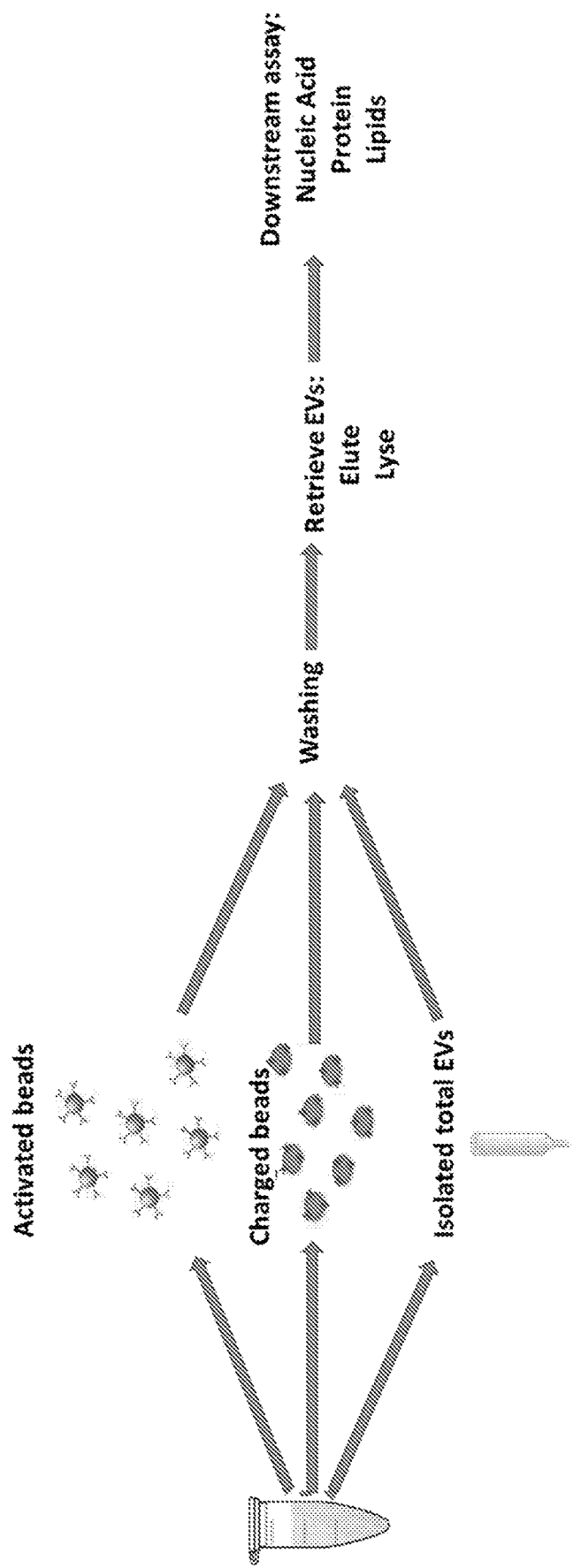

Various objects and advantages and a more complete understanding of the present invention are apparent and more readily appreciated by reference to the following Detailed Description and to the appended claims when taken in conjunction with the accompanying Drawing wherein:

FIG. 1 is an overview of the process with the three different variants of EV isolation.

FIGS. 2A and 2B are a series of graphs and FIG. 2C is a table depicting the ability of an anti-GYPA (CD235) antibody to deplete, erythrocyte and reticulocyte-derived EVs as measured by RNA and protein levels. The result of depleting reticulocyte and erythrocyte EVs is that the most abundant mRNAs in plasma (HBB, HBA1 and HBA2) are removed by over 60% as seen by RNASeq.

FIGS. 3A and 3B are a series of graphs and FIG. 3C is a table depicting the ability of an anti-SELP (CD62P) antibody to deplete platelet-derived EVs as measured by RNA and protein levels. The result of depleting platelet EVs is that platelet-associated mRNAs in plasma (PPBP, PF4V1, PF4) are removed by 60% to 99% as seen by RNASeq.

FIG. 4A is a graph depicting that depleting erythrocyte and platelet-derived EVs and increased coverage of protein coding, lncRNA and tRNA in RNAseq of EVs. FIGS. 4B and 4C are a series of tables depicting a representative number of the protein-coding genes that were detected in EVs following the EDDE process.

Figure 5:
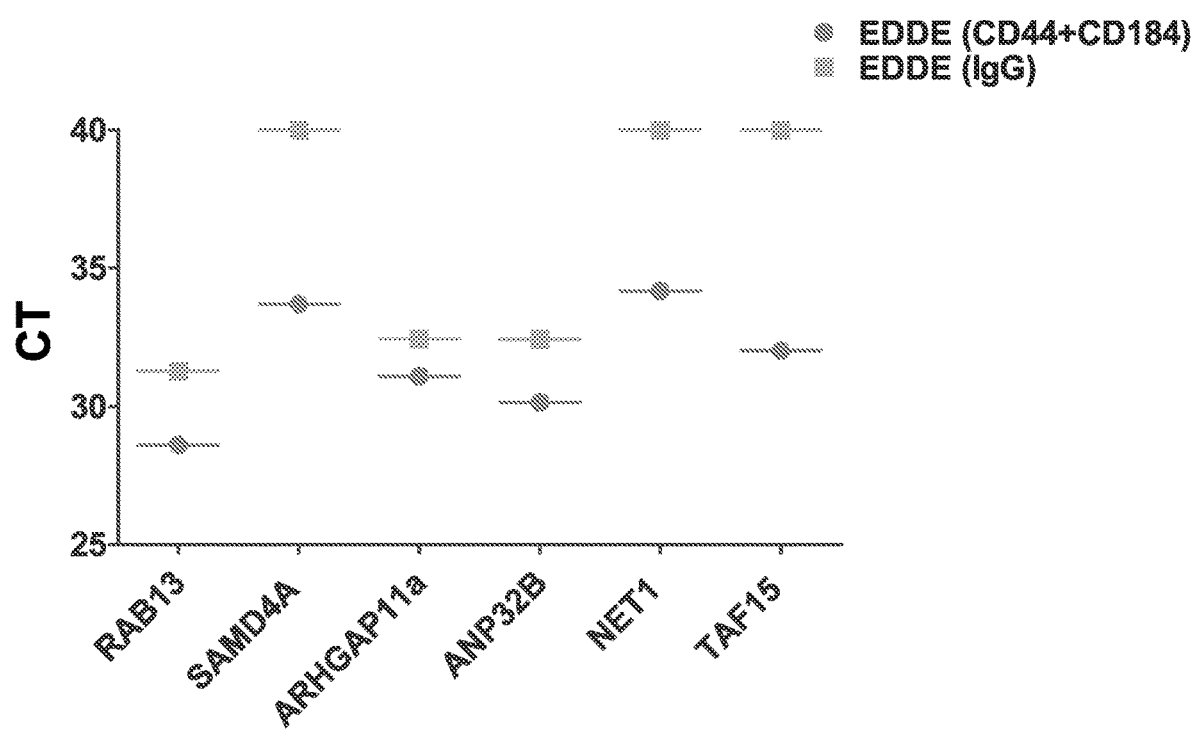

FIG. 5 is a graph depicting the ability of the EDDE process using anti-CD44 and anti-CD184 antibodies to capture breast cancer-derived EVs from samples.

Figure 6:
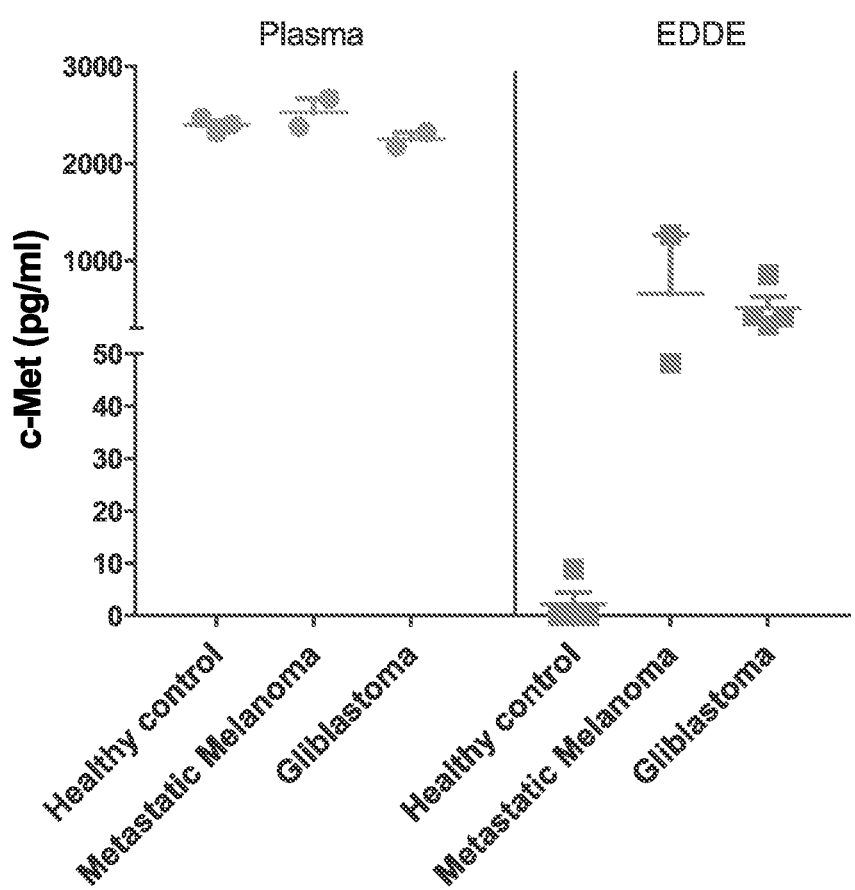

FIG. 6 is a series of graphs depicting the ability of the EDDE process to improve the specificity of an abundant biomarker.

FIGS. 7A, 7B, 7C, and 7D are a series of graphs depicting the use of the EDDE process to enrich for a subpopulation of EVs enabled the ability to measure previously undetectable proteins and RNA in plasma samples.

Figure 8:
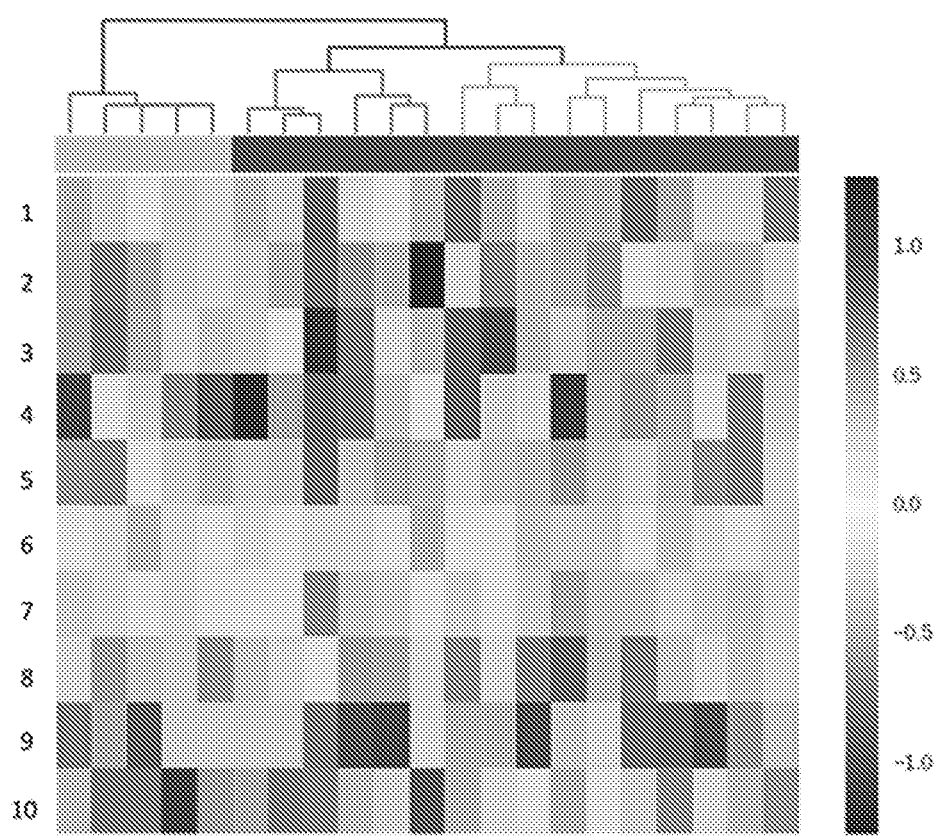

FIG. 8 is an illustration of the ability of the EDDE process to accurately distinguish patients who will respond to immunotherapy after only 2-4 weeks on ipilimumab using detected plasma RNA levels.

Figure 9:
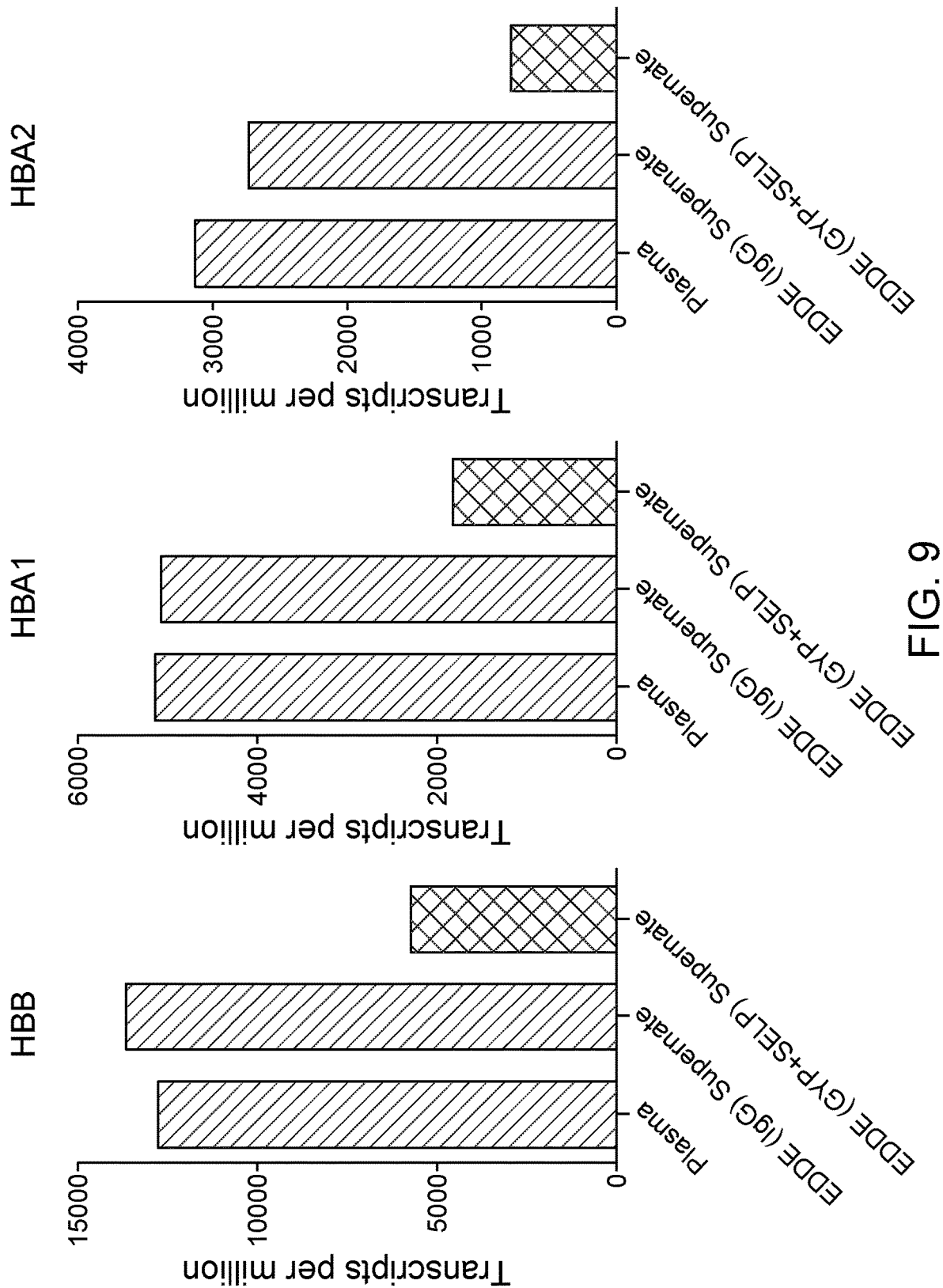

FIG. 9 illustrates the EDDE depletion result using an anti-GYPA (CD235) antibody to deplete erythrocyte and reticulocyte-derived EVs as measured by RNA levels. The result of EDDE depletion of reticulocyte and erythrocyte EVs is that the most abundant mRNAs in plasma (HBB, HBA1 and HBA2) were removed by over 50% as analyzed by RNASeq in transcripts per million measurements.

Figure 10:
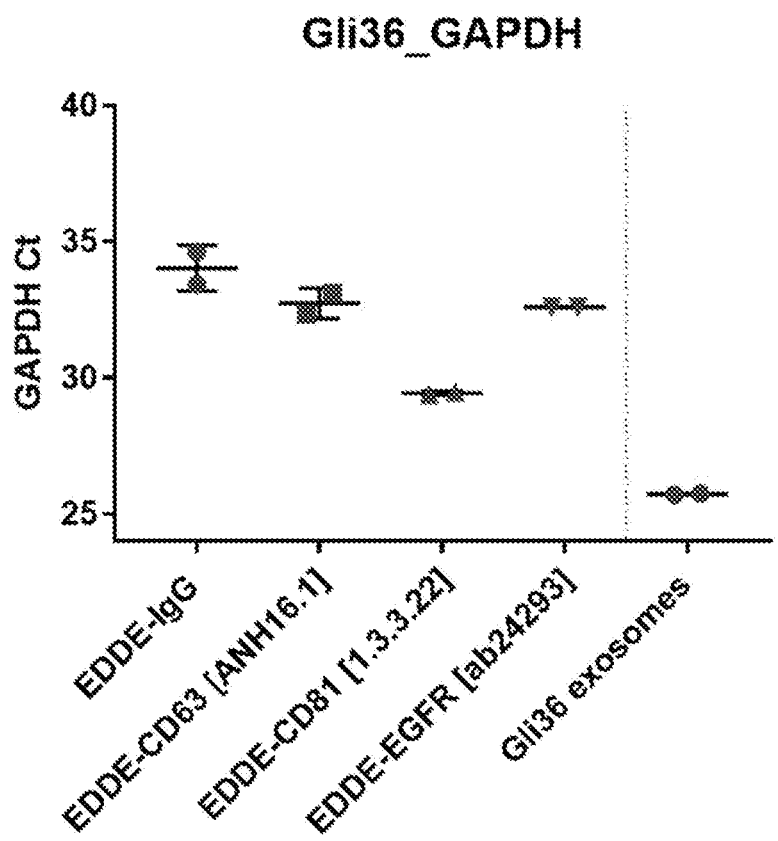

FIG. 10 illustrates the EDDE enrichment result using cell surface markers CD63, CD81 as well as glioblastoma cell line (Gli36) surface marker EGFR1, as demonstrated in increased amounts (in comparison to IgG controls) of GAPDH1 using qPCR, by way of enriching for specific subpopulations of EVs.

FIG. 11 illustrates a list summarizing potential cell surface proteins to be targeted with EDDE platform for either depletion or for enrichment purposes.

Figure 12B:
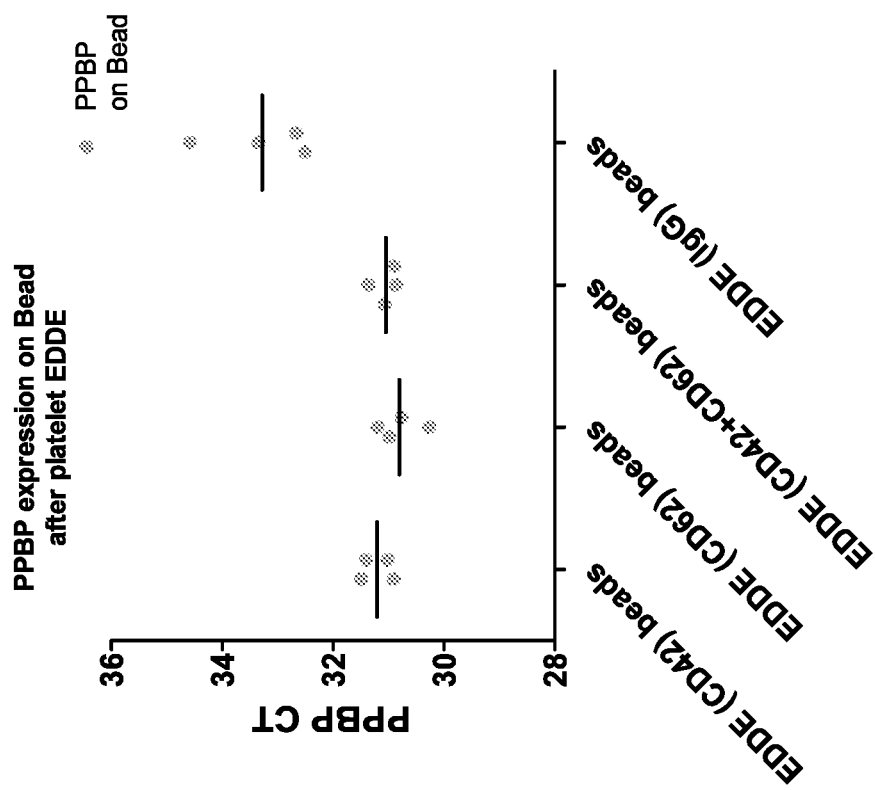
Figure 12A:
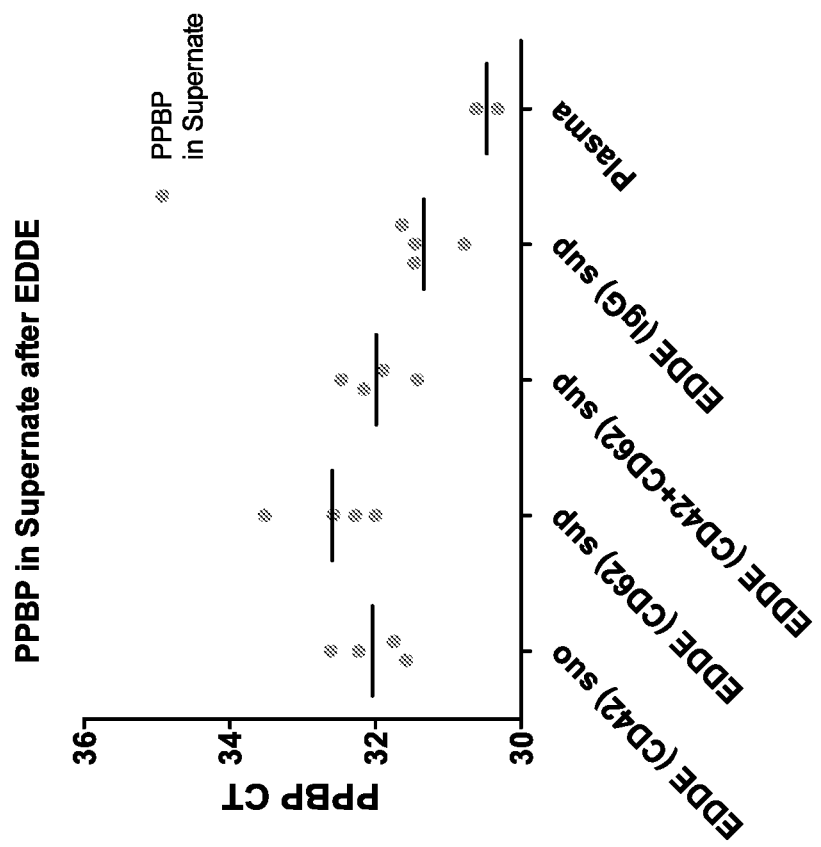

FIG. 12 summarizes the result of EDDE depletion using platelet surface markers CD42 and CD62 as demonstrated by increased amount (in comparison to control IgG) of platelet biomarker PPBP on the immune pulldown beads (FIG. 12A), but decreased amount in the plasma supernatant (the unbound portion) (FIG. 12B).

Figure 13:
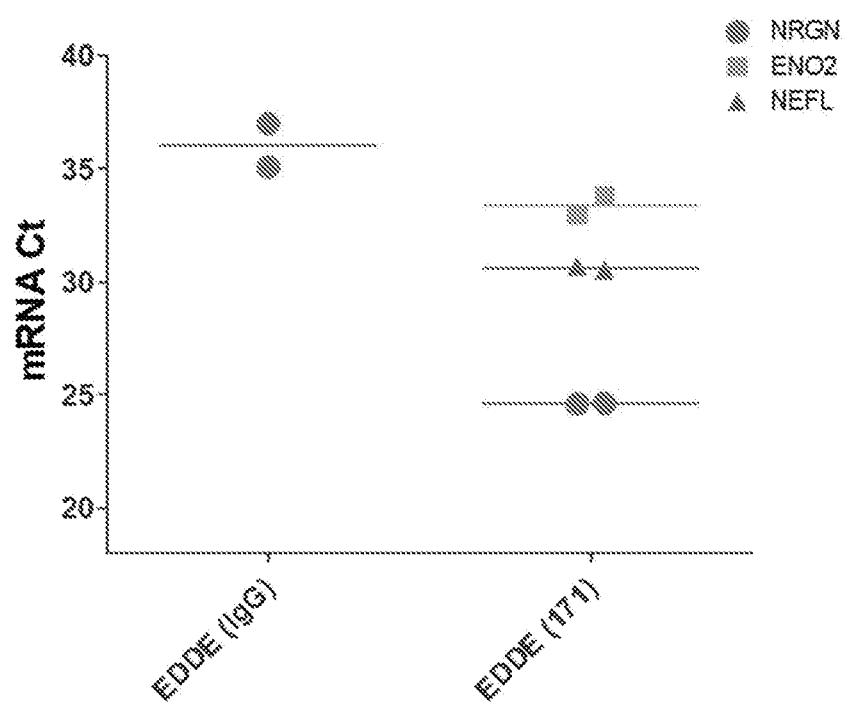

FIG. 13 illustrates the EDDE enrichment resulting in an increased abundance of neuronal genes analyzed by qPCR when using an anti-CD171 (L1CAM) antibody in comparison to an IgG control.

Figure 14:
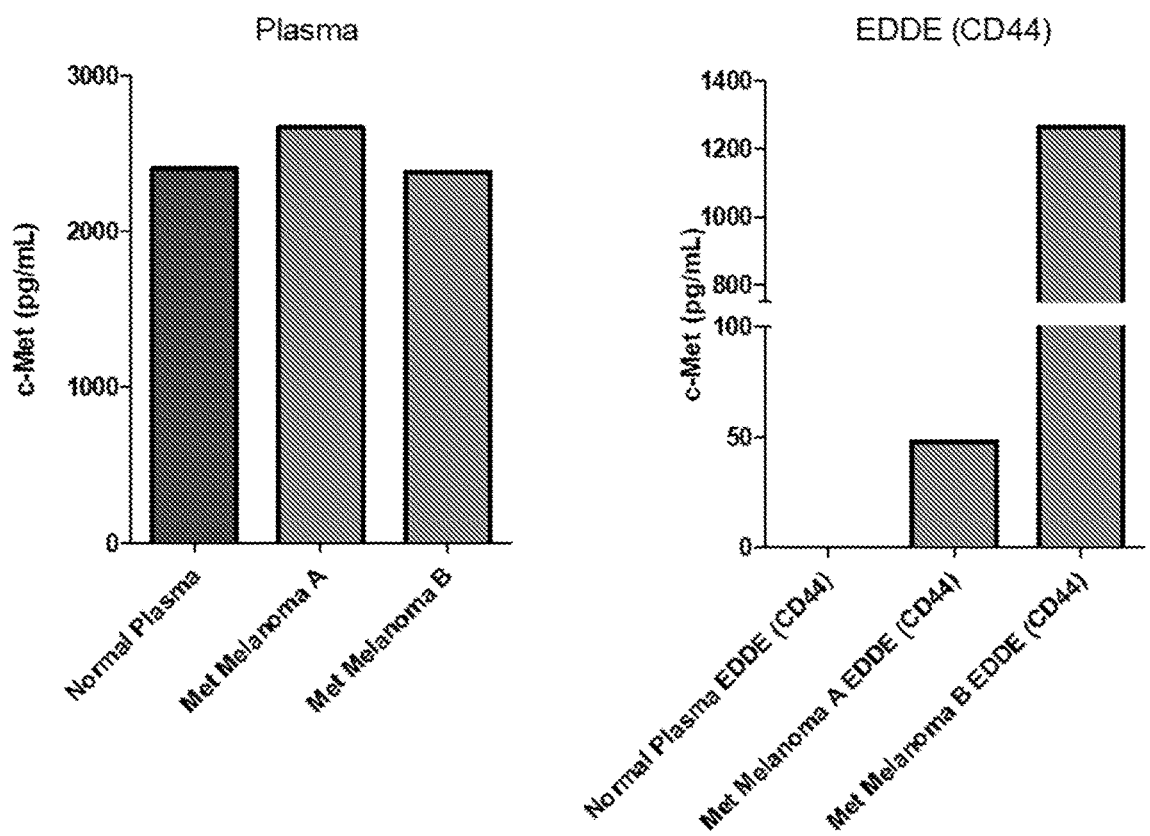

FIG. 14 illustrates the EDDE enrichment resulting in an increased abundance of melanoma surface protein marker cMET using anti-CD44 Ab, comparing plasma samples of normal and plasma samples from two melanoma patients (right part), clearly distinguishing melanoma from normal. The patients and the normal were otherwise indistinguishable by using plasma neat for cMET analysis if the EDDE enrichment was not performed (left part).

FIG. 15A is a western blot analysis of exosome-unique surface markers (FLOT1 and CD81) and cell surface marker EGFRvIII. FIG. 15B summarizes the result of EDDE enrichment of cMET protein biomarker from GBM patients in comparison to normal healthy using EGFR antibody, with IgG as a control. EGFRvIII EDDE did not enrich cMET in the same experiment since the patient does not express EGFRvIII surface marker.

Figure 16:
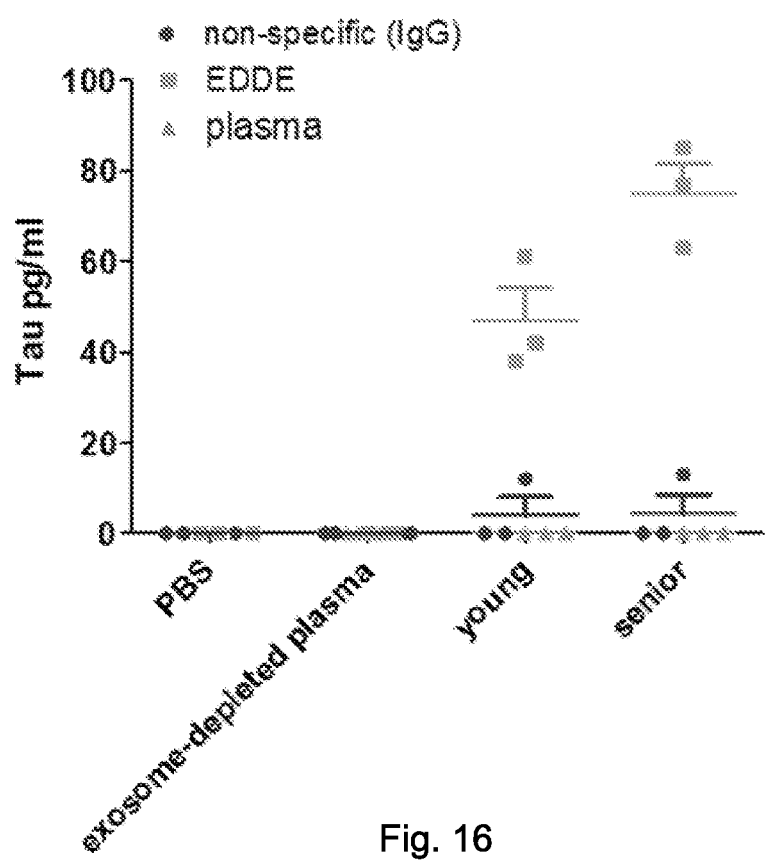

FIG. 16 illustrates elevated Tau protein biomarker in senior plasma in comparison to young plasma using L1CAM (CD171)-based EDDE enrichment process. As a control, the senior plasma was prior-depleted for EVs fraction through ultracentrifugation, which abolished the Tau signal even when EDDE enrichment was performed. PBS was another sample control for the EDDE process. In the absence of EDDE enrichment, the biomarker Tau protein level was undetectable in plasma neat in all samples.

Figure 17:
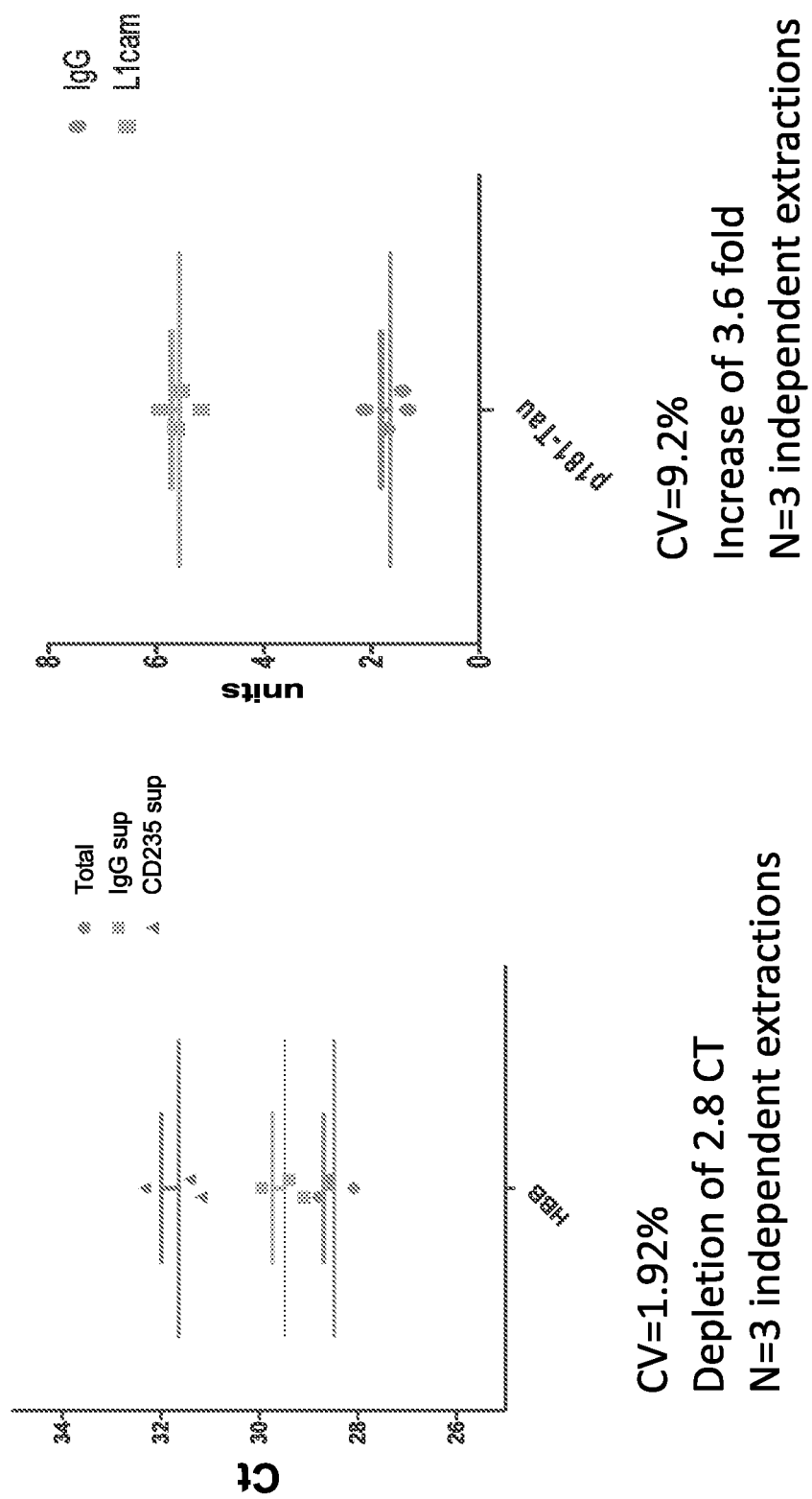

FIG. 17 illustrates the result of HBB gene analysis after EDDE depletion process using an anti-CD235 antibody (left part). More than 4-fold (2.8 Ct change) reduction of HBB gene level, as analyzed by qPCR in the EDDE supernatant (unbound portion), was observed when comparing CD235-based EDDE with IgG-based EDDE. The right part of the figure demonstrates 3.6-fold enrichment of p-181-Tau protein level in normal human plasma when L1CAM EDDE was performed (right part).

Figure 18A:
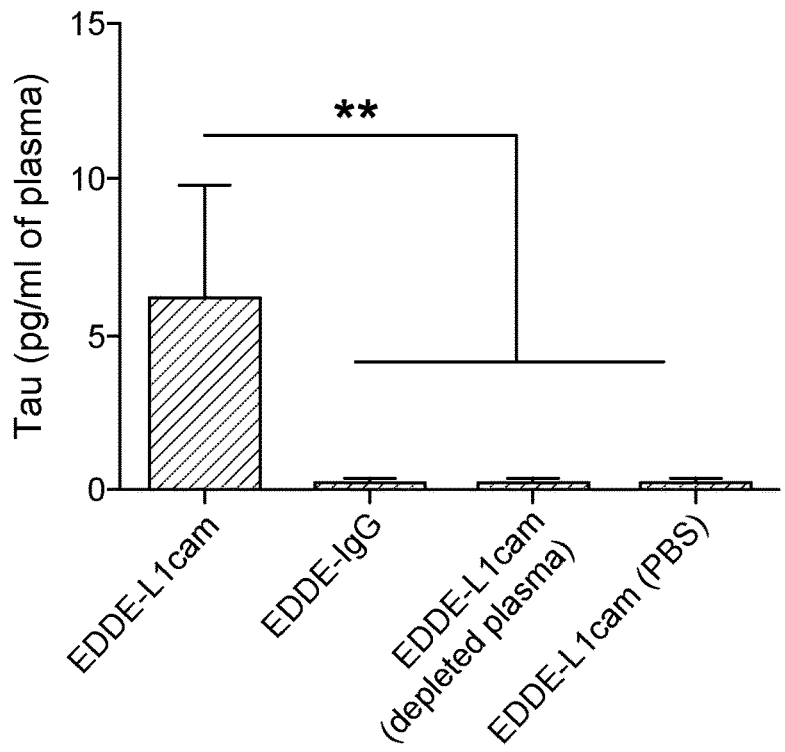
Figure 18B:
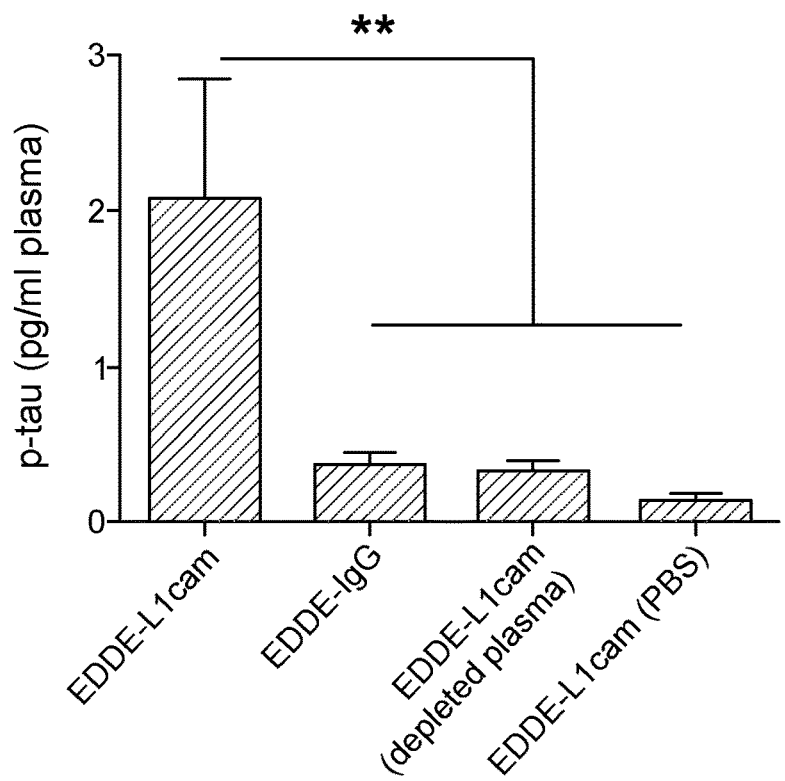
Figure 18C:
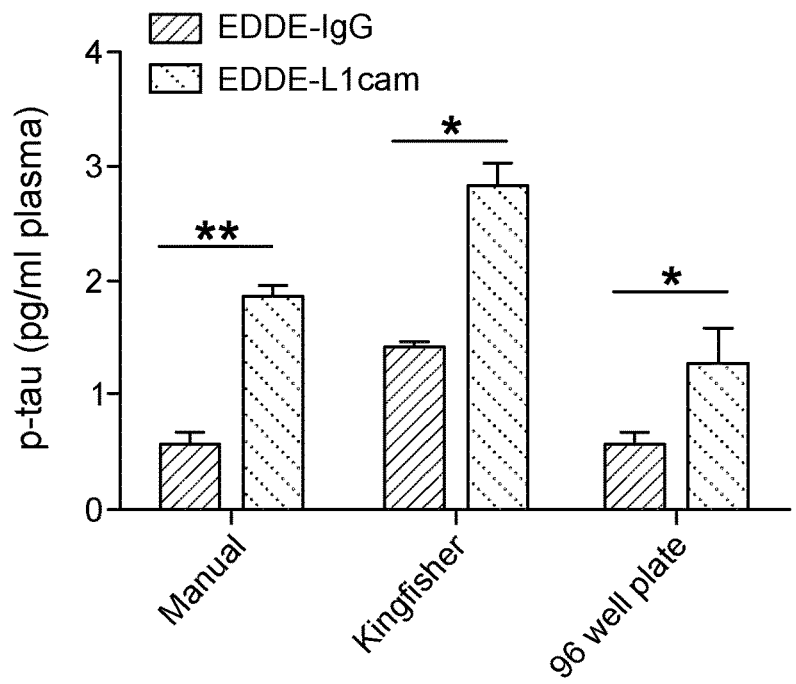
Figure 18D:
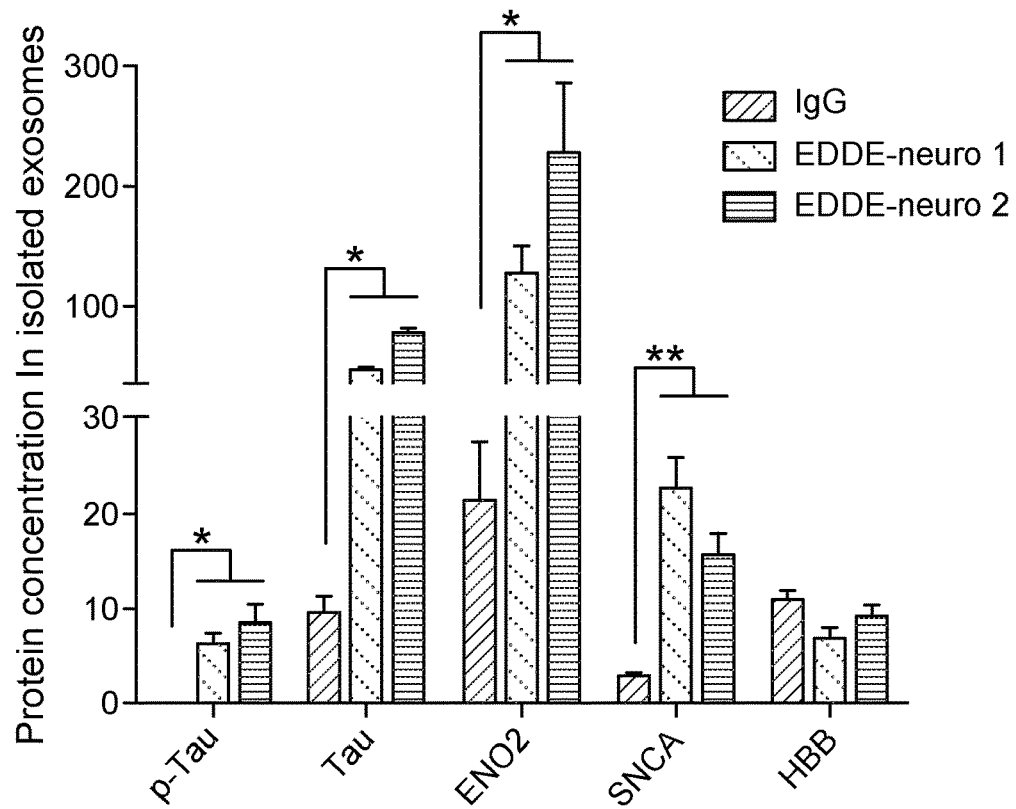

FIG. 18A-D illustrates the EDDE enrichment result for biomarkers Tau (FIG. 18A) and p-Tau (FIG. 18B) in human plasma using L1CAM cell surface marker, as controls, IgG EDDE, EDDE-L1CAM using PBS as sample, and EDDE-L1CAM using EV-depleted plasma samples were used. EDDE neuronal enrichment using L1CAM was compared for a manual process, a semi-automated process (King Fisher Flex), and a 96-well EDDE manual process (FIG. 18C). Neuronal biomarker protein levels for p-tau, Tau, ENO2, and SNCA were all enriched using L1CAM-EDDE (EDDE-neuro1) or GluR2-EDDE (EDDE-neuro2) platforms, in comparison to IgG-EDDE. As a control, non-neuronal biomarker protein HBB was not enriched using neuronal-specific EDDE processes (FIG. 18D).

Figure 19A:
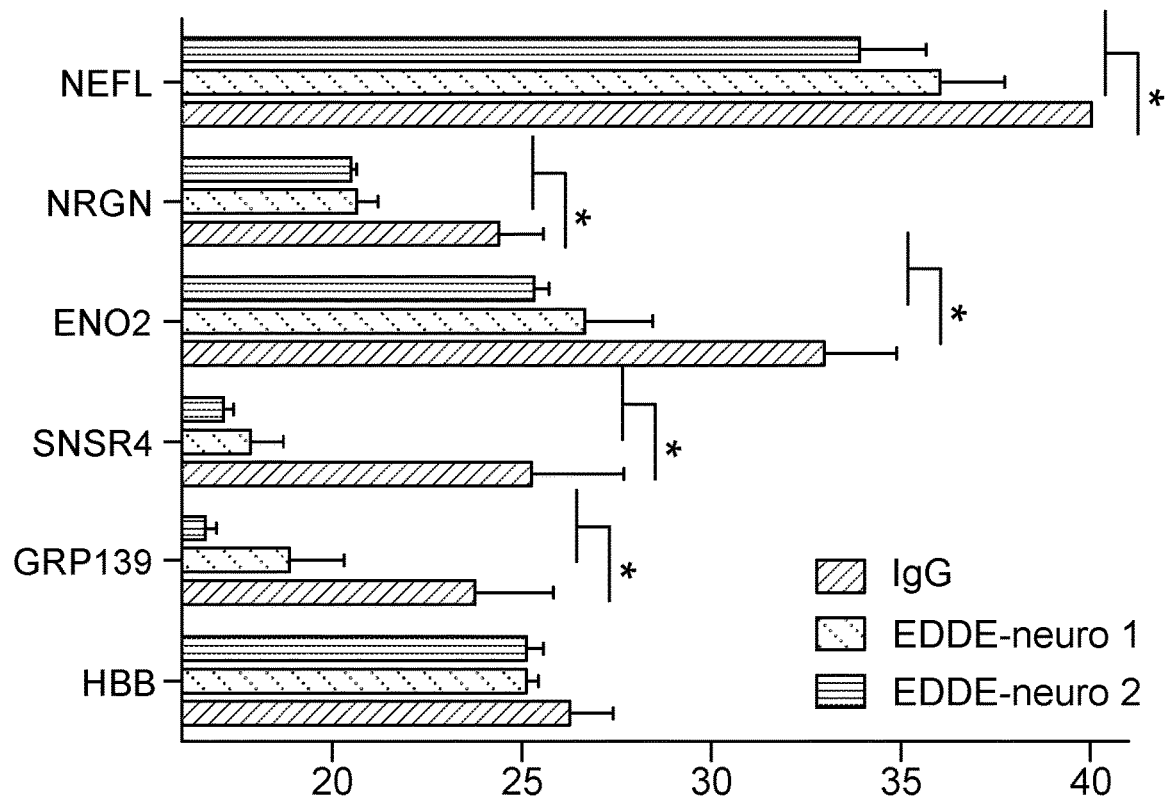
Figure 19B:
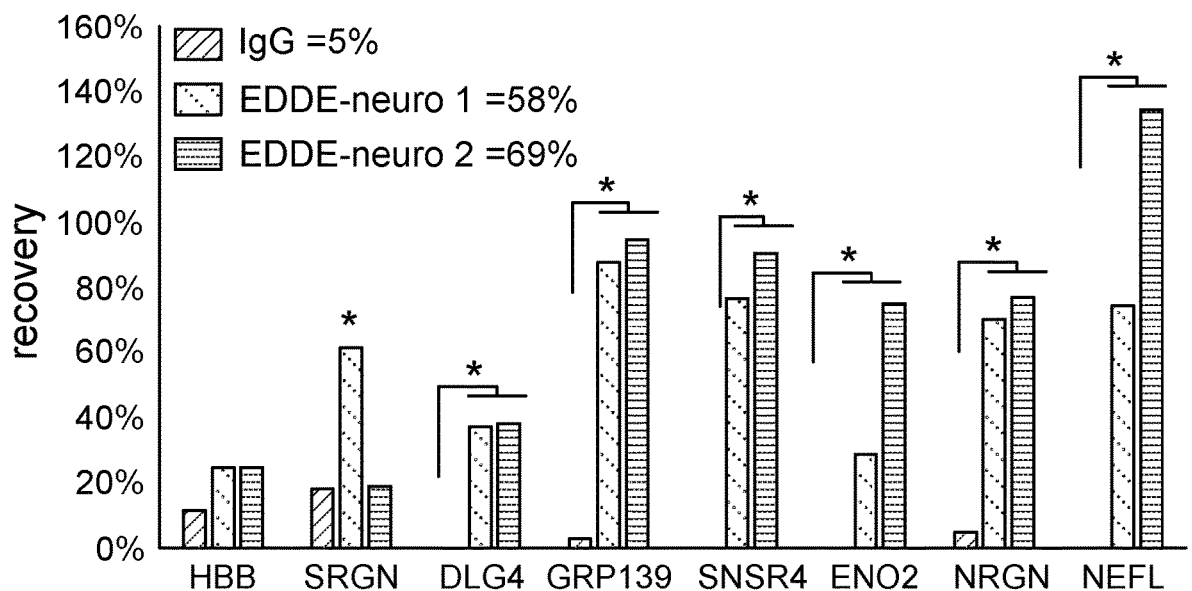
Figure 19C:
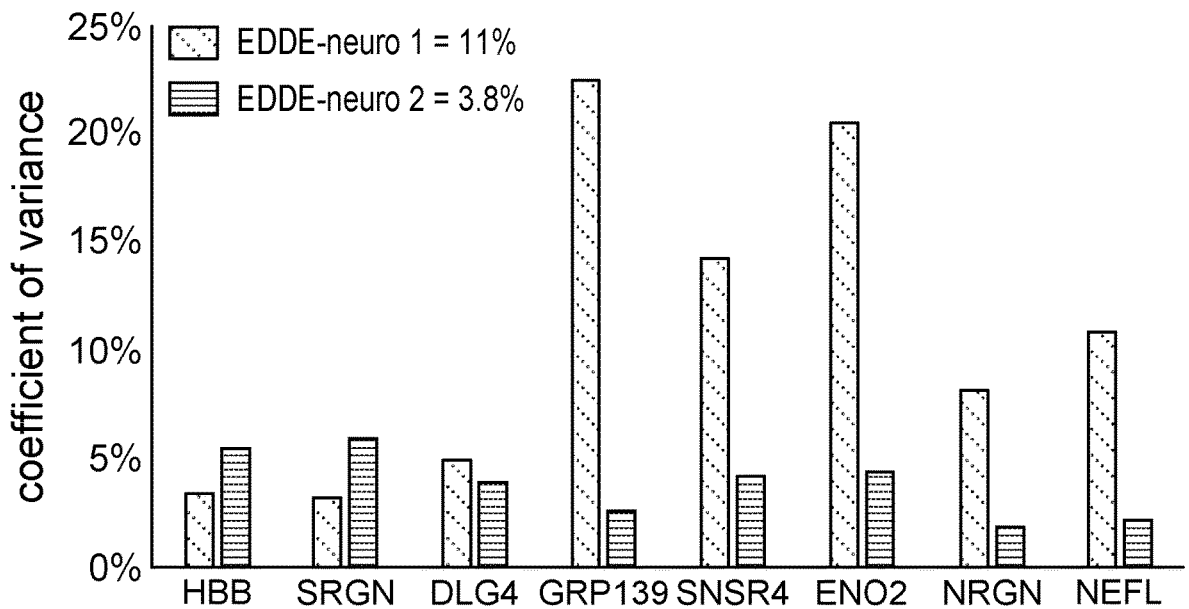
Figure 19D:
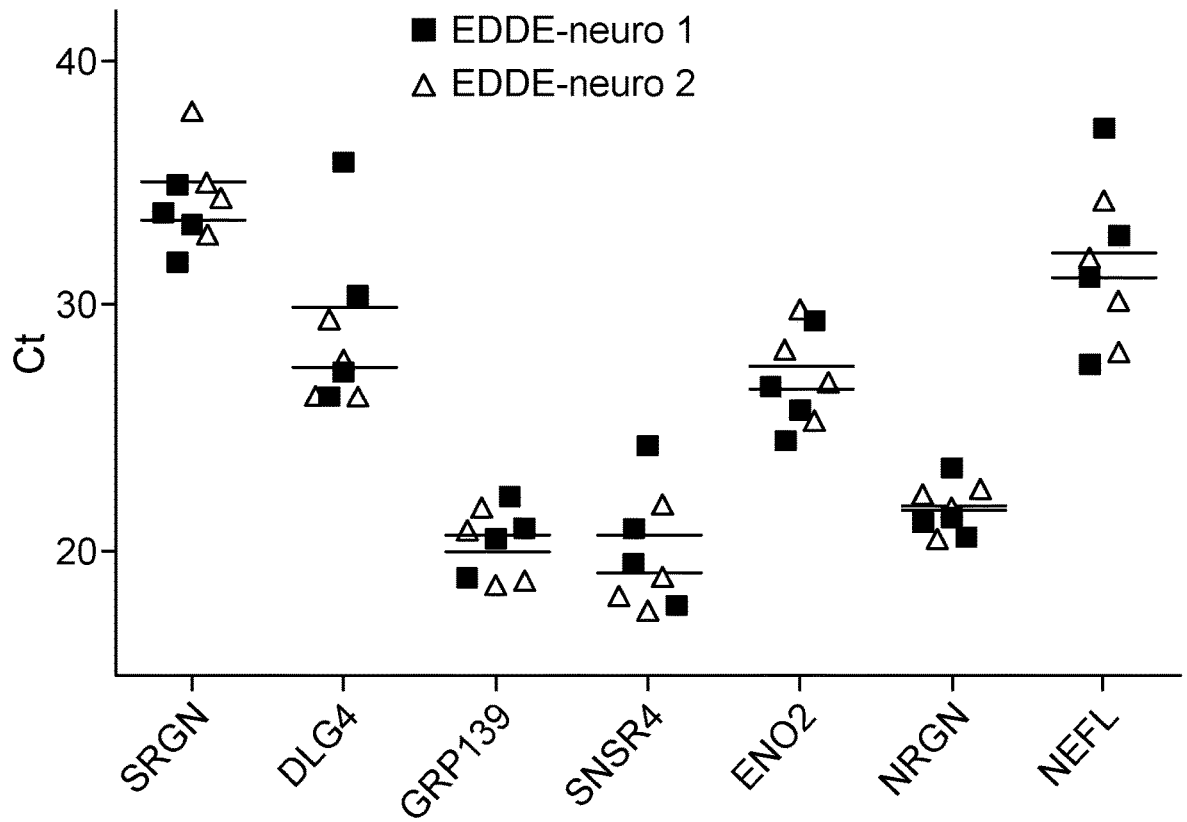

FIG. 19A-D illustrates the EDDE enrichment result for neuronal-specific gene biomarkers NEFL, NRGN, ENO2, SNSR4 and GRP139 (FIG. 19A) in human plasma using L1CAM-EDDE (EDDE-neuro1) or GluR2-EDDE (EDDE-neuro2) platforms. As controls, IgG EDDE was used. The qPCR analysis (Ct) was used to quantify the biomarkers (FIG. 19A), with recovery analysis in comparison to total EVs (FIG. 19B), coefficient of variance analysis (FIG. 19C), and raw Cts (FIG. 19D).

Figure 20A:
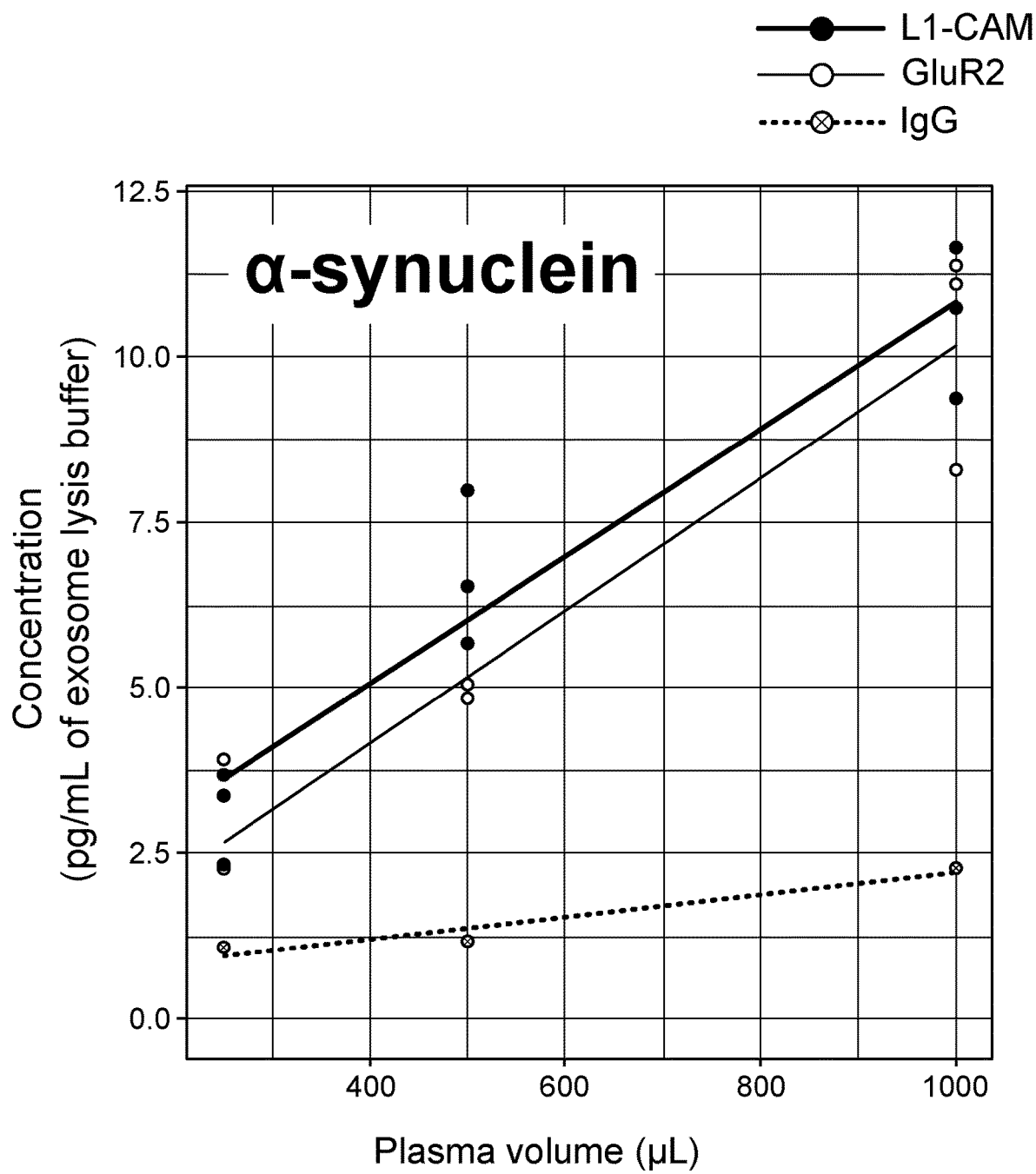
Figure 20B:
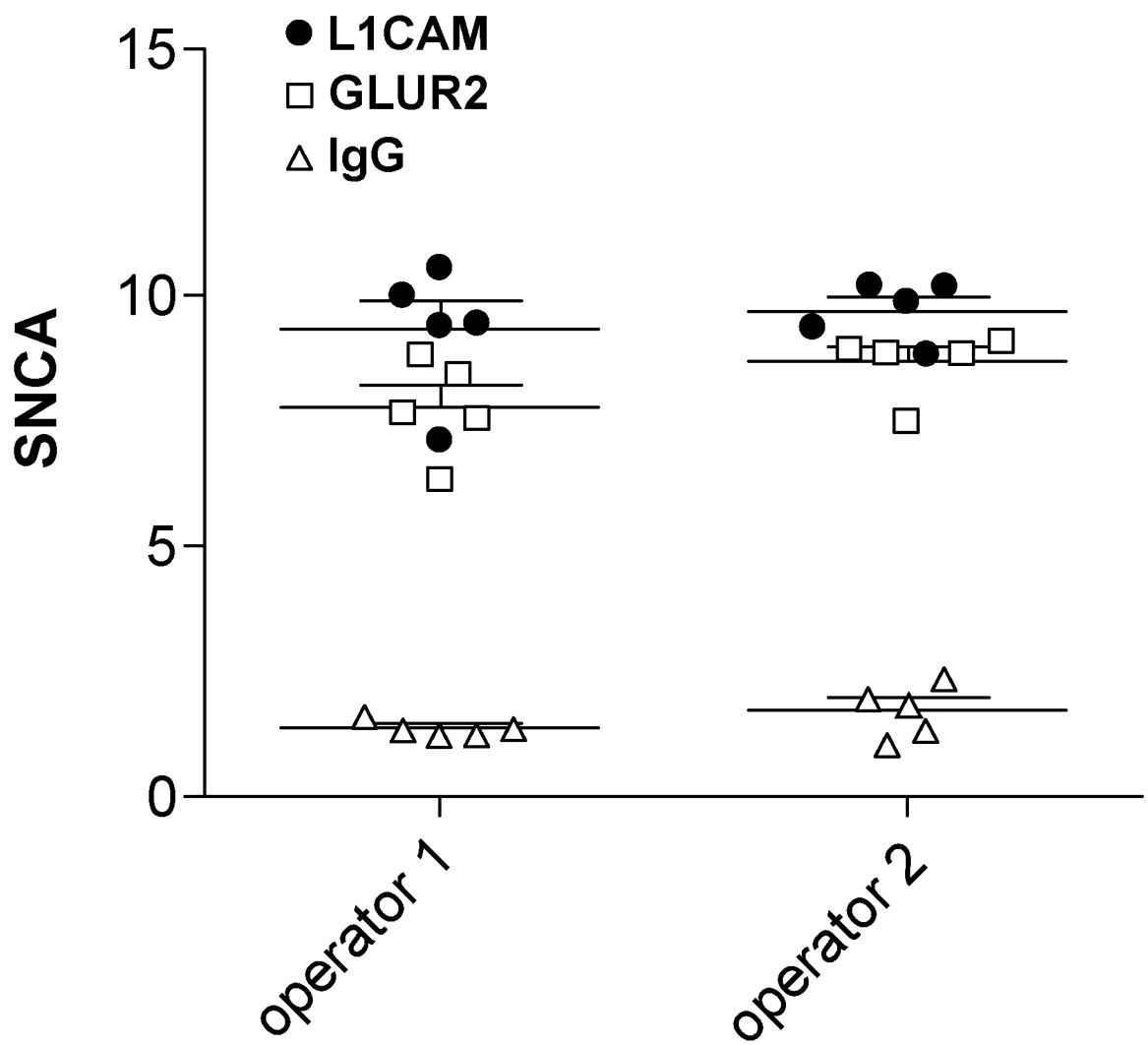
Figure 20C:
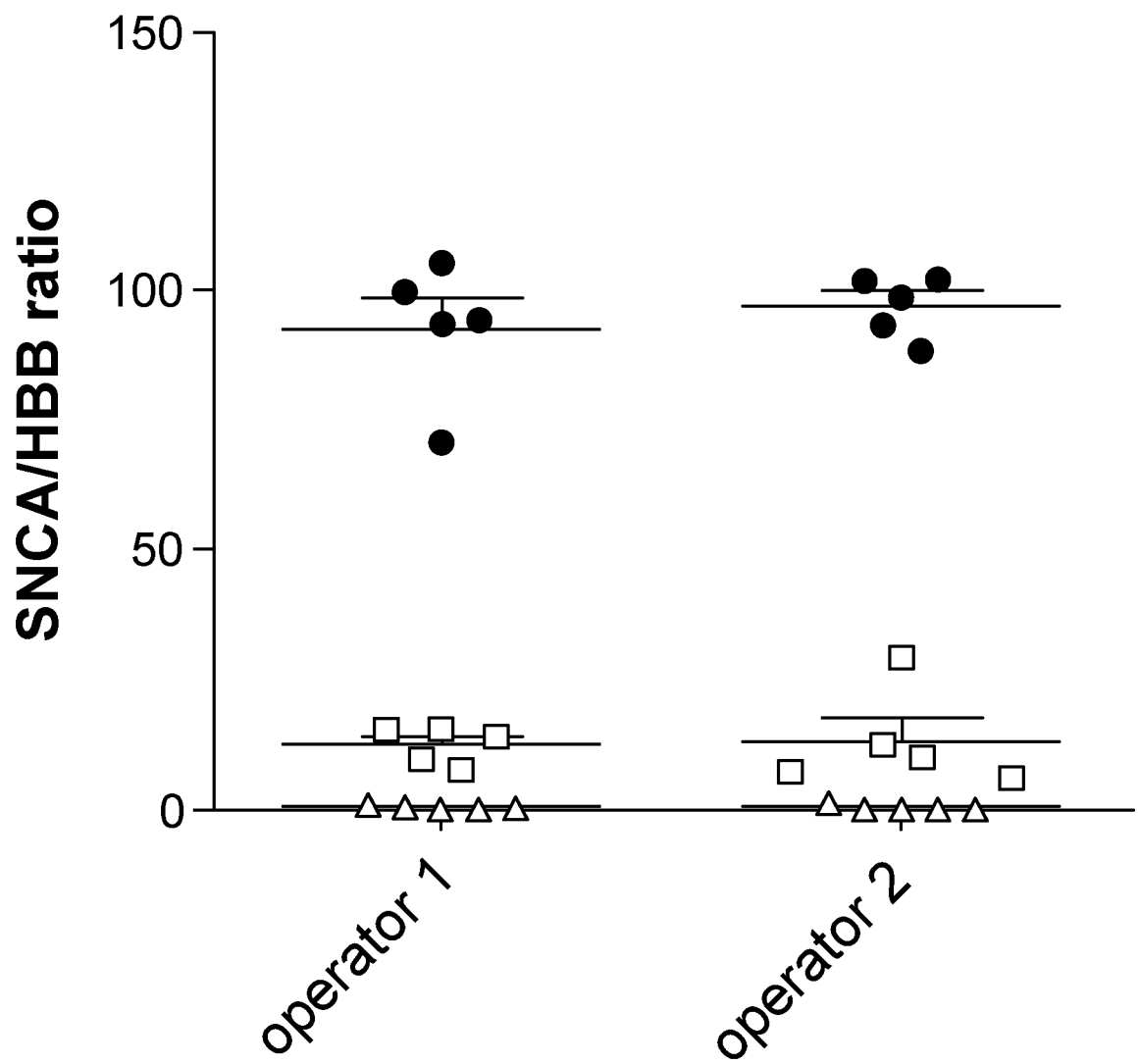

FIG. 20 describes a robust EDDE biomarker enrichment protocol using L1CAM and GluR2 cell surface markers in plasma. The level of SNCA protein enrichment using L1CAM and GluR2 increases in a plasma-dependent manner. Increasing volumes of input plasma increases EDDE neuro enrichment of alpha-synuclein, but not EDDE-IgG control demonstrating specificity of EDDE protocol (FIG. 20A). A two-operator reproducibility study robustly shows increased abundance of alpha-synuclein protein (SNCA) in EDDE neuro samples (FIG. 20B) and increased signal/noise ratio of SNCA/HBB protein levels through EDDE process (FIG. 20C).

FIG. 21A-D demonstrates the clinical utility of EDDE enrichment using either L1CAM (FIG. 21C) or GluR2 (FIG. 21D) in distinguishing Parkinson's patients (10) from healthy individuals (10), through analysis of the protein biomarker SNCA (alpha-synuclein). As controls, this distinction could not be achieved without EDDE enrichment in plasma neat (FIG. 21A), or by IgG-EDDE (FIG. 21B).

Figure 22A:
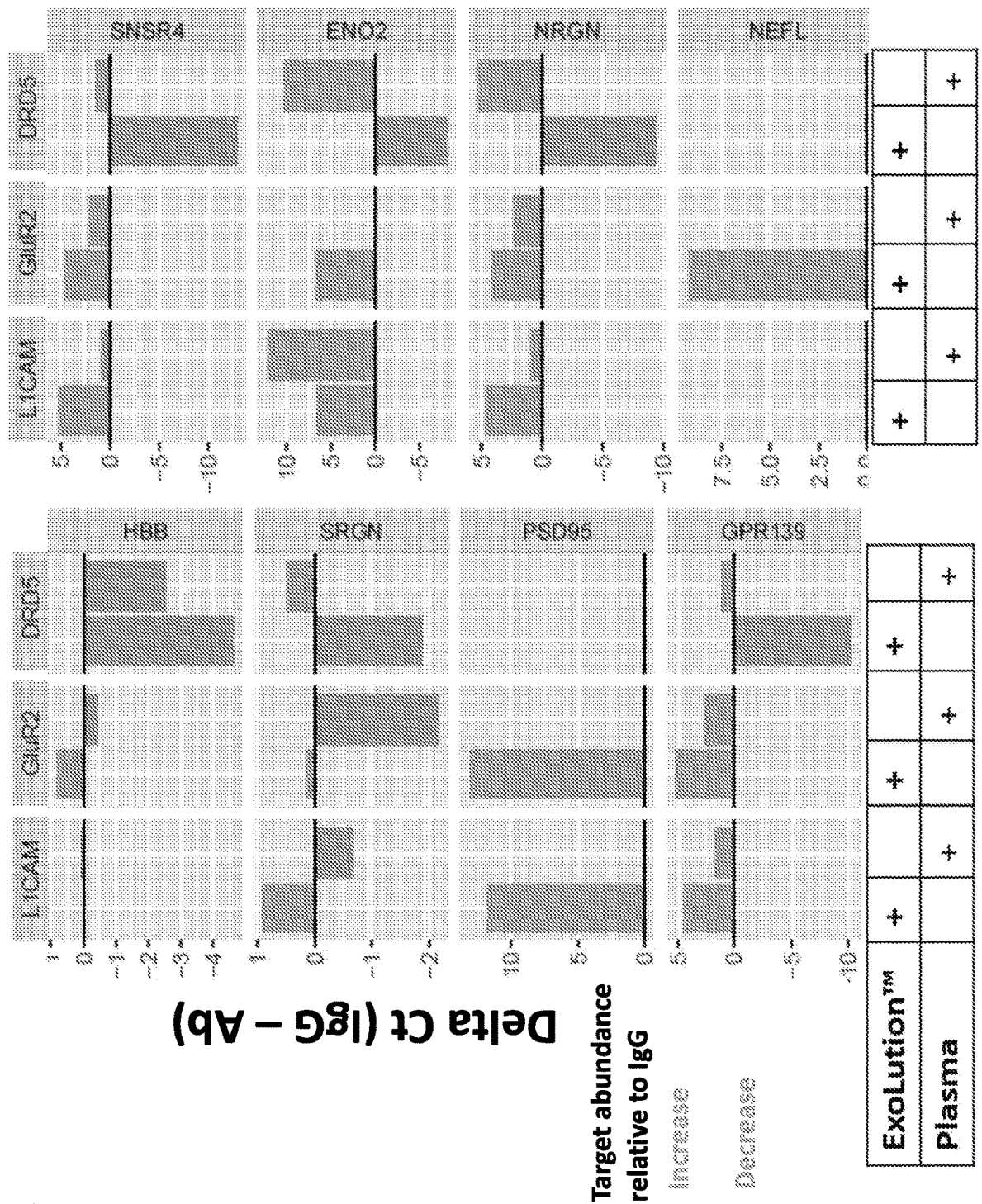

FIG. 22A-B describes EDDE enrichments using either L1CAM and GluR2 showing more neuronal mRNA biomarkers as analyzed by qPCR (delta Ct between Ct from IgG-EDDE minus Ct from a target Ab-EDDE), in comparison to EDDE process using IgG and EDDE using a non-neuronal surface marker DRD5 (FIG. 22A). FIG. 22B describes the digital readout using qPCR for the non-abundant genes in the analysis.

Figure 23:
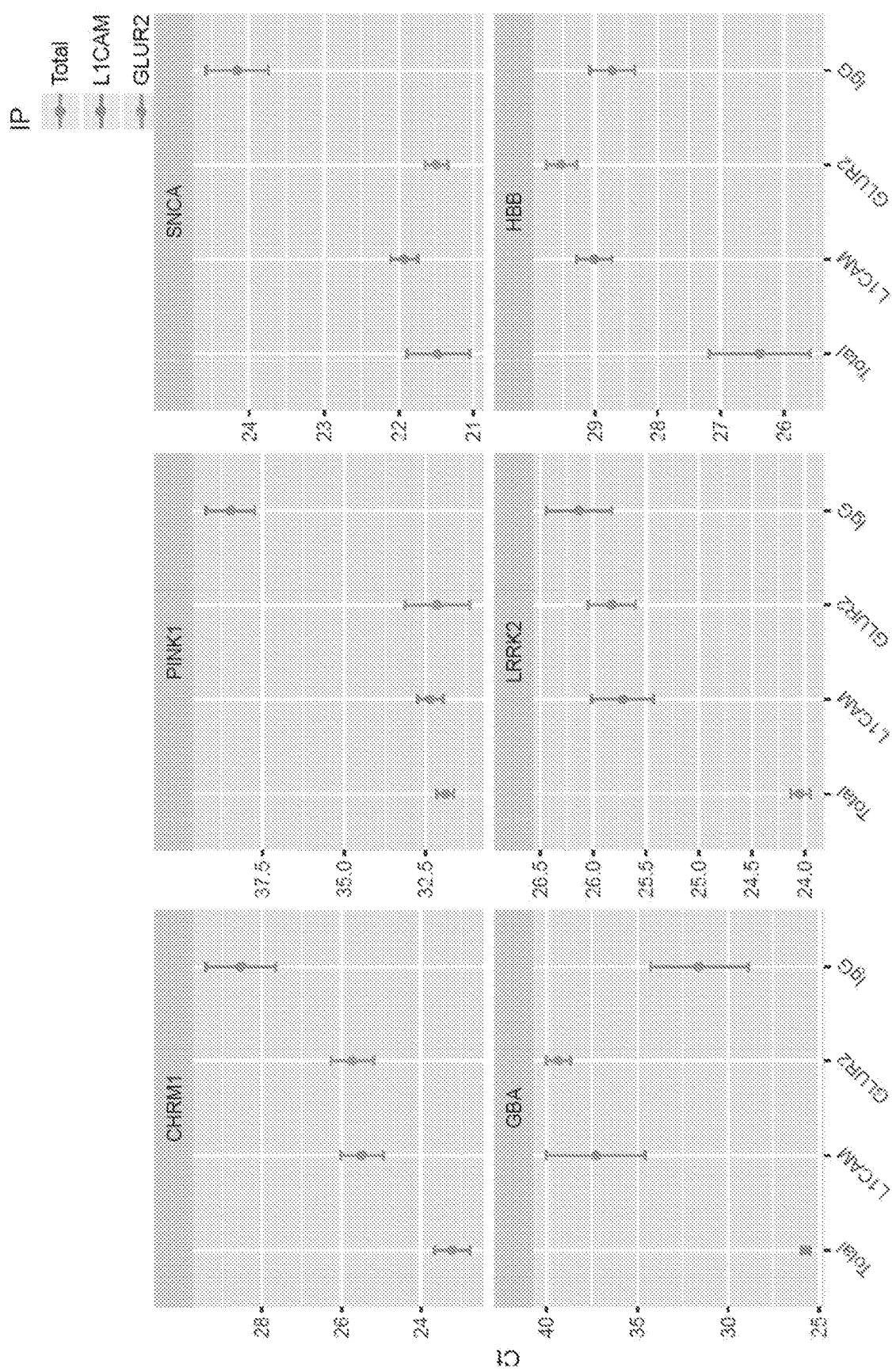

FIG. 23 describes EDDE enrichments using either L1CAM or GluR2 showing enrichment in abundance of Parkinson related mRNA biomarkers (but not HBB) as analyzed by qPCR, in comparison to EDDE process using IgG. As a control, total exosome isolation was performed to serve as a comparison of an enrichment starting point.

Figure 24A:
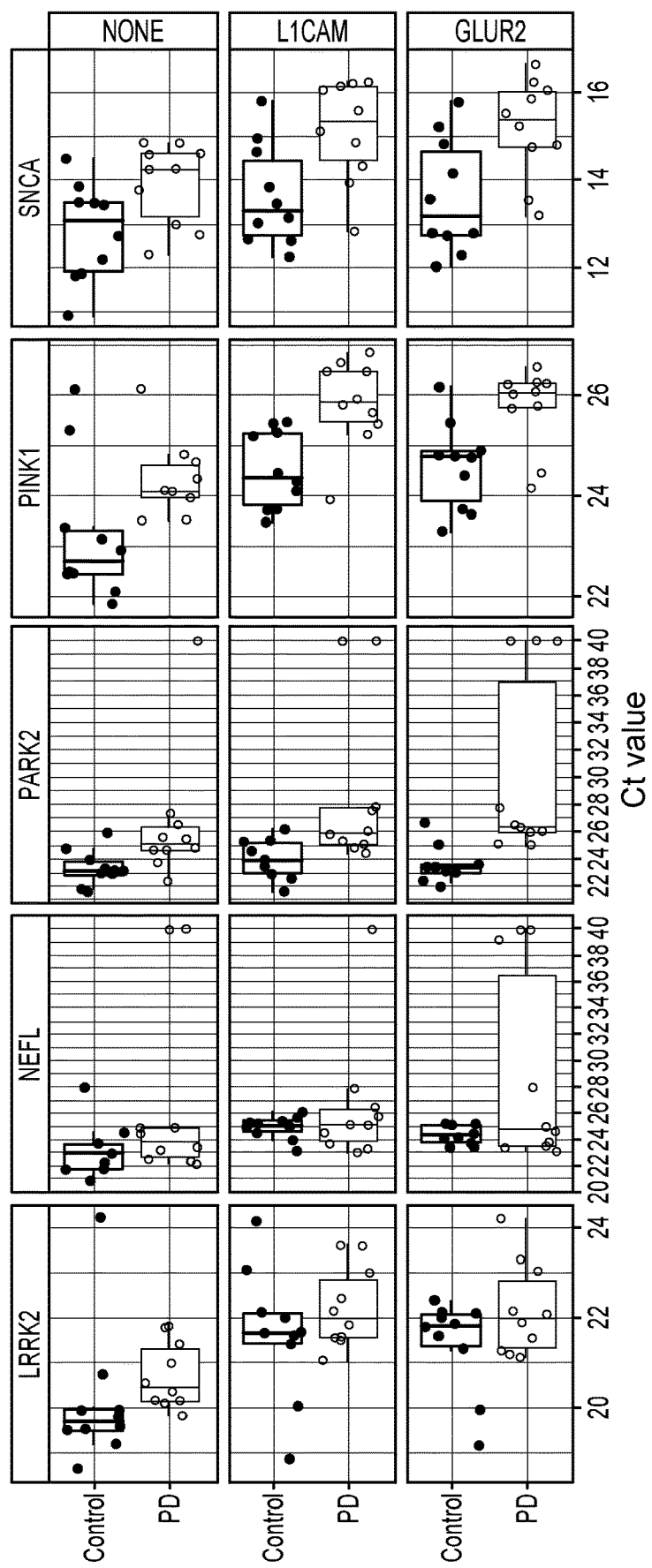
Figure 24B:
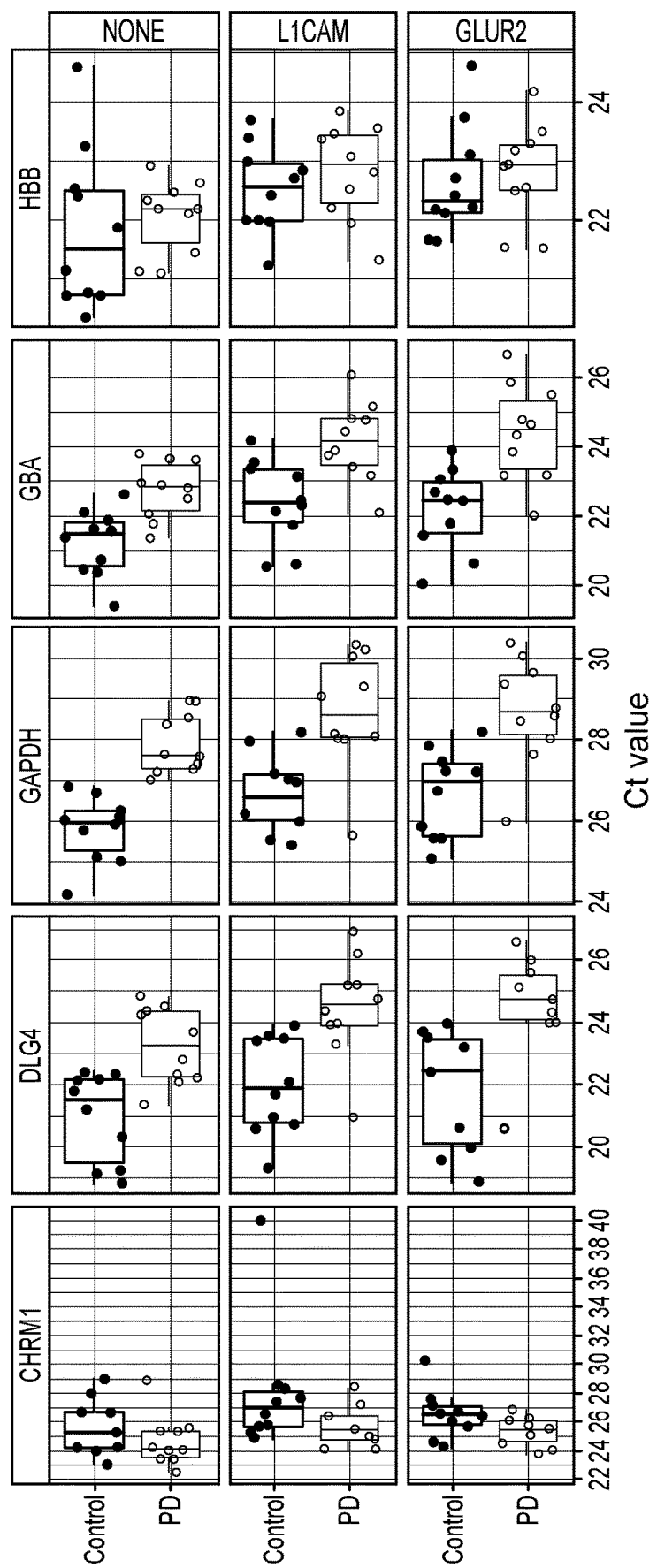

FIG. 24A-B demonstrates EDDE enrichment using either L1CAM or GluR2 clearly distinguishes Parkinson's from healthy individuals through analysis of some Parkinson-related genes by qPCR, in comparison to EDDE process using no specific antibody (FIG. 24A) and (FIG. 24B).

Figure 25:
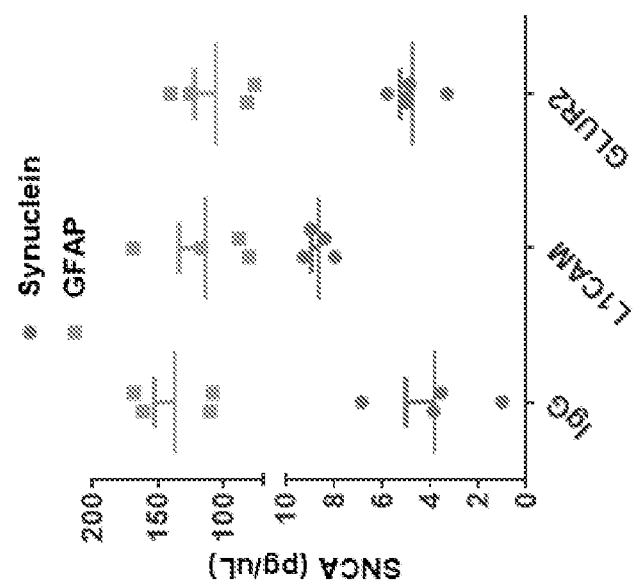

FIG. 25 illustrates EDDE enrichment of Parkinson's biomarker alpha-synuclein protein using either L1CAM or GluR2. In the same process, GFAP whose protein level is not implicated in Parkinson's disease, remained relatively constant.

DETAILED DESCRIPTION OF THE INVENTION

The disclosure provides compositions, kits, and methods for extracellular vesicle (EV) isolation using a process that increases the sensitivity of measuring expression levels of one or more EV-associated protein(s), nucleic acid or metabolite in a biological sample, such as, for example, a biofluid sample.

Further, the present invention is related to the discovery that neuronal exosomes can cross the blood-brain-barrier and are present in plasma samples. It relates to the finding that these exosomes and their cargo can serve as the basis for identifying neurological diseases, disorders or conditions.

In some embodiments, some non-limiting neurological disorders, diseases or conditions include Parkinson Diseases (PD) Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis and traumatic brain injury (TBI).

The processes provided herein start with a biological sample and result with a purified population of total EVs. In some embodiments, the population of EVs is further refined to identify and isolate a specific subpopulation or other subgroup based on detecting a particular surface marker. The isolation of EV populations and any further isolation of subpopulation is performed in a buffer suitable for most downstream measurements assays on proteins, protein modifications, sugars, lipids, RNA, DNA, and metabolites, including, but not limited to, Western Blot, ELISA, qPCR, RNASeq, DNASeq, flow cytometry, immune-fluorescence, immune-gold electron microscopy, and mass spectrometry, and any combination thereof. Any art-recognized techniques for the analysis of the purified populations and/or subpopulations of EVs and their extracted biomarkers provided herein are suitable for use in the processes described herein.

In some embodiments, the isolation of total EVs is based on capturing the EVs on positively or negatively charged capture surface, such as, by way of non-limiting examples, beads and/or columns. In some embodiments, the population of total EVs or one or more subpopulations of EVs from a biological sample are captured or otherwise isolated using any suitable capture surface that can be functionalized with a ligand against a surface protein or other cell surface marker. In some embodiments, the cell surface marker can be used to identify a desired subpopulation or combination of two or more desired subpopulations.

In some embodiments, the capture surface is functionalized with antibodies, recombinant antibodies, co-enzymes, vitamins, proteins, peptides, aptamers, receptor ligands or lectins against different cell surface marker(s) on the EVs. In some embodiments, the capture surface is a population of beads that are functionalized with antibodies, aptamers, ligands or lectins against one or more different surface epitopes on the EVs. In some embodiments, the capture surface is magnetic, agarose, resin, latex, or silicon beads. In some embodiments, the capture surface is a nanoparticle, a chip, sepharose, Sephadex, chromatography column, affinity column or nanotubes.

In some embodiments, the terms "capture surface" and "capture material" are used interchangeably here.

Other nonspecifically-bound plasma metabolites on the capture surface used to isolate EVs, either total EVs or subpopulation(s) of EVs, are removed from the capture surface. In some embodiments, the non-specifically bound plasma metabolites are washed with a modified TBST buffer with 0.1%-5% tween, and a pH in the range of 6.0-9.0. In some embodiments, the non-specifically bound plasma EVs are washed with PBS with 0.1%-3% tween or 0.1-8% BSA. In some embodiments, detergents like 0.01-0.5% Triton x-100 are used to remove the non-specifically bound plasma EVs. In some embodiments, reducing agents like 0.1-5% DTT or 0.5-8% 2-Mercaptoethanol are used to remove the non-specifically bound plasma EVs.

In one embodiment, the EV cargo is eluted from the capture surface. In some embodiments, intact EV cargo is eluted from the capture surface. In some embodiments, EV cargo is eluted from the capture surface by incubation with a lysis buffer. In some cases, the elution process can optionally contain at least one freeze-thaw cycle. In some embodiments, the freeze-thaw cycle occurs at −20° C., sometimes at −80° C. or some temperature in between. In some embodiments, the incubation is at least 30 min up to 6 hrs at room temperature. In some embodiments, the incubation is in the range of about 2-4 hrs. In some embodiments, the incubation is in the range of about 6-24 hrs at a lower temperature, such as, for example, at +4° C.

The processes provided herein allow the user to use different bio-fluids as starting material. In some embodiments, the biological sample may suitably comprise a bodily fluid from a subject. The bodily fluids can be fluids isolated from anywhere in the body of the subject, such as, for example, a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, intra-organ system fluid, ascitic fluid, tumor cyst fluid, amniotic fluid and cell culture supernatant, and combinations thereof. Biological samples can also include fecal or cecal samples, or supernatants isolated therefrom.

The processes provided herein allow the user to choose a different selection of antibodies for isolating specific subpopulations of EVs. The processes is suitable for the measurement of proteins, protein modifications, sugars, lipids, RNA, DNA, RNA/DNA modifications and mutations, as well as metabolites, and any combination thereof.

The processes disclosed herein are generally referred to as "EDDE process" or "EDDE". Those of ordinary skill in the art will appreciate that the EDDE process can be used in any of a variety of ways. For example, in some embodiments, the EDDE process is useful to enrich an isolated EV population based on the detected presence of a cell surface marker on the enriched subpopulation of EVs. This method is referred to herein as an EDDE enrichment process. In some embodiments, the EDDE process is useful to deplete an isolated EV population from one or more different subpopulations of EVs based on the detected presence of a cell surface marker on the subpopulation of EVs to be depleted from the total EV population. This method is referred to herein as an EDDE depletion process.

As used herein, the term "EDDE process" or "EDDE" refers to the following general method: i) functionalizing a capture surface with a reagent that is specific to one or more cell surface markers on EVs generally or is specific to one or more cell surface markers on one or more subpopulations of EVs to isolate the total EV population or one or more subpopulations of EVs from a biological sample; ii) contacting the functionalized capture surface with the biological sample; iii) performing a depletion step, or performing an enrichment step, or a combination thereof to produce a purified total EV population or one or more subpopulations of EVs; and iv) eluting the purified total EV population or one or more subpopulations of EVs, or further manipulating the purified total EV population or one or more subpopulations of EVs, for example, by lysing the EVs within the purified total EV population or one or more subpopulations of EVs. In some embodiments, the eluted purified total EV population or one or more subpopulations of EVs are then subjected to further downstream analysis (e.g., extraction of target biomarkers, followed by analysis and/or comparison of the levels of each of these biomarkers, or other analysis as further disclosed herein). In some embodiments, for a depletion process, step iii) includes at least transferring the supernatant from step ii) to a new tube or other container and isolating the EVs from the supernatant using a suitable capture surface. In some embodiments, the EVs from the supernatant are eluted intact from the suitable isolation capture surface. In some embodiments, the EVs from the supernatant are lysed, and the nucleic acids or proteins from the lysed EVs are extracted. In some embodiments, the eluted intact EVs or the nucleic acids or proteins extracted therefrom are then subjected to further downstream analysis. In some embodiments, for an enrichment process, step iii) washing the functionalized capture surface that has been contacted with the biological sample from step ii) and transferring the washed capture surface to a new tube or other container. In some embodiments, the EVs are eluted intact from the washed capture surface. In some embodiments, the EVs are lysed, and the nucleic acids or proteins from the lysed EVs are extracted. In some embodiments, the eluted intact EVs or the nucleic acids or proteins extracted therefrom are then subjected to further downstream analysis, as described herein.

In one embodiment, through a series of enrichment or depletion steps further disclosed herein, the enrichment and depletion processes employ the use of cell surface makers to capture and arrive at a subpopulation of EVs that contain at least one biomarker. In one embodiment, at least one biomarker disclosed herein are initially enclosed within EVs and these biomarkers are extracted from an isolated and/or purified subpopulation of EVs following an enrichment and/or depletion process disclosed herein. In one embodiment, the terms "biomarkers" and "target biomarkers" refers to nucleic acids, proteins, lipids, metabolites, and/or carbohydrates that are extracted following an enrichment or depletion process disclosed herein.

In one embodiment, provided is a method comprising:
a. contacting a biological sample with a functionalized capture surface under conditions sufficient to form a complex between the functionalized capture surface and at least one cell surface marker, wherein the capture surface is functionalized with a reagent that is specific for the at least one cell surface marker;
b. separating the complex formed between the functionalized capture surface and the at least one cell surface marker from an unbound portion of the biological sample and retaining the captured complex;
c. washing the captured complex formed between the functionalized capture surface and the at least one cell surface marker;
d. enriching one or more subpopulations of EVs having at least one cell surface marker within the biological sample by repeating steps b.-c.; and,
e. isolating and purifying one or more subpopulations of EVs having at least one target biomarker, performing the above a.-d. steps either sequentially or simultaneously if more than one cell surface marker is used.

In one embodiment, at least one cell surface marker is used for EDDE enrichment for the analysis of at least another cell surface protein as a biomarker(s).

In another embodiment, provided is a method comprising:
a. contacting a biological sample with a functionalized capture surface under conditions sufficient to form a complex between the functionalized capture surface and at least one cell surface marker, wherein the capture surface is functionalized with a reagent that is specific for the at least one cell surface marker;
b. separating the complex formed between the functionalized capture surface and the at least one cell surface marker from an unbound portion of the biological sample and retaining the captured complex;
c. washing the captured complex formed between the functionalized capture surface and the at least one cell surface marker;
d. enriching one or more subpopulations of EVs having at least one cell surface marker within the biological sample by repeating steps b.-c.; and,
e. isolating one or more subpopulations of EVs; and,
f. purifying one or more subpopulations of EVs, wherein said EVs contain at least one target biomarker.

In one embodiment, provided is a method comprising the steps of:
a. contacting a biological sample with a functionalized capture surface under conditions sufficient to form a complex between the functionalized capture surface and at least one cell surface marker, wherein the functionalized capture surface comprises a reagent that is specific for the at least one cell surface marker;
b. separating the complex formed between the functionalized capture surface and the at least one cell surface marker from an unbound portion of the biological sample and retaining the unbound portion;
c. depleting one or more subpopulations of EVs having at least one cell surface marker from the biological sample, and performing steps a.-b. either sequentially or simultaneously if more than one cell surface marker is used, by retaining the unbound portion of the biological sample; and optionally,
d. contacting the unbound portion with a second functionalized capture surface under conditions sufficient to form a complex between the second functionalized capture surface and at least one cell surface marker present in the unbound portion;
e. enriching one or more subpopulations of EVs having at least one cell surface marker from the unbound portion of the biological sample, either sequentially or simultaneously with step d. if more than one cell surface marker is used; and,
f. isolating and purifying one or more subpopulations of EVs having at least one target biomarker from the unbound portion of the biological sample.

In another embodiment, the method further comprises the steps of:
g. comparing the levels of at least one target biomarker from the isolated and purified subpopulation of EVs, from a subject and one or more pre-defined threshold (s); and, h. identifying the subject as having a disease or condition; and/or identifying a risk of disease progression in the subject; and/or identifying the subject as being suitable for a therapy if the levels of the at least one biomarker exceeds or differ from one or more pre-defined threshold(s). In one embodiment, the methods disclosed herein further comprise comparing the levels of at least one target biomarker from the isolated and purified subpopulation of EVs, from a subject and one or more pre-defined threshold(s); and, identifying the subject as having a disease or condition; and/or identifying a risk of disease progression in the subject; and/or identifying the subject as being suitable for a therapy if the levels of the at least one biomarker exceeds or differ from one or more pre-defined threshold(s).

Examples of thresholds include the presence/absence of a biomarker, presence of a biomarker at an abundance above some noise-floor/limit of detection of an assay, presence of a biomarker at an abundance above or below some pre-determined absolute level (such as a set concentration or copy number) derived from knowledge of the disease, the abundance of a biomarker relative to another molecule that can act as a normalizer/calibrator where an absolute threshold may be compromised by variations in sample input amount/degradation/etc. Such compromising factors may affect the biomarker and the normalizer molecules similarly and thus divide out. In some embodiments, the relative biomarker/normalizer abundance may either increase or decrease above/below some amount, which would constitute the threshold in this case.

In some embodiments, the methods include a depletion process in which the supernatant from the incubated combination of the antibody/beads complex and the plasma sample is transferred to a new tube and the EV population or RNA extracted from the EV population are isolated as described above.

In some embodiments, the methods include an enrichment process in which the beads in the tube from step iv) are washed one to three times with buffer at pH between 3 to 8, followed by the addition of another buffer at pH 3 to 8. In some embodiments, the capture surface is transferred to a new container.

Those of ordinary skill in the art will also appreciate that the general EDDE process can include additional steps as necessary to isolate one or more EV subpopulations and/or to further analyze the isolated EV population, either total EV population or one or more EV subpopulations.

In some embodiments, the EDDE process includes the following steps: i) washing beads or capture surface; ii) adding antibody, protein or ligand or a combination of antibodies specific for one or more cell surface markers to the washed surface; iii) adding the activated surface or bead complex to biological fluids and exposing the antibody protein or ligand to the antigen or protein in the body fluid; iv) following step iii) with a depletion process or an enrichment process, or a combination thereof; v) eluting or lysing EVs from the capture surface and isolating the supernatant; and vi) eluting the supernatant with acidic/basic buffer or competitive elution with a soluble, competitive antigen or by cleaving the antibody connection to the beads or any other chemical/physical way to strip the beads from antibody to strip antibodies from their antigen. In some embodiments, elution is performed on intact exosomes for downstream analysis of EV content, as described elsewhere herein. In some embodiments, elution with biotinylated antibody against a desthiobiotinylated-antibody-bead-exosome complex can be alternatively used.

In some embodiments, the volume of beads used is varied, for example, in the range of about 50 to 200 µl. In some embodiments, magnetic beads are used, e.g., Dynabeads 2.7 µm or 4.5 µm; EXO-Flow (SBI); exoCap (MBL), Ocean-Nano (50 nm-100 nm beads), or any other suitable commercially available magnetic bead. In some embodiments, resin, agarose, latex, or silicon beads are used. In some embodiments, beads with protein A/G are used. In some embodiments, beads with streptavidin are used. Any other suitable means for chemical coupling of antibodies to beads can be used in the processes described herein.

In some embodiments, the beads are washed in a different wash buffer. In some embodiments, the washing buffer does not contain BSA. In some embodiments, the washing buffer contains TBST.

In some embodiments, the amount of antibody can vary between antigens and between depletion/enrichment processes. In some embodiments, the amount of antibody used to functionalize the capture surface is in a range between 2-40 µg. In some embodiments, the incubation for the capture surface, e.g., beads, and the reagent, e.g., antibody, is in a range between about 30 min to up to about 12 hours. In some embodiments, the incubation for the capture surface, e.g., beads, and the reagent, e.g., antibody, is performed with or without rotation. In some embodiments, the incubation for the capture surface, e.g., beads, and the reagent, e.g., antibody, is performed at room temperature. In some embodiments, the incubation for the capture surface, e.g., beads, and the reagent, e.g., antibody, is performed at 4° C.

In some embodiments, following incubation of the capture surface, e.g., beads, and the reagent, e.g., antibody, the functionalized capture surface is washed at least once with a buffer. In some embodiments, the functionalized capture surface is washed between 1 to 8 times. In some embodiments, the functionalized capture surface is washed with PBS or a PBS-based buffer, such as, for example, a PBS buffer with 0.5-7.5% BSA incorporated therein. In some embodiments, the functionalized capture surface is washed with TBST or a TBST-based buffer, such as, for example, a TBST buffer with 0.5-7.5% BSA incorporated therein.

In some embodiments, the biological sample is varied. In some embodiments, the starting material for the biological sample is cell culture condition media, urine, CSF or any other biofluid. In some embodiments, the starting material is used with or without pre-processing of the sample, such as, for example, centrifuging the sample, filtering the sample, or pre-clearing the sample with a non-functionalized population of beads and/or depleting any abounded proteins. In some embodiments, the starting material is a population of EVs isolated by any suitable isolation method such as, for example, ultracentrifugation (UC), ExoQuick, exoEasy and ultrafiltration, size exclusion chromatography, ultrafiltration and combinations thereof. In some embodiments, the starting material is derived from any type of biofluid. In some embodiments, the incubation for the functionalized capture surface, e.g., beads coupled to antibodies, and the biological sample, e.g., a biofluid, is in a range between about 30 min to up to about 24 hours. In some embodiments, the incubation for the functionalized capture surface, e.g., beads coupled to antibodies, and the biological sample, e.g., a biofluid, is performed with or without rotation or agitation. In some embodiments, the incubation for the functionalized capture surface, e.g., beads coupled to antibodies, and the biological sample, e.g., a biofluid, is performed at room temperature. In some embodiments, the incubation for the functionalized capture surface, e.g., beads coupled to antibodies, and the biological sample, e.g., a biofluid, is performed at 4° Celsius. In some embodiments, the antibody or combination of antibodies is added directly to the plasma or body fluid and the antibody-antigen interaction occurs before being exposed to the capture surface. The capture surface then retrieves the antibody-EV complex from the body fluid.

In some embodiments of a depletion process, the transferred supernatant is subjected to further isolation or other purification. In some embodiments, the supernatant undergoes at least a second round of depletion for the same or other target antigen. In some embodiments, the supernatant is used as the starting material for enrichment process for any antigen of interest. In some embodiments of a depletion process, the supernatant is directly used as the source of RNA, protein or lipid extraction.

In some embodiments of an enrichment process, the number and pattern of washing steps is varied depending on the antigen of interest and/or the sensitivity/specificity of the downstream application. In some embodiments, the pH of the TBST buffer can vary from about pH 6 to about pH 9. In some embodiments, the tween concentration of the wash buffer is in a range between about 0.1-5%. In some embodiments, the NaCl concentration of the wash buffer is in the range of about 150-1000 mM. In some embodiments, the tween concentration of the wash buffer is in a range between about 0.1-5%, and the NaCl concentration of the wash buffer is in the range of about 150-1000 mM. In some embodiments, the washing is performed without tube switching.

In some embodiments, the lysis buffer is used with or without proteinase, phosphatase or RNAse inhibitors. In some embodiments, the vortex is replaced by sonication, freeze-thaw cycle or any physical perturbation.

In some embodiments, capture surface is functionalized with a reagent that specifically binds or otherwise targets a specific cell surface marker or combination of cell surface markers that are specific for a desired cell type or that are specific for a desired population of EVs that are derived from a specific cell type.

The tables below and FIG. 11 provide a list of exemplary cell surface markers that can be used in the EDDE process described herein. Those of ordinary skill in the art will appreciate that this list is not exhaustive, and that any suitable cell surface marker known in the art can be used in the EDDE process described herein. Those of ordinary skill in the art will also appreciate that some markers are useful for also identifying cells that are involved with certain biological functions. For example, LAMP2 is known to be a marker for autophagy/lysosomal activity. Such markers are also useful in the EDDE process described herein.

TABLE 1A

| Cell of origin | Possible markers |
| --- | --- |
| Immune cell | CD138, CD38, CD45, CD70 |
| T-cell | CD28, CD3, CD4, CD8, CD215 |
| B-cell | CD19, CD20 |
| NK cell | CD56, CD10, CD335 |
| Monocyte | CD11, CD123, CD14, CD163, CD33, CD303 |
| Endothelial | CD62E, CD146, CD71, CD144, CD90, CD309, CD31/PCAM, E-Selectin, CD34, VEGFR, CD40L and CD154, VE-cadherin, von, Willebrand factor, KDR, FLT1 |
| Epithelial | EpCAM, CD326, CD113, CD118 |
| Platelet | CD62, CD61, CD41, CD42, CD140 |
| Erythrocyte | CD235, CD233, CD234, CD236, CD241 |
| Neuronal cell | L1CAM, NCAM, DRD5, DRD2, GRIA2, SNAP25, SYP, GluR2 |
| Cancer cell | CD44, CD184, PSMA, C-MET, EGFR, CTLA4, PDL1, Glypican 1, EGFR v3, IDH1, PD1 |
| Embryo | SSEA-4, SSEA-3, PODXL, HSPA8, CD324, KSPG |
| Astrocyte | GLAST-1, AQP4, |
| Oligodendrocyte | PLP, O4, MOG |
| Various cell types | GBM43, GBM6, LN18, GBM22, U118MG, GBM10, U128MG, LN229, T98G, LN2308, GBM20/3, Follitin 1, Follitin 2, Integrin 1 Integrin 2, LAMP1, FOLR1, EPHA2, TSG101, Claudin3, HER2, MUC18, CA125, D2-40, CD9, HSP90, CA19-9, CD24 |

TABLE 1B

| Other markers that could be used for enrichment or depletion | | | | |
| --- | --- | --- | --- | --- |
| PECAM1 | ALCAM | ICAM2 | CD40 | HSP70 |
| RETN | C5AR1 | IL12RB1 | CD40LG | Galectin 5 |
| S100A8 | CD160 | IL1R2 | CD5 | Galectin 9 |
| SELP | CD163 | IL2RA | CD6 | Heat shock 70 kDa protein 1-like |
| ST6GAL1 | CD19 | ITGA1 | CD63 | Heat shock 70 kDa protein 4-like |
| EPCAM | CD1A | ITGA2 | CD69 | Myeloid-associated differentiation marker 2 |
| TEK | CD1C | ITGA3 | CD7 | Aquaporin-1 |
| TNFRSF4 | CD1D | KLRB1 | CD70 | Serglycin |
| TNFRSF8 | CD2 | KLRC1 | CD72 | Aquaporin-4 |
| TPSAB1,TPSB | CD209 | KLRD1 | CD74 | Tweety family member 1 |
| VCAM1 | CD22 | KRT18 | CD79A | Glycophorin A |
| VWF | CD24 | KRT5 | CD79B | Peptidyl arginine deiminase, type IV |
| CD3G | CD244 | KRT8 | CD80 | Peptidoglycan recognition |
| CD4 | CD247 | MS4A1 | CD83 | Chloride channel protein 2 |
| NOS3 | CD28 | MYH10 | CD86 | Sialophorin, CD43 |
| NT5E | CD37 | MYH9 | CD8A | A-125 (MUC-16) or CA19- 9. |
| NCAM1 | CD38 | MYOCD | CD8B | HER2/neu |
| CD96 | CD3D | A-125 (MUC-16) | CA19-9 | N-CAM |
| CA125 | ITGB1 | ITGB2 | polysaccharides | any CD marker |
| amylose | amylopectin | cellulose | lipopolysaccharid | glycosaminoglycan |
| proteoglycans | oligosaccharide | glycoproteins | glycolipids | lectins |

In some embodiments, the disclosure provides methods for isolating EVs from a biological sample following a depletion process, where non-relevant EVs are depleted from a biological sample based on the expression, or lack thereof, of one or more cell-surface markers.

In some embodiments, the disclosure provides methods for isolating exosomes from a biological sample using a depletion process, where non-relevant exosomes are excluded from a biological sample based on the expression, or lack thereof, of one or more cell-surface markers. In some embodiments, the one or more cell-surface markers is selected from the group consisting of HSP70, Galectin 5, Galectin 9, Heat shock 70 kDa protein 1-like, Heat shock 70 kDa protein 4-like, Myeloid-associated differentiation marker 2, Aquaporin-1, Serglycin, Aquaporin-4, Tweety family member 1, Glycophorin A, Peptidyl arginine deiminase, type IV, Peptidoglycan recognition protein 1, Chloride channel protein 2, Sialophorin, CD43, and any combination(s) thereof. In some embodiments, the exclusion strategy uses two or more cell-surface markers, e.g., three or more, four or more, five or more, six or more, seven or more, eight or more, nine or more, and/or ten or more cell-surface markers.

In one embodiment, the disclosure also provides methods for efficient enrichment of a cancer-specific exosome signature using a depletion process. In some embodiments, the disclosure also provides methods for the efficient enrichment of a GluR2 biomarker for predicting a risk of, identifying most useful drug targets for, or for monitoring progression and responses to therapy of neurodegenerative diseases. In some embodiments, a method for enriching a GluR2 biomarker does not involve a depletion process.

In one embodiment, provided is a method of identifying and isolating or obtaining extracellular vesicles of neuronal origin in plasma samples based on their surface antigen decoration and then assaying the protein(s) and RNA cargo of the neuronal derived EVs for the identification or prognosis of neurodegenerative diseases, disorders or conditions. The method can include early detection of subject risk for a neurodegenerative disorder, patient stratification for clinical enrollment or predict treatment response. The assay comprises enriching neuronal derived exosomes (NDE) based on the presence of the neuronal marker GluR2 on the exosome surface and then measuring different groups of biomarkers consisting of specific proteins, including α-synuclein, Tau, phosphorylated Tau, ubiquitinated proteins and synaptic proteins as well as mRNA of different disease-related genes. The method can be based on the assessment of the level of one or more biomarkers associated with the GluR2 decorated exosomes. In some embodiments, the level of all RNA can be determined by RNAseq or any other transcriptomic methodology. In other embodiments, the GluR2 decorated exosomes' protein or lipid cargo can be characterized by different -omic methods including mass-spectrometry and antibody array.

In some embodiments, the GluR2 decorated exosomes can be enriched from different biofluids including serum, plasma, urine, interstitial fluid, peritoneal fluid, cervical swab, tears, saliva, buccal swab and cerebrospinal fluid. In yet other embodiments, α-synuclein is measured in total, as an aggregate form or as an aggregate to monomer ratio. Post translation modification of α-synuclein or other disease-related proteins including, but not limited to phosphorylation and ubiquitination can be measured in GluR2 decorated exosomes. In further embodiments, the method quantifies the number of isolated GluR2 decorated vesicles as the biomarker itself, alone or in combination with any cargo. In other embodiments, the GluR2 decorated vesicles are enriched from the general population of membrane vesicles existing in any body-fluid, including, but not limited to exosomes, microparticles, microvesicles, nanosomes, extracellular vesicles, and ectosomes.

In one embodiment, the present invention provides methods for isolating subgroups of extracellular vesicles, including, for example, exosomes and microvesicles, from biofluids, such as, for example, plasma, serum, urine, saliva, seminal fluid and/or CSF, to provide for downstream detection of specific proteins RNA, lipids, metabolites and carbohydrates (e.g., lectins).

In some embodiments, the disclosure also provides methods for efficient enrichment of one or more subpopulations of neuronal derived exosomes (NDE) using an enrichment process, which is based on the expression of cell-surface marker GluR2.

In some embodiments, the neuronal exosome enrichment process comprises first removing the complex formed between the reagent and one or more surface markers from non-neuronal biological sample and retaining the unbound portion(s) of the biological sample for analysis.

In some embodiments, the depletion process is followed by contacting the unbound portion(s) of the biological sample with a capture surface under conditions sufficient to retain at least a portion of the EVs in the unbound portion(s) of the biological sample on or in the capture surface.

In some embodiments, when a depletion process is initially performed, the depletion process is followed by an enrichment process. In other embodiments, the enrichment process comprises retaining the captured complex formed between the reagent and the at least one cell-surface marker from the biological sample.

In some embodiments, the method further comprises extracting one or more nucleic acids, proteins, lipids or metabolites from the EVs for at least one biomarker in the biological sample.

In some embodiments, the methods disclosed herein further comprises a step of extracting one or more nucleic acids from the EVs as a biomarker. Nucleic acids can be found in smaller vesicles ranging in size from about 10 nm in diameter to about 10000 nm in diameter. For example, "exosomes" have diameters of approximately 30 to 200 nm, with shedding microvesicles and apoptotic bodies often described as larger. Exosomes, shedding microvesicles, microparticles, nanovesicles, apoptotic bodies, nanoparticles and membrane vesicles co-isolate using various techniques. Other nucleic acid-containing materials, such as RNA-protein complexes, may co-isolate with cells and microvesicles using the various methods and techniques described herein.

In some embodiments, the biological sample is selected from the group consisting of blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof. In some embodiments, the bodily fluid is urine, blood, plasma, serum, or cerebrospinal fluid. In some embodiments, biological sample is plasma or serum.

In some embodiments, the reagent that is specific for GluR2 is specific for a cell type selected from the group consisting of cells such as neuronal cells, peripheral nerve cells, central nerve cells, nervous system-support cells such as endothelia cells, glia, immune cells, oligodendrocytes, connective tissue-derived cells.

In some embodiments, the enrichment process comprises washing the functionalized capture surface that has been contacted with the biological sample.

In some embodiments, the extracted nucleic acid is RNA or an RNA species.

In some embodiments, the extracted nucleic acid(s) are subjected to downstream analysis, for example, to measure and/or compare levels of expression to predetermined thresholds. For example, at least one biomarker (i.e. —one or more), such as a group of genes, may be identified as a signature by analyzing clinical samples procured with stringent inclusion and exclusion criteria for the intended clinical utility. On a per-sample basis, a continuous or discrete score may be derived by performing a statistical classification analysis including but not limited to random forest, logistic regression and neural network. On this score, a threshold is defined that separates intended sample groups for the clinical utility with an acceptable clinical specificity and sensitivity.

In some embodiments, the functionalized capture surface comprises one or more membrane, chip, nanoparticle or population of nanoparticles, nanotube or population of nanotubes, slide, chromatography medium, and any combination thereof.

In some embodiments, the functionalized capture surface comprises a population of beads or a mixture of a population of beads. In some embodiments, the beads are magnetic beads. In some embodiments, the beads are agarose beads. In some embodiments, the beads are silicon beads.

In some embodiments, the at least one cell surface marker is present on the surface of the EVs or at least one biomarker is extracted from within the EVs. In some embodiments, the reagent that is specific for at least one cell surface marker comprises an antibody or a mixture of antibodies. In some embodiments, the reagent that is specific for at least one cell surface marker comprises a peptide or any other receptor ligand.

In one embodiment, antibodies are coupled to beads or other rigid surfaces by conventional methods like biotin-streptavidin interaction, or a strong covalent interaction. The antibody-surface complex is exposed to plasma samples, other biofuels or exosomes isolated from these fluids. Then the beads-surface-exosomes complex is isolated based on, physical separation or centrifugation and washed until the desired signal to noise ratio is achieved.

In some embodiments, control particles may be added to the sample prior to EV isolation and/or nucleic acid extraction to serve as an internal control to evaluate the efficiency or quality of EV purification and/or proteins and nucleic acid extraction. The methods described herein provide for the efficient isolation and the control particles along with the EV fraction.

These control particles include Q-beta bacteriophage, virus particles, or any other particle that contains control proteins and nucleic acids (e.g., at least one control target gene or protein) that may be naturally occurring or engineered by recombinant DNA techniques, or by liposome vesicle encapsulation technologies such as with engineered at least one surface protein and at least one control target nucleic acid or at least one control target protein being encapsulated inside the liposomal vesicles. In some embodiments, the quantity of control particles is known before the addition to the sample. The control target gene or control target protein can be quantified using real-time PCR, ELISA, or Western blot analysis.

Quantification of a control target gene or a control target protein can be used to determine the efficiency or quality of the EV purification, protein or nucleic acid extraction processes.

In some embodiments, the methods and kits described herein include one or more in-process controls. In some embodiments, the in-process control is detection and analysis of a reference gene that indicates plasma quality (i.e., an indicator of the quality of the plasma sample). In some embodiments, the reference gene(s) is/are a plasma-inherent transcript. In some embodiments, the reference gene(s) is/are analyzed by additional qPCR. In some embodiments, the in-process control is detection and analysis of extracellular vesicle protein. The reference protein is/are analyzed by additional ELISA or Western blot.

In some embodiments, the reagent that is specific for at least one cell surface marker is specific for a cell type selected from the group consisting of an immune cell, a T-cell, a B-cell, an NK cell, a monocyte, an endothelial cell, an epithelial cell, a platelet, an erythrocyte, a neuronal cell, a cancer cell, an embryonic cell, an astrocyte, an oligodendrocyte, and any combination thereof.

In some embodiments, the biological sample is pre-processed prior to contacting the biological sample and the functionalized capture surface.

In some embodiments, the nucleic acids described herein comprise DNA or RNA. Examples of RNA include messenger RNAs, long non-coding RNAs, transfer RNAs, ribosomal RNAs, small RNAs (non-protein-coding RNAs, non-messenger RNAs), microRNAs, piRNAs, snRNAs, snoRNAs, and Y-RNAs. In some embodiments, the nucleic acids are isolated from or are otherwise derived from EVs or from one or more subpopulations of EVs. In some embodiments, the nucleic acids are cell-free nucleic acids, also referred to herein as circulating nucleic acids. In some embodiments, the cell-free nucleic acids are DNA or RNA.

As used herein, the term "nucleic acids" refer to DNA and RNA unless otherwise specified. The nucleic acids can be single stranded or double stranded. In some instances, the nucleic acid is DNA. In some instances, the nucleic acid is RNA. RNA includes, but is not limited to, messenger RNA, transfer RNA, ribosomal RNA, non-coding RNAs, microRNAs, and HERV elements.

In some embodiments, the capture surface is positively charged. In another embodiment, the capture surface is negatively charged. In yet another embodiment, the capture surface is neutral. In some embodiments, the capture surface is functionalized with molecules such as heparin or heparin sulfate proteoglycans.

GluR2 Cell Surface Marker for Neuronal Exosome Enrichment

In one embodiment, the disclosure provides a method for isolating a subpopulation of EVs from a biological sample comprising the steps of: (a) providing a biological sample from a human subject; (b) producing a functionalized capture surface, wherein the capture surface is functionalized with a reagent that is specific for the GluR2 protein; (c) contacting the biological sample from the human subject with the functionalized capture surface under conditions sufficient to form a complex between the functionalized capture surface and GluR2 in the biological sample; (d) separating the complex formed between the functionalized capture surface and GluR2 from the unbound portion(s) of the biological sample to obtain a captured complex and retaining the captured complex for an enrichment process; (e) purifying the subpopulation of EVs from the biological sample through an enrichment process disclosed herein; and optionally (f) extracting one or more biomarker nucleic acids, proteins, carbohydrates or lipids from the purified subpopulation of EVs.

In one embodiment, the methods for enriching exosomes are based on the presence of cell surface markers such as GluR2. In some embodiments, exosomes are isolated from 0.1-3 ml of plasma samples or other body fluids described herein.

In other embodiments, the isolated neuronal enriched exosomes are used for measurement of protein(s), protein aggregates, protein complexes and/or protein modifications. In other embodiments, the isolated neuronal enriched exosomes are used for RNA measurement. In other embodiments, the neuronal enriched exosomes directly and/or their protein and RNA cargo is isolated from healthy or diseases samples. In other embodiments, the neuronal enriched exosomes directly and/or their protein and RNA cargo is used to identify neurodegenerative disease/disorder/condition risk, treatment response or stratification.

In some embodiments, the disclosure also provides methods for the use of EV RNA signatures to monitor treatment efficacy and/or to predict treatment efficacy. In some embodiments, the methods are used to monitor treatment efficacy longitudinally.

As used herein, the term "biological sample" refers to a sample that contains biological materials such as DNA, RNA, lipids, carbohydrates, metabolites and proteins.

A suitable sample volume of a bodily fluid used in any EDDE process is, for example, in the range of about 0.1 ml to about 30 ml fluid. The volume of fluid may depend on a few factors, e.g., the type of fluid used. For example, the volume of serum samples may be about 0.1 ml to about 4 ml, preferably about 0.2 ml to 4 ml. The volume of plasma samples may be about 0.1 ml to about 4 ml, preferably 0.5 ml to 4 ml. The volume of urine samples may be about 2 ml to about 30 ml, e.g., about 10 ml to about 30 ml, preferably about 20 ml.

While the examples provided herein used plasma samples, the skilled artisan will appreciate that these methods are applicable to a variety of biological samples. Other suitable biological samples include urine, cerebrospinal fluid, blood including blood components, e.g., plasma and serum, sputum, pleural fluid, nipple aspirates, lymph fluid, fluid of the respiratory, intestinal, and genitourinary tracts, tear fluid, saliva, breast milk, fluid from the lymphatic system, semen, intraorgan system fluid, ascitic fluid, tumor cyst fluid, amniotic fluid, cell culture supernatant and combinations thereof.

The methods and kits of the disclosure are suitable for use with samples derived from a human subject. The methods and kits of the disclosure are suitable for use with samples derived from a human subject. In addition, the methods and kits of the disclosure are also suitable for use with samples derived from a human subject. The methods and kits of the disclosure are suitable for use with samples derived from a non-human subject such as, for example, a rodent, a non-human primate, a companion animal (e.g., cat, dog, horse), and/or a farm animal (e.g., chicken).

The term "subject" is intended to include all animals shown to or expected to have nucleic acid-containing particles. In particular embodiments, the subject is a mammal, a human or nonhuman primate, a dog, a cat, a horse, a cow, other farm animals, or a rodent (e.g. mice, rats, guinea pig. etc.). A human subject may be a normal human being without observable abnormalities, e.g., a disease. A human subject may be a human being with observable abnormalities, e.g., a disease. The observable abnormalities may be observed by the human being himself, or by a medical professional. The term "subject," "patient," and "individual" are used interchangeably herein.

Methods

A wide range of surfaces are capable of capturing EVs according to the methods provided herein. While the working examples provided herein use beads as the capture surface, it should be understood that the format of the capturing surface, e.g., plate, tube, membranes or other filter does not affect the ability of the methods provided herein to efficiently capture EVs from a biological sample.

In some embodiments, the capture surface is a membrane. In some embodiments, the capture surface is a plastic or a glass. For example, the bottom of a plate or a slide. In some embodiments, the capture surface is a tube. In some embodiments, the capture surface is a bead. For example, the bead is magnetic. Alternatively, the bead is non-magnetic. In yet another embodiment, the bead is functionalized with an affinity ligand.

The present disclosure also describes a device for isolating and concentrating EVs from biological or clinical samples using disposable plastic parts and centrifuge equipment. For example, the device comprises a column comprising a capture surface (i.e., a membrane filter), a holder that secures the capture surface between the outer frit and an inner tube, and a collection tube. The outer frit comprises a large net structure to allow passing of liquid, and is preferably at one end of the column. The inner tube holds the capture surface in place, and preferably is slightly conus-shaped. The collection tube may be commercially available, i.e., 50 ml Falcon tube. The column is preferably suitable for spinning, i.e., the size is compatible with standard centrifuge and micro-centrifuge machines.

In embodiments where the capture surface is a membrane, the device for isolating the EV fraction from a biological sample contains at least one membrane. In some embodiments, the device comprises one, two, three, four, five or six membranes. In some embodiments, the device comprises three membranes. In embodiments where the device comprises more than one membrane, the membranes are all directly adjacent to one another at one end of the column. In embodiments where the device comprises more than one membrane, the membranes are all identical to each other, i.e., are of the same charge and/or have the same functional group.

It should be noted that capture by filtering through a pore size smaller than the EVs is not the primary mechanism of capture by the methods provided herein. However, filter pore size is nevertheless very important, e.g., because mRNA becomes stuck on a 20 nm filter and cannot be recovered, whereas microRNAs can easily be eluted off, and e.g. because the filter pore size is an important parameter in available surface capture area.

The methods provided herein use any of a variety of capture surfaces. In some embodiments, the capture surface is a membrane, also referred to herein as a filter or a membrane filter. In some embodiments, the capture surface is a commercially available membrane. In some embodiments, the capture surface is a charged commercially available membrane. In some embodiments, the capture surface is neutral. In some embodiments, the capture surface is selected from Mustang® Ion Exchange Membrane from PALL Corporation; Vivapure® Q membrane from Sartorius AG; Sartobind Q, or Vivapure® Q Maxi H; Sartobind® D from Sartorius AG, Sartobind (S) from Sartorius AG, Sartobind® Q from Sartorius AG, Sartobind® IDA from Sartorius AG, Sartobind® Aldehyde from Sartorius AG, Whatman® DE81 from Sigma, Fast Trap Virus Purification column from EMD Millipore; Thermo Scientific* Pierce Strong Cation and Anion Exchange Spin Columns.

In embodiments where the capture surface is charged, the capture surface can be a charged filter selected from the group consisting of 0.65 um positively charged Q PES vacuum filtration (Millipore), 3-5 um positively charged Q RC spin column filtration (Sartorius), 0.8 um positively charged Q PES homemade spin column filtration (Pall), 0.8 um positively charged Q PES syringe filtration (Pall), 0.8 um negatively charged S PES homemade spin column filtration (Pall), 0.8 um negatively charged S PES syringe filtration (Pall), and 50 nm negatively charged nylon syringe filtration (Sterlitech). Preferably, the charged filter is not housed in a syringe filtration apparatus, as QIAzol/RNA is harder to get out of the filter in these embodiments. Preferably, the charged filter is housed at one end of a column.

In embodiments where the capture surface is a membrane, the membrane can be made from a variety of suitable materials. In some embodiments, the membrane is polyethersulfone (PES) (e.g., from Millipore or PALL Corp.). In some embodiments, the membrane is regenerated cellulose (RC) (e.g., from Sartorius or Pierce).

In some embodiments, the capture surface is a positively charged membrane. In some embodiments, the capture surface is a Q membrane, which is a positively charged membrane and is an anion exchanger with quaternary amines. For example, the Q membrane is functionalized with quaternary ammonium, $R-CH_2-N^+(CH_3)_3$. In some embodiments, the capture surface is a negatively charged membrane. In some embodiments, the capture surface is an S membrane, which is a negatively charged membrane and is a cation exchanger with sulfonic acid groups. For example, the S membrane is functionalized with sulfonic acid, $R-CH_2-SO_3^-$. In some embodiments, the capture surface is a D membrane, which is a weak basic anion exchanger with diethylamine groups, $R-CH_2-NH^+(C_2H_5)_2$. In some embodiments, the capture surface is a metal chelate membrane. For example, the membrane is an IDA membrane, functionalized with minodiacetic acid $-N(CH_2COOH^-)_2$. In some embodiments, the capture surface is a microporous membrane, functionalized with aldehyde groups, $-CHO$. In other embodiments, the membrane is a weak basic anion exchanger, with diethylaminoethyl (DEAE) cellulose. Not all charged membranes are suitable for use in the methods provided herein, e.g., RNA isolated using Sartorius Vivapure S membrane spin column showed RT-qPCR inhibition and, thus, unsuitable for PCR related downstream assay. Additionally, certain membranes generate false positives in downstream immunoassays for protein detection.

In embodiments where the capture surface is charged, EVs can be isolated with a positively charged filter.

In embodiments where the capture surface is charged, the pH during EV capture is a pH≤7. In some embodiments, the pH is greater than 4 and less than or equal to 8.

Depending on the membrane material, the pore sizes of the membrane range from 3 μm to 20 nm.

The surface charge of the capture surface can be positive, negative or neutral. In some embodiments, the capture surface is a positively charged bead or beads.

The methods provided herein include a lysis reagent. In some embodiments, the reagent used for on-membrane lysis is a phenol-based reagent. In some embodiments, the lysis reagent is a guanidinium-based reagent. In some embodiments, the lysis reagent is a high salt-based buffer with or without detergents. In some embodiments, the lysis reagent is a detergent. In some embodiments, the lysis reagent is QIAzol. In some embodiments, the lysis reagent is M-PER or RIPA buffer.

In some embodiments, the methods include one or more wash steps, for example, after contacting the biological sample with the capture surface. In some embodiments, detergents are added to the wash buffer to facilitate removing the non-specific binding (i.e., contaminants, cell debris, and circulating protein complexes or nucleic acids), to obtain a more pure EV fraction. Detergents suitable for use include, but are not limited to, sodium dodecyl sulfate (SDS), Tween-20, Tween-80, Triton X-100, Nonidet P-40 (NP-40), Brij-35, Brij-58, octyl glucoside, octyl thioglucoside, CHAPS or CHAPSO.

In some embodiments, the capture surface, e.g., membrane, is housed within a device used for centrifugation; e.g. spin columns, or for vacuum system e.g. vacuum filter holders, or for filtration with pressure e.g. syringe filters. In a preferred embodiment, the capture surface is housed in a spin column or vacuum system.

In some embodiments, the capture surface, e.g., beads are placed in tubes in different sizes and the procedure can be done with or without rotation. The beads or capture materials are separated by magnet or centrifugation.

The isolation of EVs from a biological sample prior to extraction of nucleic acids is advantageous for the following reasons: 1) extracting nucleic acids from EVs provides the opportunity to selectively analyze disease or tumor-specific nucleic acids obtained by isolating disease or tumor-specific EVs apart from other EVs within the fluid sample; 2) nucleic acid-containing EVs produce significantly higher yields of nucleic acid species with higher integrity as compared to the yield/integrity obtained by extracting nucleic acids directly from the fluid sample without first isolating EVs; 3) scalability, e.g., to detect nucleic acids expressed at low levels, the sensitivity can be increased by concentrating EVs from a larger volume of sample using the methods described herein; 4) more pure or higher quality/integrity of extracted nucleic acids in that proteins, lipids, cell debris, cells and other potential contaminants and PCR inhibitors that are naturally found within biological samples are excluded before the nucleic acid extraction step; and 5) more choices in nucleic acid extraction methods can be utilized as isolated EV fractions can be of a smaller volume than that of the starting sample volume, making it possible to extract nucleic acids from these fractions or pellets using small volume column filters.

The isolation of EVs from a biological sample prior to extraction of proteins or metabolites is advantageous for the following reasons: 1) extracting proteins or nucleic acids from population-specific EVs can reveal changes in their cell of origin and represent alterations occurring in cancer, neurodegenerative diseases and other conditions, making it an accurate and specific biomarker. 2) isolation of population-specific EVs separate the desired biomarker (nucleic acid, lipid or protein) from some of the most abundant proteins, nucleic acids and lipids in body fluid. Specifically, this separates EV specific proteins from albumin in plasma and tamm-horsfall and albumin proteins in urine, improving the sensitivity downstream immune assay and RNA profiling assays. 3) isolation of EVs removes inhibitors of antibody-antigen interaction improving the detection of proteins. 4) isolation of EVs allows for increased starting sample volume. Concentrated EV-associated proteins increase the signal of rare disease relevant proteins.

The isolation of a subpopulation of EVs based on their surface proteins from a biological sample prior to extraction of proteins, nucleic acids or metabolites is advantageous for the following reasons: 1) the selection of EVs that originate from a specific cell or tissue of origin better reflect the mRNA and protein expression of their cell source. For example, isolation of cancer EVs can reveal changes that occur specifically in the cancer, isolation of neuronal EVs open a window into changes taking place within the brain. 2) isolation of subpopulation of EVs can increase the sensitivity of any protein or nucleic acid biomarker as it removes the signal from microvesicles, proteins, and RNAs secreted from all the tissues and cells in the body that are relevant to the disease signal. 3) selection of subpopulation of EVs can also increase the specificity to certain cellular processes, for example isolation EVs containing LAMP2 on their surface reflect lysosomal function, while EVs containing VDAC reflect mitochondrial function. Several methods of isolating EVs from a biological sample have been described in the art. For example, a method of differential centrifugation is described in a paper by Raposo et al. (Raposo et al., 1996), a paper by Skog et al. (Skog et al., 2008) and a paper by Nilsson et. al. (Nilsson et al., 2009). Methods of ion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS) is described in a paper by Taylor and Gercel Taylor (Taylor and Gercel-Taylor, 2008). A method of nanomembrane ultrafiltration concentration is described in a paper by Cheruvanky et al. (Cheruvanky et al., 2007). A method of Percoll gradient isolation is described in a publication by Miranda et al. (Miranda et al., 2010). Further, EVs may be identified and isolated from bodily fluid of a subject by a microfluidic device (Chen et al., 2010). In research and development, as well as commercial applications of nucleic acid biomarkers, it is desirable to extract high quality nucleic acids from biological samples in a consistent, reliable, and practical manner.

In some embodiment, the biological sample is pre-processed prior to an enrichment or depletion method described herein. In some embodiment, the sample is pre-processed prior to isolation and extraction of at least one biomarker disclosed herein. In some embodiment, the sample is not pre-processed prior to isolation and extraction of at least one biomarker disclosed herein. In some embodiments, the sample is not pre-processed prior to isolation and extraction of nucleic acids, e.g., DNA and/or DNA and RNA, from the biological sample.

In some embodiments, the sample is subjected to a pre-processing step prior to when isolation, purification, enrichment or depletion of the EVs is performed to remove large unwanted particles, cells and/or cell debris and other contaminants present in the biological sample. The pre-processing steps may be achieved through one or more centrifugation steps (e.g., differential centrifugation) or one or more filtration steps (e.g., ultrafiltration), or a combination thereof. Where more than one centrifugation pre-processing steps are performed, the biological sample may be centrifuged first at the lower speed and then at the higher speed. If desired, further suitable centrifugation pre-processing steps may be carried out. Alternatively, in addition to the one or more centrifugation pre-processing steps, the biological sample may be filtered. For example, a biological sample may be first centrifuged at 20,000 g for 1 hour to remove large unwanted particles; the sample can then be filtered, for example, through a 0.8 μm filter. In some embodiments, a pre-clearing step is performed on the biofluids with an EDDE blank-depletion.

In some embodiments, the sample is pre-filtered to exclude particles larger than 0.8 μm. In some embodiments, the sample includes an additive such as EDTA, sodium citrate, and/or citrate-phosphate-dextrose.

In some embodiments, one or more centrifugation steps are performed before or after contacting the biological sample with the capture surface to separate EVs and concentrate the EVs isolated from the biological fraction. For example, the sample is centrifuged at 20,000 g for 1 hour at 4° C. To remove large unwanted particles, cells, and/or cell debris, the samples may be centrifuged at a low speed of about 100-500 g, preferably about 250-300 g. Alternatively or in addition, the samples may be centrifuged at a higher speed. Suitable centrifugation speeds are up to about 200,000 g; for example, from about 2,000 g to less than about 200,000 g. Speeds of above about 15,000 g and less than about 200,000 g or above about 15,000 g and less than about 100,000 g or above about 15,000 g and less than about 50,000 g are preferred. Speeds of from about 18,000 g to about 40,000 g or about 30,000 g; and from about 18,000 g to about 25,000 g are more preferred. Particularly preferred is a centrifugation speed of about 20,000 g. Generally, suitable times for centrifugation are from about 5 minutes to about 2 hours, for example, from about 10 minutes to about 1.5 hours, or more preferably from about 15 minutes to about 1 hour. A time of about 0.5 hours may be preferred. It is sometimes preferred to subject the biological sample to centrifugation at about 20,000 g for about 0.5 hours. However, the above speeds and times can suitably be used in any combination (e.g., from about 18,000 g to about 25,000 g, or from about 30,000 g to about 40,000 g for about 10 minutes to about 1.5 hours, or for about 15 minutes to about 1 hour, or for about 0.5 hours, and so on). The centrifugation step or steps may be carried out at below-ambient temperatures, for example at about 0-10° C., preferably about 1-5° C., e.g., about 3° C. or about 4° C. In some embodiments, these ultracentrifugation steps are performed before EDDE. In other embodiments, these steps can be performed after EDDE depletion.

In some embodiments, one or more filtration steps are performed before or after contacting the biological sample with the capture surface. A filter having a size in the range about 0.1 to about 1.0 μm may be employed, preferably about 0.8 μm or 0.22 μm. The filtration may also be performed with successive filtrations using filters with decreasing porosity.

In some embodiments, one or more concentration steps are performed, in order to reduce the volumes of sample to be treated during the chromatography stages, before or after contacting the biological sample with the capture surface. Concentration may be through centrifugation of the sample at high speeds, e.g. between 10,000 and 100,000 g, to cause the sedimentation of the EVs. This may consist of a series of differential centrifugations. The EVs in the pellet obtained may be reconstituted with a smaller volume and in a suitable buffer for the subsequent steps of the process. The concentration step may also be performed by ultrafiltration. In fact, this ultrafiltration both concentrates the biological sample and performs an additional purification of the EV fraction. In another embodiment, the filtration is an ultrafiltration, preferably a tangential ultrafiltration. Tangential ultrafiltration consists of concentrating and fractionating a solution between two compartments (filtrate and retentate), separated by membranes of determined cut-off thresholds. The separation is carried out by applying a flow in the retentate compartment and a transmembrane pressure between this compartment and the filtrate compartment. Different systems may be used to perform the ultrafiltration, such as spiral membranes (Millipore, Amicon), flat membranes or hollow fibers (Amicon, Millipore, Sartorius, Pall, GF, Sepracor). Within the scope of the invention, the use of membranes with a cut-off threshold below 1000 kDa, preferably between 100 kDa and 1000 kDa, or even more preferably between 100 kDa and 600 kDa, is advantageous. In some embodiments, these steps are performed before EDDE. In some embodiments, these steps are performed on EDDE depletion supernatant.

In some embodiments, one or more size-exclusion chromatography step or gel permeation chromatography steps are performed before or after contacting the biological sample with the capture surface. To perform the gel permeation chromatography step, a support selected from silica, acrylamide, agarose, dextran, ethylene glycol-methacrylate co-polymer or mixtures thereof, e.g., agarose-dextran mixtures, are preferably used. For example, such supports include, but are not limited to: SUPERDEX® 200HR (Pharmacia), TSK G6000 (TosoHaas) or SEPHACRYL® S (Pharmacia). In some embodiments, these steps are performed before EDDE. In some embodiments, these steps are performed on EDDE depletion supernatant. Optionally, control particles may be added to the sample prior to EV isolation or nucleic acid extraction to serve as an internal control to evaluate the efficiency or quality of EV purification and/or nucleic acid extraction. In some embodiments, the control particle is a Q-beta bacteriophage, referred to herein as "Q-beta particle." The Q-beta particle used in the methods described herein may be a naturally-occurring virus particle or may be a recombinant or engineered virus, in which at least one component of the virus particle (e.g., a portion of the genome or coat protein) is synthesized by recombinant DNA or molecular biology techniques known in the art. Q-beta is a member of the leviviridae family, characterized by a linear, single-stranded RNA genome that consists of 3 genes encoding four viral proteins: a coat protein, a maturation protein, a lysis protein, and RNA replicase. Due to its similar size to average EVs, Q-beta can be easily purified from a biological sample using the same purification methods used to isolate EVs, as described herein. In addition, the low complexity of the Q-beta viral single-stranded gene structure is advantageous for its use as a control in amplification-based nucleic acid assays. The Q-beta particle contains a control target gene or control target sequence to be detected or measured for the quantification of the amount of Q-beta particle in a sample. For example, the control target gene is the Q-beta coat protein gene. After addition of the Q-beta particles to the biological sample, the nucleic acids from the Q-beta particle are extracted along with the nucleic acids from the biological sample using the extraction methods described herein. Detection of the Q-beta control target gene can be determined by RT-PCR analysis, for example, simultaneously with the biomarker(s) of interest. A standard curve of at least 2, 3, or 4 known concentrations in 10-fold dilution of a control target gene can be used to determine copy number. The copy number detected and the quantity of Q-beta particle added can be compared to determine the quality of the isolation and/or extraction process.

In a preferred embodiment, the Q-beta particles are added to an urine sample prior to nucleic extraction. For example, the Q-beta particles are added to the urine sample prior to ultrafiltration and/or after the pre-filtration step.

In some embodiments, 50, 100, 150, 200, 250, 300, 350, 400, 450, 500, 1,000 or 5,000 copies of Q-beta particles added to a bodily fluid sample. In a preferred embodiment, 100 copies of Q-beta particles are added to a bodily fluid sample. The copy number of Q-beta particles can be calculated based on the ability of the Q-beta bacteriophage to infect target cells. Thus, the copy number of Q-beta particles is correlated to the colony forming units of the Q-beta bacteriophage.

Detection of Nucleic Acid Biomarkers

In some embodiments, the extracted nucleic acid comprises DNA and/or DNA and RNA. In embodiments where the extracted nucleic acid comprises DNA and RNA, the RNA is preferably reverse-transcribed into complementary DNA (cDNA) before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching. Another example of the method comprises two separate steps: a first of reverse transcription to convert RNA into cDNA and a second step of quantifying the amount of cDNA using quantitative PCR. As demonstrated in the examples that follow, the RNAs extracted from nucleic acid-containing particles using the methods disclosed herein include many species of transcripts including, but not limited to, ribosomal 18S and 28S rRNA, microRNAs, transfer RNAs, transcripts that are associated with diseases or medical conditions, and biomarkers that are important for diagnosis, prognosis and monitoring of medical conditions.

For example, RT-PCR analysis determines a Ct (cycle threshold) value for each reaction. In RT-PCR, a positive reaction is detected by accumulation of a fluorescence signal. The Ct value is defined as the number of cycles required for the fluorescent signal to cross the threshold (i.e., exceeds background level). Ct levels are inversely proportional to the amount of target nucleic acid, or control nucleic acid, in the sample (i.e., the lower the Ct level, the greater the amount of control nucleic acid in the sample).

In another embodiment, the copy number of the control nucleic acid can be measured using any of a variety of art-recognized techniques, including, but not limited to, RT-PCR. Copy number of the control nucleic acid can be determined using methods known in the art, such as by generating and utilizing a calibration, or standard curve.

In some embodiments, one or more biomarkers can be one or a collection of genetic aberrations, which is used herein to refer to the nucleic acid amounts as well as nucleic acid variants within the nucleic acid-containing particles. Specifically, genetic aberrations include, without limitation, over-expression of a gene (e.g., an oncogene) or a panel of genes, under-expression of a gene (e.g., a tumor suppressor gene such as p53 or RB) or a panel of genes, alternative production of splice variants of a gene or a panel of genes, gene copy number variants (CNV) (e.g., DNA double minutes) (Hahn, 1993), nucleic acid modifications (e.g., methylation, acetylation and phosphorylations), single nucleotide polymorphisms (SNPs), chromosomal rearrangements (e.g., inversions, deletions and duplications), and mutations (insertions, deletions, duplications, missense, nonsense, synonymous or any other nucleotide changes) of a gene or a panel of genes, which mutations, in many cases, ultimately affect the activity and function of the gene products, lead to alternative transcriptional splice variants and/or changes of gene expression level, or combinations of any of the foregoing.

The analysis of nucleic acids present in the isolated particles is quantitative and/or qualitative. For quantitative analysis, the amounts (expression levels), either relative or absolute, of specific nucleic acids of interest within the isolated particles are measured with methods known in the art (described below). For qualitative analysis, the species of specific nucleic acids of interest within the isolated EVs, whether wild type or variants, are identified with methods known in the art.

The present invention also includes various uses of the new methods of isolating EVs from a biological sample for high quality nucleic acid extraction from a for (i) aiding in the diagnosis of a subject, (ii) monitoring the progress or reoccurrence of a disease or other medical condition in a subject, or (iii) aiding in the evaluation of treatment efficacy for a subject undergoing or contemplating treatment for a disease or other medical condition; wherein the presence or absence of one or more biomarkers in the nucleic acid extraction obtained from the method is determined, and the one or more biomarkers are associated with the diagnosis, progress or reoccurrence, or treatment efficacy, respectively, of a disease or other medical condition.

Kits for Isolating EVs from a Biological Sample

One aspect of the present invention is further directed to kits for use in the methods disclosed herein. The kit comprises a capture surface apparatus sufficient to separate EVs from a biological sample from unwanted particles, debris, and small molecules that are also present in the biological sample. The present invention also optionally includes instructions for using the foregoing reagents in the isolation and optional subsequent nucleic acid extraction process. In another aspect, the kit comprises a capture surface apparatus sufficient to separate a subpopulation of EVs that contain surface marker GluR2 used for isolating EVs unwanted particles, debris, and small molecules that present in a biological sample. The present invention also optionally includes instructions for using the foregoing reagents in the isolation and optional subsequent nucleic acid extraction process.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

While the examples provided herein use a variety of membranes and devices used for centrifugation and/or filtration purposes, it is to be understood that these methods can be used with any capture surface and/or housing device that allows for the efficient capture of EVs and release of the nucleic acids, particularly, RNA, contained therein.

Example 1: EDDE Process and Uses Thereof

As described throughout, the processes provided herein allow the user to choose a different selection of antibodies for isolating specific subpopulations of EVs. The process is suitable for the measurement of proteins, protein modifications, sugars, lipids, RNA, DNA, RNA/DNA modifications and mutations, as well as metabolites, and any combination thereof.

The methods disclosed herein are generally referred to as "EDDE process" or "EDDE". As used herein, the term "EDDE process" or "EDDE" refers to the following general method: i) functionalizing a capture surface with a reagent that is specific to one or more cell surface markers on EVs generally or is specific to one or more cell surface markers on one or more subpopulations of EVs to isolate the total EV population or one or more subpopulations of EVs from a biological sample; ii) contacting the functionalized capture surface with the biological sample; iii) performing a depletion step, performing an enrichment step, or a combination thereof to produce a purified total EV population or one or more subpopulations of EVs; and iv) eluting the purified total EV population or one or more subpopulations of EVs or further manipulating the purified total EV population or one or more subpopulations of EVs, such as, for example, by lysing the EVs within the purified total EV population or one or more subpopulations of EVs. In some embodiments, the eluted purified total EV population or one or more subpopulations of EVs are then subjected to further downstream analysis.

For a depletion process, step iii) includes at least transferring the supernatant from step ii) to a new tube or other container and isolating the EVs from the supernatant using a suitable capture surface. In some embodiments, the EVs from the supernatant are eluted intact from the suitable isolation capture surface. In some embodiments, the EVs from the supernatant are lysed, and the nucleic acids from the lysed EVs are extracted. In some embodiments, the eluted intact EVs or the nucleic acids extracted therefrom are then subjected to further downstream analysis. In some embodiments, nucleic acids, proteins or lipids are isolated directly from the depleted body fluids.

For an enrichment process, step iii) washing the functionalized capture surface that has been contacted with the biological sample from step ii) and transferring the washed capture surface to a new tube or other container. In some embodiments, the EVs are eluted intact from the washed capture surface. In some embodiments, the EVs are lysed, and the nucleic acids from the lysed EVs are extracted. In some embodiments, the eluted intact EVs or the nucleic acids extracted therefrom are then subjected to further downstream analysis.

The FIGURE provided herein demonstrate various advantages and other aspects of the EDDE isolation and purification processes provided herein.

As shown in FIG. 1, one exemplary process of the invention starts with a bio-fluid like serum or plasma. Subpopulation of EVs are separated from the biofluids specifically by any bio-affinity molecule. EVs can be separated by charge affinity. Total sample EVs may also be isolated. Specific EVs isolated using capture surfaces are retrieved from the capture surface.

All specific and total exosomes are analyzed for biomarkers or profiles using downstream assays. FIG. 2A depicts that HBB mRNA was significantly reduced by 81% following the isolation processes referred to herein as EDDE as measured by quantitative PCR. FIG. 2B depicts that HBB protein concentration in plasma EVs was significantly reduced by 55% as measured by specific ELISA. FIG. 2C depicts the level of HBB, HBA1 and HBA2, which are the three most abundant mRNA in plasma, are reduced by 67%, 63%, and 66% respectively following the EDDE process as determined by RNAseq.

FIG. 3A depicts how PPBP mRNA was significantly reduced by 81% following EDDE (SELP) as measured by quantitative PCR. FIG. 3B depicts how SELP protein concentration in plasma exosomes was significantly reduced by 80% as measured by specific ELISA. FIG. 3C demonstrates that the level of PPBP, PF4v1 and PF4, which are the three most abundant platelet mRNA in plasma EVs, was reduced by 67%, 63%, and 66% respectively following EDDE (SELP) as determined by RNAseq.

The next set of studies demonstrate the superior, sensitive ability of the EDDE process to detect protein-coding genes in EVs. Prior to the EDDE process, in plasma samples, some exosomal RNAs are present, but not typically detected due to the presence of non-relevant background genes that are also sequenced. When EDDE was used to remove background EVs, genes that were undetected in plasma were detected as seen in FIG. 4A. Several hundred of these protein-coding genes were detected, and FIGS. 4B and 4C present a representative few of the protein-coding genes that were detected following EDDE.

FIG. 5 depicts that when T47D cell line condition media was spiked into healthy plasma pool, the recovery level of various breast cancer specific genes, GATA3, KRT19, RAB13, SAMD4A, ARHGAP11a, ANP32B and TAF15, was higher when CD44 and CD184 was targeted using anti-CD44 antibodies and/or anti-CD184 antibodies, separately or together, than with a non-specific antibody.

FIG. 6 demonstrates that the EDDE process improved the specificity of an abundant biomarker. Like many protein biomarkers, c-Met is present in most samples and lacks specificity. Use of the EDDE process revealed relevant cancer-related signal from the non-relevant background.

As shown in FIG. 7, many biomarkers are expressed at levels too low to be efficiently detected in total plasma. These biomarkers can be detected after EDDE enrichment. As an example, PD-1 in FIG. 7A, Tau in FIG. 7C and p-Tau proteins (FIG. 7B) are barely detected in total plasma, but after the novel enrichment (EDDE process) of a subpopulation of EVs from the same sample, the biomarker is robustly detected. The Tau signal was detected after enrichment of neuronal exosomes using specific antibody targeting markers such as L1CAM. PD-1 was detected after enriching for CD81 and CD3 containing EVs.

Figure 7A:
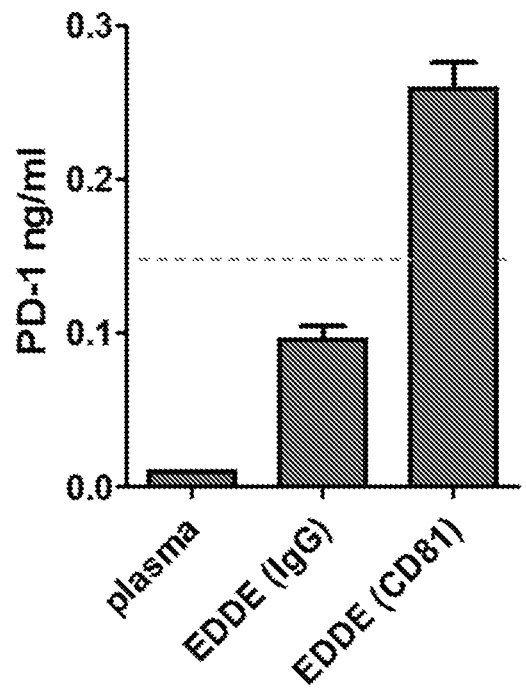
Figure 7B:
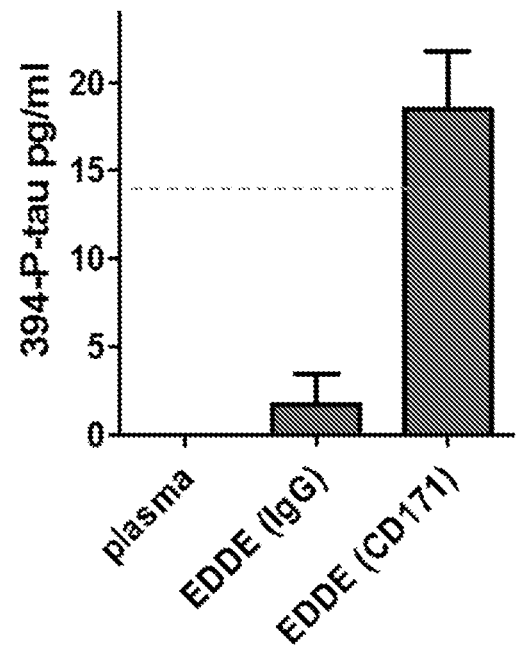
Figure 7C:
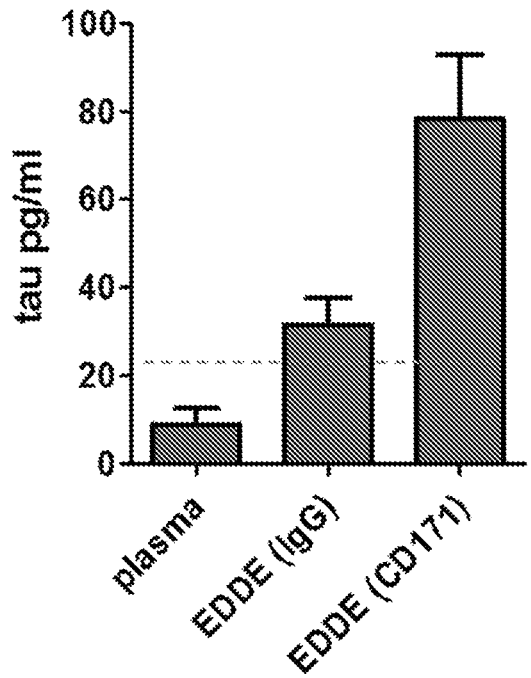
Figure 7D:
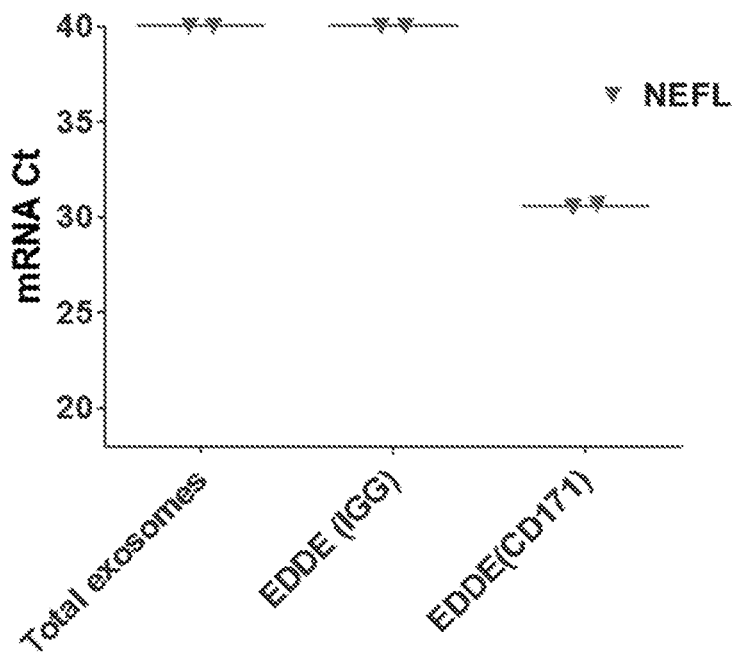

FIG. 7A demonstrates that enriching for EVs that contain CD81 on their surface using the EDDE process significantly enabled the detection of PD-1 in plasma samples, and PD-1 was undetected in the unprocessed plasma sample. FIGS. 7B and 7C demonstrate that enriching for EVs containing CD171 on their surface enabled detection of total tau and p-tau in plasma samples by regular ELISA. FIG. 7D demonstrates that enriching for EVs that contain CD171 on their surface enabled the detection of NEFL mRNA in EVs from plasma sample and directly from plasma. The process of enrichment using the EDDE process also increased the signal of NRGN and ENO2 by 2-4 fold.

FIG. 8 demonstrates that an EDDE plasma RNA panel accurately distinguished 100% of patients who went on to achieve a 12-month durable response to immunotherapy (yellow bars) after only 2-4 weeks on ipilimumab (study of 21 patients). In contrast, a total plasma exosomal RNA signature had a 12.5% false positive rate.

Example 2: EDDE Depletion of Abundant Genes in Human Normal and Cancer Plasma

Metastatic melanoma patient plasma drawn at baseline (before initiation of immunotherapy) and taken at week 2/4 after initiation of immunotherapy was subjected to preclearing using filtration method(s). EDDE immune capture procedure was performed on plasma to remove abundant reticulocyte and pre-erythrocyte EVs expressing glycophorin A (CD235A) that contain nonrelevant RNA transcripts. Exosomes were isolated from the remaining unbound plasma, cleared of CD235A EVs, and exosomal RNA was isolated. An mRNA panel of over 600 mRNA transcripts was used to examine the expression in samples taken at baseline versus at week 2/4 post immunotherapy. Genes with the greatest expression change between timepoints were identified. As seen in FIG. 8 the top ten differentially expressed genes identified after EDDE depletion were able to separate samples from individuals who responded to immunotherapy (yellow dendrogram) from those who did not respond to immunotherapy (green dendrogram). This separation was not seen when differentially expressed genes were identified in the same patient plasma samples not processed using EDDE CD235A depletion.

Human plasma although considered a cell-free medium for analyzing circulating tumor biomarkers, has abundant genes that are typically not useful in oncology analysis especially for solid tumors, among them, human hemoglobin and platelet-related genes. The EDDE depletion process disclosed here could effectively deplete these irrelevant abundant genes to a significant extent by virtue of EV depletion targeting against cell surface markers. As shown in FIG. 9, an anti-GYPA (CD235) antibody, and an anti-CD42 (plus anti-CD62) antibody were used to deplete erythrocyte/reticulocyte-derived EVs, and platelet-derived EVs, respectively. The result of depleting reticulocyte/erythrocyte EVs is that some of the most abundant mRNAs in plasma (HBB, HBA1, HBA2, MT-ND1, MT-ND4L and MT-CO1) were removed for downstream analysis by over 50% as measured in transcripts per million by RNASeq.

As shown in FIG. 12A and FIG. 12B for a platelet-derived EV depletion, the effect of EDDE was demonstrated by PPBP RNA level analyzed by qPCR (Ct). It is clear that the depletion using magnetic beads (e.g., from Thermo Fisher, Waltham, MA, USA) and EDDE immuno pulldown resulted in platelet-derived EV signal being mostly on the beads, and significantly reduced in the plasma supernatant after EDDE depletion process. Combination of two surface markers for platelet-derived EVs (CD42+CD62) resulted in an even greater depletion in plasma supernatant after EDDE, further enabling useful downstream RNA analysis.

In FIG. 17 (left part), 2 mL of human normal plasma was used in three independent replicates each to undergo an EDDE depletion using a CD235 antibody-conjugated magnetic beads (Thermo Fisher, Waltham, MA) with bead-washing using detergent-containing buffers for multiple times. The unbound portion of human plasma after removing the complex formed between the functionalized magnetic beads and cell surface marker CD235 was subject to RNA extraction using QIAzol-based method for HBB gene copies measured by quantitative PCR. As a control, IgG was used in EDDE process instead of the specific antibody for 235, and the same HBB gene was also measured in the unbound portion of plasma. Total plasma neat was extracted for RNA to measure the starting amount of HBB gene copy number. Depletion of HBB for more than 4 fold (corresponding to Ct change of 2.8 Ct) was observed.

Example 3: EDDE Enrichment in Conditioned Cancer Cell Culture Media and Normal Human Plasma As shown in FIG. 10, a conditioned cell media from human glioblastoma cancer cell line Gli36 wild-type, that is known to expresses wild-type EGFR membrane protein on the cell surface, was used for immune pulldown using standard EDDE enrichment procedure disclosed herein, with IgG as a control and antibodies against CD63, CD81, EGFR1 cell surface markers, respectively. After specific EVs were pulled down using these antibodies, RNA was extracted from the purified subpopulation of EVs, before subsequent analysis by quantitative PCR for the GAPDH gene expression. It was clearly demonstrated that either exosome-specific markers (CD63, CD81), or EGFR marker that is unique to this cancer cell line, could efficiently enrich for subpopulations of EVs in the conditioned medium.

As shown in FIG. 11, a list of potential surface proteins on exosomes were targeted for either enrichment or for depletion in human plasma using EDDE platform with a summarized level of confidence.

Example 3: EDDE Enrichment in Normal Human Plasma Vs. Cancer Patient Plasma

As shown in FIG. 14, human melanoma patient plasma, and healthy subject plasma were used for immune pulldown using standard EDDE enrichment procedure disclosed herein, with IgG as a control and antibodies against CD44 cell surface marker. It was demonstrated that only CD44 cell surface marker-based EDDE specifically enriched a subpopulation of EVs (carrying biomarker of cMET protein on the surface, in this case) from the plasma of melanoma patients A and B relative to the healthy subject, enabling clear separation of melanoma patients from the healthy subject, potentially for the early detection of melanoma. The separation was not seen in neat plasma detection of c-MET protein, if EDDE enrichment was not performed.

As shown in FIGS. 15A and 15B, human glioblastoma patient plasma, and healthy subject plasma were used for immune pulldown using standard EDDE enrichment procedure disclosed herein, with IgG as a control and antibodies against CD44, EGFR, and EGFRvIII cell surface markers, respectively. It was demonstrated that only EGFR cell surface marker out of these tested markers showed specificity in EDDE enrichment for a subpopulation of EVs from the GBM patient plasma relative to the healthy. The enriched subpopulation of EVs showed characteristic exosomal markers like FLOT1 and CD81, by western blot analysis.

Example 4: EDDE Enrichment of Neuronal Protein Biomarkers in Normal and Neurodegenerative Disease Patient Plasma Samples Neuronal-associated proteins are detected in plasma EVs after specific enrichment of neuronal-derived EVs. Individual or pooled healthy plasma was first pre-cleared using filtration method(s). In FIG. 17B, FIG. 18 and FIG. 20 EDDE immune pulldown procedure was performed on plasma targeting EVs with either L1 CAM or GluR2 protein on their surface. This EDDE procedure was performed manually by human operator(s) or using automated bead/liquid handling equipment. L1CAM or GluR2-expressing EVs from plasma were immuno captured on a surface and separated away from the unbound portion of the plasma. These EVs were removed from their capture surface and/or lysed to generate EV protein extracts. These EV extracts were then interrogated by standard or modified protein detection method for known neuronal-associated proteins expressed in neuronal tissue, including Tau, p-Tau, p-181 Tau, SCNA and ENOS2. Only the EV lysates from the enrichment process targeting L1CAM or GluR2 detected the presence and/or increase of neuronal-associated proteins; EDDE control IgG could not. EDDE targeting L1CAM and GluR2 are specifically capturing neuronal-associated EVs and are not indiscriminately retrieving EVs in the blood as HBB, an abundant blood protein found in plasma and plasma exosomes, was not enriched by the L1CAM and GluR2 EDDE process. As seen in FIG. 16 and FIG. 21 plasma from patients with neurodegenerative disease or from individuals having risk of neurodegenerative diseases (plasma from patients aged >60), undergo EDDE procedure for immune capture of L1CAM and GluR2-expressing EVs in plasma. After immune capture, L1CAM or GluR2 positive EVs are physically separated from liquid plasma and retained. These neuronal sub-type EVs are released from the immune capture surface and/or lysed to generate neuronal EV lysates that are analyzed by standard or modified protein identification methods. As seen in FIG. 21, Parkinson's Disease (PD) samples can only be distinguished from control healthy samples when neuronal-associated protein alpha synuclin (SNCA) is measured after EDDE L1CAM or EDDE GluR2 process. Here for the GluR2 EDDE enrichment, a threshold of a-synuclein in this EDDE enrichment assay is set at 9 pg/ML of plasma to achieve 100% sensitivity and 100% specificity in distinguishing Parkinson's patients from normal healthy subjects. In unprocessed plasma and in unprocessed CSF, SNCA concentration is not different between disease and health groups. Similarly, as seen in FIG. 16 when EDDE L1CAM procedure is performed on senior plasma (aged >60 years) and young plasma (aged <50 years) and Tau concentration (a neuronal protein associated with AD) is measured on these EV lysates, the concentration of Tau is higher in senior samples. Tau was not detected in plasma depleted of exosomes by ultracentrifugation method.

Example 5: EDDE Enrichment of Neuronal RNA Biomarkers in Normal and Neurodegenerative Disease Patient Plasma Samples Up to 2 mL of human healthy donor plasma, that were pooled typically from 10 subjects, was used in experiments leading to qPCR analysis on RNA extracted from EDDE enriched EVs having target cell surface marker(s). In FIG. 13, neuronal specific genes such as NRGN ENO2 and NEFL were shown to achieve enrichment in human plasma after EDDE enrichment when specific antibodies (biotinylated) were used to functionalize the contact surface in magnetic beads with streptavidin attached. The complex formed between the beads and the EVs containing surface marker of CD171 (L1CAM) was washed before being lysed using QIAzol reagent for RNA extraction. The RNA was purified and subsequent qPCR analysis was conducted using primers and probe specific for the neuronal genes, respectively. The similar process was conducted for experiments in FIG. 19, where neuronal genes NEFL, NRGN, ENO2, SNSR4, and GRP139 were analyzed, as a control, HBB was also analyzed for comparison. The EDDE enrichment process was performed using CD171 (EDDE-neuro 1) and GluR2 (EDDE-neuro 2), respectively. As shown in FIG. 22 and FIG. 23, neuronal EDDE enrichment using L1CAM and GluR2 significantly enriched for neuronal specific genes but not for HBB, as a control, a non-neuronal DRD5 EDDE did not enrich for this set of neuronal genes.

In FIG. 24, ten Parkinson's patient's plasma and ten age-matched normal human plasma were analyzed side by side for neuronal specific genes after EDDE enrichment using either L1CAM or GluR2 antibody. In these candidate genes, without normalization, GluR2 EDDE enrichment separated Parkinson's patients from normal using neuronal genes PARK2 and DLG4, with a pre-defined threshold Ct, respectively.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following.

What is claimed is:
1. A method for treating Parkinson disease in a subject, the method comprising:
   a) contacting a biological sample from the subject with a functionalized capture surface to form a complex between the functionalized capture surface and EVs comprising the at least one cell surface marker, wherein the capture surface is functionalized with a reagent that specifically binds the at least one cell surface marker, wherein the at least one surface marker is Glutamate ionotropic receptor AMPA type subunit 2 (GluR2);
   b) separating the formed complex from an unbound portion of the biological sample to obtain a captured complex;
   c) washing the captured complex;
   d) eluting the EVs comprising the at least one surface marker from the functionalized capture surface or lysing the EVs complexed with the functionalized capture surface;
   e) extracting at least one target biomarker from the eluted or lysed EVs, wherein the at least one target biomarker is parkin (PARK2) RNA;
   f) determining the expression level of the at least one biomarker extracted in step (e);
   g) identifying the subject as having Parkinson disease by comparing the expression level of the at least one target biomarker to a corresponding pre-defined threshold; and;

h) administering at least one therapy for Parkinson disease to the subject.

2. The method of any one of claim 1, wherein the at least one reagent that specifically binds the at least one cell surface marker comprises an antibody, a mixture of antibodies, a vitamin, a protein, a ligand, a lectin, a peptide, an oligonucleotide, an aptamer, or any combination thereof.

3. The method of claim 1, wherein the biological sample is selected from the group consisting of blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof.

4. The method of claim 3, wherein the biological sample is plasma or serum.

5. The method of claim 1, wherein the functionalized capture surface comprises a population of beads or a mixture of a population of beads.

6. The method of claim 5, wherein the beads are magnetic beads.

7. The method of claim 1, wherein the functionalized capture surface comprises one or more of a membrane, chip, nanoparticle or population of nanoparticles, nanotube or population of nanotubes, slide, chromatography medium, or any combination thereof.

8. The method of claim 1, wherein determining the expression level of the at least one target biomarker comprises using a transcriptomic assay, quantitative PCR, a nanostring assay, a microarray or any combination thereof.

\* \* \* \* \*